United States Patent [19]

Lednicer

[11] 4,180,584
[45] Dec. 25, 1979

[54] 4-PYRROLIDINO-CYCLOHEXANONE KETALS

[75] Inventor: Daniel Lednicer, Portage, Mich.

[73] Assignee: The Upjohn Company, Kalamazoo, Mich.

[21] Appl. No.: 840,861

[22] Filed: Oct. 11, 1977

Related U.S. Application Data

[62] Division of Ser. No. 692,589, Jun. 3, 1976, Pat. No. 4,065,573.

[51] Int. Cl.$^2$ .................. C07D 295/08; C07D 295/10; H61K 31/40
[52] U.S. Cl. .......................... 424/274; 260/326.5 SM; 260/326.5 S; 260/326.36; 260/326.5 D
[58] Field of Search ................ 260/326.50, 326.5 SM, 260/326.36, 326.5 S; 424/274

[56] References Cited

U.S. PATENT DOCUMENTS 4,065,573  12/1977  Daniel Lednicer ............... 260/340.7

Primary Examiner—José Tovar
Attorney, Agent, or Firm—John J. Killinger

[57] ABSTRACT

A class of new 4-amino-4-arylcyclohexanones, their ketals, and acid addition salts have been synthesized and found to be useful for relieving pain in animals. Their analgesic activity appears to be of high order, and in addition some exhibit narcotic antagonist activity that is useful in modifying the cardiovascular, respiratory, and behavioral depression caused by other analgesics. Several show mixed analgesic and narcotic antagonist activity. Preferred compounds of the class are 4-(m-hydroxyphenyl)-4-dimethylaminocyclohexanone ethylene ketal, and 4-(m-hydroxyphenyl)-4-(n-butylmethylamino)cyclohexanone ethylene ketal as free bases and as their hydrochloride salts.

Processes for snythesis and intermediates are described. Unit dosage forms and therapeutic treatments are disclosed.

6 Claims, No Drawings

4-PYRROLIDINO-CYCLOHEXANONE KETALS

This is a division of application Ser. No. 692,589, filed June 3, 1976, now U.S. Pat. No. 4,065,573, issued Dec. 27, 1977.

SUMMARY OF THE INVENTION

This invention pertains to some new organic chemical compounds that are active as analgesics (Formula I), and also to novel compounds useful as intermediates in the preparation of the compounds of Formula I, such as Formulae II, III, IV, and V, and acid addition salts when the amino functionality is present,

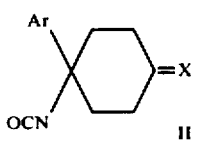
II

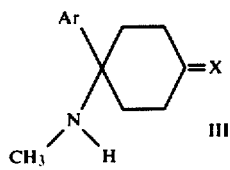
III

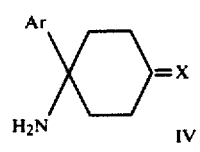
IV

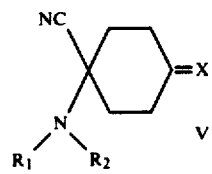
V wherein Ar, $R_1$, $R_2$, and X are as defined below.

The invention is more particularly directed to some new 4-amino-4-arylcyclohexanones, their ketals, and acid addition salts thereof, two processes for preparing the same; and a method and formulations for treating pain in animals and humans.

The new 4-amino-4-arylcyclohexanones and ketals are represented by the general schematic formula:

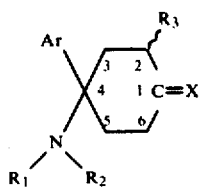

Formula I wherein X is oxo, and

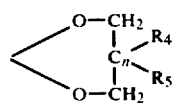

wherein n is zero or one and $R_4$ is hydrogen or methyl; $R_5$ is hydrogen, phenyl, —$CH_2$-alkenyl wherein alkenyl is of 2 to 4 carbon atoms, inclusive, or methyl; aryl is thiophene, or

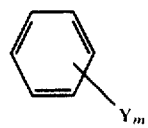

wherein m is zero, one or two, and Y is halogen, $CF_3$, alkyl of 1 to 4 carbon atoms, inclusive, alkoxy of 1 to 4 carbon atoms, inclusive, hydroxy, cycloalkyloxy of 3 to 6 carbon atoms, inclusive, alkanoyloxy of 2 to 4 carbon atoms, inclusive, alkylthio of 1 to 4 carbon atoms, inclusive, or

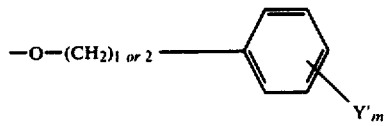

where Y' is halogen, $CF_3$, alkyl of 1 to 4 carbon atoms, inclusive, or alkoxy of 1 to 4 carbon atoms, inclusive, $R_1$ is hydrogen, or lower alkyl of 1 to 8 carbon atoms, inclusive, $R_2$ is hydrogen, lower alkyl of 1 to 8 carbon atoms, inclusive, —$CH_2$-alkenyl wherein alkenyl is of 2 to 8 carbon atoms, inclusive, acetyl, cycloalkylalkyl wherein cycloalkyl is of 3 to 6 carbon atoms, inclusive, and alkyl is of 1 to 3 carbon atoms, inclusive, $\beta$-hydroxyethyl, carbethoxymethyl, cycloalkyl of 3 to 6 carbon atoms, inclusive,

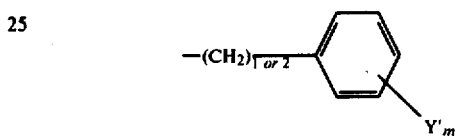

or

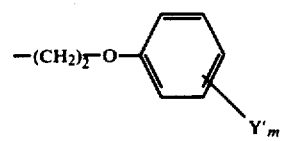

$R_3$ is hydrogen, lower alkyl of 1 to 5 carbon atoms, inclusive; and

can be a saturated cycloalkylamino group

wherein n' is 3, 4, 5, or 6; or mono- or di-alkyl substituted cycloalkylamino wherein each alkyl is of 1 to 3 carbon atoms, inclusive; and the acid addition salts thereof.

$R_1$ and $R_2$ taken together with the nitrogen atom to which they are attached form a saturated cycloalkylamino group

wherein n' is 3, 4, 5, or 6, and mono- or di-alkyl substituted cycloalkylamino wherein each alkyl is from 1 to 3 carbon atoms, inclusive.

The wavy line (~) denotes the possibility of cis-trans stereoisomerism with respect to substitution at the 4-position.

When $R_3$ is lower alkyl, the carbon atom to which $R_3$ is attached (#2) becomes asymmetric (possesses chirality and the 2-substituted cyclohexanone can exist as two enantiomers which can be resolved by known methods.

In compounds of the formula:

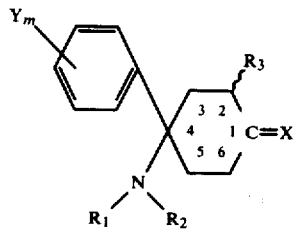
VI wherein $Y_m$, $R_1$, $R_2$, $R_3$, and X are as defined above, since the Y variable can be hydroxy, the compounds of the invention include 4-(meta-hydroxyphenyl)-4-aminocyclohexanones, their ketals, and acid addition salts that are particularly interesting and especially preferred. They exhibit excellent narcotic antagonist activity in addition to their own analgesic effect. They are therefore prospectively useful for antagonizing the toxic effects of morphine, meperidine, and codeine by inhibition of the cardiovascular, respiratory, and behavioral depression caused by these and other potent analgesics. These also possess the additional useful property of low physical dependence liability as measured by methods described by E. L. Way, et al., *J. Pharmacol. Exp. Ther.*, 167, 1 (1969), J. K. Sealens, et al., *Arch. Int. Pharmacodyn.*, 190, 213 (1971), and S. E. Smits, *Res. Commun. in Chem. Path. and Pharmac.*, 10, 651 (1975).

A preferred class of compounds for analgetic activity are compounds of the formula:

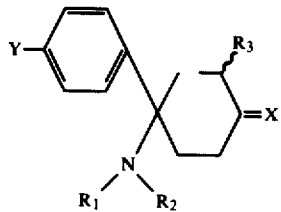
Formula VII wherein X is oxo or

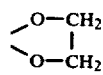

$R_3$ is hydrogen or lower alkyl of from 1 to 5 carbon atoms, inclusive, Y is halogen, $CF_3$, alkyl of 1 to 4 carbon atoms, inclusive, alkoxy of 1 to 4 carbon atoms, inclusive, hydroxy or alkanoyloxy of 2 to 4 carbon atoms, inclusive, and $R_1$ is hydrogen, or lower alkyl of 1 to 8 carbon atoms, inclusive, $R_2$ is hydrogen, lower alkyl of 1 to 8 carbon atoms, inclusive, —$CH_2$-alkenyl wherein alkenyl is of 2 to 8 carbon atoms, inclusive, acetyl, cycloalkylalkyl wherein cycloalkyl of 3 to 6 carbon atoms, inclusive, and alkyl is of 1 to 3 carbon atoms, inclusive, β-hydroxyethyl, carbethoxymethyl, cycloalkyl of 3 to 6 carbon atoms, inclusive,

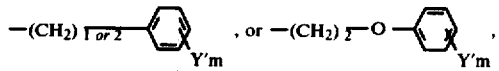

and $R_3$ is hydrogen, lower alkyl of 1 to 5 carbon atoms, inclusive, and

can be a saturated cycloalkylamino group

wherein n' is 3, 4, 5, or 6; or mono- or di-alkyl substituted cycloalkylamino wherein each alkyl is of 1 to 3 carbon atoms, inclusive; and the acid addition salts thereof.

An especially preferred class of compounds for analgetic activity coupled with lower to moderate physical dependence liability are compounds of the formula:

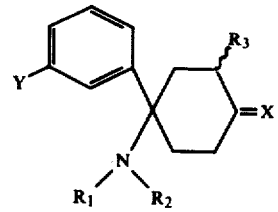
VIII wherein X is oxo or

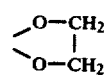

$R_3$ is hydrogen or lower alkyl of from 1 to 5 carbon atoms, inclusive, $R_1$ is lower alkyl of from 1 to 8 carbon atoms, inclusive, $R_2$ is lower alkyl of from 1 to 8 carbon atoms, inclusive, β-hydroxyethyl, cycloalkylalkyl wherein cycloalkyl is from 3 to 6 carbon atoms, inclusive, and alkyl is from 1 to 3 carbon atoms, inclusive, acetyl or carbethoxymethyl; and Y is hydroxy, alkanoyloxy of 2 to 4 carbon atoms, inclusive, alkoxy of 1 to 4 carbon atoms, inclusive, or

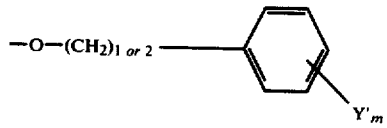

wherein m is 0, 1, or 2 and Y' is alkyl of 1 to 4 carbon atoms, inclusive, or alkoxy of 1 to 4 carbon atoms, inclusive.

It is accordingly a general object of this invention to provide novel and useful analgesic agents, new and appropriate formulations of the new compounds designed for administration to humans and animals, e.g., cats, dogs, cows, horses, suffering from pain, and a novel method for treating and relieving pre-treatment pain in animals. Other more limited objects of this invention, such as the new syntheses of the desired new active compounds and intermediates, will be apparent to those skilled in the art as this description of the invention becomes more detailed

DETAILED DESCRIPTION OF THE INVENTION

In the foregoing schematic representation (see Formula I, above) of the new 4-amino-4-arylcyclohexanones and ketals of this invention, the variable X is defined as oxo(=O) when a cyclohexanone itself is intended. Otherwise the X variable represents an alkylene ketal which is preferably an ethylene ketal, i.e., a spiro-1,3-dioxolane group, but is also trimethylene ketal. For purposes of consistency and perhaps simplicity the ethylene ketals are named as 1- or 2-substituted ethylene.

When the alkylene ketal has a trimethylene chain, the chain carbons can be similarly hydrocarbon, optionally substituted by lower-alkyl, lower alkenyl, phenyl, benzyl, phenethyl, or other non-critical, non-interfering hydrocarbon groups. This group with two oxygens and the cyclohexanone carbon form a spiro-1,3-dioxane group. These are conveniently designated as 2-substituted trimethylene.

As stated, the new 4-amino-4-arylcyclohexanones, ketals, and acid addition salts of this invention, represented by schematic Formula I, above, as limited by defined variables, are active as analgesics. The compounds have been discovered to in some way interfere with nerve transmission or cortical awareness of normally painful insults to the animal body. By and large this interfering action has been observed to be physiologic, and no major interference with other physiological activities of the body has been observed. The new compounds can therefore be used to treat and relieve pain regardless of origin in animals and humans.

Certain compounds of this invention are extremely potent and desirable analgesics. Many of them are comparable to or exceed in potency the well-known analgesic meperidine (N-methyl-4-phenyl-4-carbethoxypiperidine) and are therefore preferred as pure analgetics. Among these many preferred, newly prepared, and tested compounds are 4-(p-chlorophenyl)-4-dimethylaminocyclohexan-1-one, ethylene ketal;
4-(p-fluorophenyl)-4-dimethylaminocyclohexan-1-one, ethylene ketal;
4-(p-bromophenyl)-4-dimethylaminocyclohexan-1-one, ethylene ketal;
4-dimethylamino-4-(p-tolyl)cyclohexan-1-one, ethylene ketal;
4-(p-anisyl)-4-dimethylaminocyclohexan-1-one, ethylene ketal;
4-(p-tolyl)-4-dimethylaminocyclohexanone;
4-(p-bromophenyl)-4-dimethylaminocyclohexanone; and
4-(p-chlorophenyl)-4-dimethylaminocyclohexanone.

Other preferred compounds of this invention for low physical dependence liability activity and analgetic activity are 4-(m-hydroxyphenyl)-4-dimethylaminocyclohexan-1-one, ethylene ketal;
4-(m-hydroxyphenyl)-4-(methyl-n-butylamino)cyclohexan-1-one, ethylene ketal hydrochloride,
4-(m-hydroxyphenyl)-2-methyl-4-dimethylaminocyclohexan-1-one and its ketals.

The (Y) variable substituent on the 4-phenyl ring can be any of a wide variety of non-interfering elemental atoms and organic groups. Illustratively, Y can be halogen, $CF_3$, alkyl of from 1 to 4 carbon atoms, inclusive; alkoxy of from 1 to 4 carbon atoms, inclusive; alkylthio of from 1 to 4 carbon atoms, inclusive; hydroxy; alkanoyloxy of 2 to 4 carbon atoms;

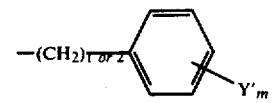

as defined above.

Specific examples of the foregoing general classes of elemental atoms and organic groups include: chlorine, bromine, iodine, fluorine, methyl, ethyl, propyl, butyl, isopropyl, isobutyl, methoxy, ethoxy, propoxy, trifluoromethyl, methylthio, ethylthio, tert-butylthio, benzyloxy, and acetoxy.

Representative $CH_2$-alkenyl wherein alkenyl is of 2 to 8 carbon atoms include such groups as 3-methyl-2-butenyl, 4-ethyl-2-hexenyl, 3-methyl-2-hexenyl, allyl, methallyl, and the like. Cycloalkylalkyl may be cyclohexylmethyl, cyclopropylmethyl, cyclopentylethyl and the like. The foregoing are just samples of such acceptable groups.

The characteristic

group has been broadly defined above, and it will be recognized by those skilled in the art that any of a great variety of "amino" groups can be employed. For purposes of exemplification only, some representative basic nitrogen groups are specified. The methylamino embodiment was obtained in many of the intermediates. Likewise, a 4-allylmethylamino group, a butylmethylamino group, a (carbethoxymethyl)methylamino group, a (2-hydroxyethyl)methylamino group, and a methyl acetamido group are embodiments actually prepared in final compounds.

Other representative "amino" embodiments consistent with the general description include: loweralkylamino, dilower-alkylamino, lower-alkenylamino, cycloaliphaticamino of from 3 to 6 carbon atoms, inclusive, (cycloaliphaticalkyl)amino of from 4 to 9 carbon atoms, inclusive, loweralkyl alkanamido of from 3 to 6 carbon atoms, inclusive, 1-pyrrolidinyl, 1-piperidinyl, 4-alkylpiperidinyl, 3-alkylpyrrolidinyl, and 3,4-dialkylhexamethyleneimino.

The basic amino nitrogen endows the new compounds of this invention with the facility for preparation of acid addition salts. In order to accomplish this transformation, the free bases are merely reacted with a selected acid, preferably in the presence of an organic solvent substantially inert to the basic compound, the acid, and the acid addition salt that is formed. Anhydrous conditions are preferred. The salt usually precipitates from an appropriate organic solvent or it can be recovered by evaporation of solvent until crystallization occurs, followed by filtration.

Acid addition salts suitable for physiological analgesia are necessarily non-toxic to the animal to be benefited. Hence, the anion of the acid addition salt will be by definition relatively innocuous to the treated animal at the therapeutic dosage administered. The beneficial action of the analgesic will not be vitiated by side-effects ascribable to an inherently toxic anion.

Appropriate acid addition salts include those prepared from suitable mineral acids, e.g., hydrochloric, hydrobromic, hydroiodic, nitric, sulfuric, and phosphoric acids; and those prepared from organic acids, e.g., acetic, propionic, butyric, citric, lactic, benzoic, palmitic, succinic, gluconic, mucic, tartaric, pamoic, salicylic, cyclohexylsulfamic, and p-toluenesulfonic acid. On occasion the compounds or their acid addition salts in their crystalline state are isolated as solvates, e.g., with a discreet quantity of solvent, e.g., water, ethyl acetate, and the like, associated physically, and thus removable without effective alteration of the chemical entity per se.

Reference to Example 1 of this description of the invention reveals a relatively involved multi-step procedure for making the new 4-amino-4-arylcyclohexanones and ketals of Formula I. This original procedure consists of eight separate chemical conversions. Each step will be generally described hereinbelow and the details are available in the various Examples.

The synthesis begins with preparation of a dialkyl 4-cyano-4-arylpimelate via a Michael-type condensation involving an arylacetonitrile and methyl acrylate. A solvent medium, e.g., tert-butyl alcohol, is employed and a basic catalyst, for example, 40% methanolic tetramethylammonium hydroxide (Triton B ®). The reaction mixture is heated at the reflux temperature for several hours, and the desired dialkyl 4-cyano-4-arylpimelate first intermediate thus formed is recovered by conventional techniques such as solvent extraction and distillation.

The second intermediate, an alkyl 5-cyano-2-oxo-5-arylcyclohexanecarboxylate, is prepared by heating a dialkyl 4-cyano-4-arylpimelate from Step 1 in the presence of a strong base, e.g., an alkali metal, sodium hydride or potassium tert-butoxide. An organic solvent medium such as toluene or tetrahydrofuran is suitable and the desired intermediate is recovered by conventional techniques of solvent extraction and distillation. These intermediates can be named as 2-carbalkoxy-4-cyano-4-arylcyclohexanones as related in the Examples.

The third intermediate, a 4-cyano-4-arylcyclohexanone is prepared by a conventional hydrolysis and decarboxylation of the second intermediate alkyl 5-cyano-2-oxo-5-arylcyclohexanecarboxylate. The desired degradation is accomplished with a strong mineral acid such as sulfuric acid. Aqueous acetic acid is an appropriate and convenient solvent medium for heating at the reflux temperature. The desired intermediate is recovered by solvent extraction followed by removal of the solvent, and purification, for example by recrystallization.

In the next step of the synthesis, the carbonyl function of the 4-cyano-4-arylcyclohexanone is protected by conversion to a ketal. Any alkylene ketal is suitable, but an ethylene ketal readily obtainable with an ethylene glycol in the presence of an acid catalyst such as p-toluenesulfonic acid and an organic solvent medium is preferred in the process embodiment. The ketalization reaction is promoted by heating, conveniently at the reflux temperature and by azeotropic removal of the water formed. Ketals other than ethylene ketal are obtained using, e.g., 1,3-dihydroxypropane. The alkylene chains constituting the ketal function can be substituted with non-interfering hydrocarbon groups such as lower-alkyl, phenyl, lower 2-alkenyl. These ketal intermediates are recovered with appropriate organic solvents such as benzene and purified by conventional techniques.

Having protected the carbonyl function of the cyclohexanone, the 4-cyano group is converted to a carboxylic group (saponification). This is readily accomplished by heating the fourth intermediate, above, a 4-cyano-4-arylcyclohexanone, alkylene ketal, with an alkali metal hydroxide (preferably potassium hydroxide) in the presence of a relatively high boiling solvent such as ethylene glycol, followed by neutralization of the reaction mixture in with a mineral acid, e.g., hydrochloric acid. The thus produced 4-carboxy-substituted fifth intermediate is readily recovered and purified by solvent extraction, physical removal of the solvent, and recrystallization. It is preferable that prior to saponification of the 4-cyano-4-arylcyclohexanone ethylene ketal wherein the aryl is substituted by hydroxy, the hydroxy group is protected by a readily removable group, e.g., benzyl. Introduction of the protective group can be accomplished by standard methods, using benzyl halide, e.g., benzyl chloride, and base, e.g., sodium hydride.

The sixth intermediate, which is a 4-isocyanato-4-arylcyclohexanone, alkylene ketal, is prepared by a modified Curtius rearrangement utilizing an azide, (e.g., diphenyl phosphonic azide ($C_6H_5O)_2PON_3$) in a modification of the procedure described by T. Shioiri, K. Ninemiya and S. Yamada, J. Amer. Chem. Soc., 94, 6203, (1972). Use of an aprotic solvent medium, e.g., anisole, is preferred. The reaction mixture is heated at about 100° C. but reaction can start to occur at lower temperatures with the evolution of nitrogen. The desired isocyanate is recovered by removing volatile components, and then chromatographic procedures followed by, if necessary, recrystallization.

The next step in the synthesis provides a 4-methylamino embodiment of the invention according to Formula I wherein X is an alkylene ketal. This step involves reduction of the isocyanate group; chemical reduction agents, e.g., lithium aluminum hydride, can be used. The reaction is conventional and is promoted by heating. The desired product is obtained treating the reaction mixture with an alkali metal hydroxide so as to obtain the inorganic aluminum salts as gelatinous precipitate which is removed by filtration. Evaporation of the filtrate gives the amine which is purified by conventional methods. Alternatively the isocyanate may be reduced by catalytic hydrogenation.

Another embodiment of the invention, the disubstituted amino subject matter according to Formula I, are obtained by adding an $R_2$ group as defined onto the already described methylamino group. Alkylations, acylations, and reduction of acyl functions and the like are accomplished by usual methods.

Alkylations with allyl halide, e.g., allyl bromide, or β-haloester, e.g., ethyl bromoacetate in polar aprotic solvent, e.g., dimethylformamide, in the presence of inorganic base, e.g., potassium carbonate proceed as described in the literature. When converting the secondary amine to the tertiary amine form, it is necessary to first protect the hydroxy moiety (if it is present) by an easily removable protecting group such as benzyl.

Preferred acylating agents are acyl chlorides (e.g., cyclopropanecarbonyl chloride, butyryl chloride) and anhydrides of monobasic carboxylic acids (e.g., acetic anhydride and the like).

Addition of R₃ to the 2-position of 4-aryl-4-aminocyclohexanone is effected by reaction of equivalent amounts of the subject cyclohexanone and a strong base, e.g., lithium diisopropylamide, at low temperature, e.g., −10° to −40° C. in an inert solvent, e.g., tetrahydrofuran, followed by reaction with the desired alkyl (R₃) halide, e.g., methyl iodide, n-propyl bromide and the like. Isolation of the product is made using conventional procedures such as washing, chromatography, and recrystallization.

Stereochemistry of the R₃ substituent in reference to the 4-amino functionality is not exclusive; both the cis (Z) or trans (E) isomers are formed; the cis isomer has been observed to form predominantly, Preferential conformation with the phenyl group in an axial position of the cyclohexane ring was found in an x-ray study of geminally-substituted cyclohexanes (e.g., 1-acetoxy-4-phenyl-4-acetoxymethylcyclohexane) as described in D. Lednicer and D. J. DuChamp, J. Org. Chem., 39, 2311 (1974).

Reduction of the amide group resulting from acylation can be accomplished by usual literature methods, e.g., using diborane or lithium aluminum hydride in appropriate solvents.

Removal of the protecting group from a benzyloxy substituted phenyl ring is effected by hydrogenolysis under mild conditions over noble metal catalyst, e.g., palladium on carbon, in solvent which may contain mineral acid, e.g., hydrochloric acid. The method is standard in the art.

When a 4-amino-4-arylcyclohexanone, according to Formula I and the invention, is desired, the ketal is removed by prolonged action of an aqueous mineral acid such as hydrochloric acid in the presence of methanol as a solvent. "Prolonged action" means as much as 48 hours' time.

If an unsubstituted amino nitrogen is desired, the best way to accomplish such objective is to heat the 4-isocyanato intermediate with an alkali metal hydroxide particularly sodium hydroxide in the presence of ethylene glycol at the reflux temperature followed by brief treatment with acid. When a lower boiling solvent such as methanol was used as the solvent medium, a dimeric urea instead of the primary amine was obtained.

During the course of developing this invention an improved process of synthesis was discovered. It has been found that many of the compounds of this invention can be readily prepared by a Grignard reaction between a phenyl Grignard reagent of the kind

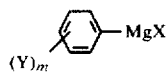

and a 4-dialkylamino-4-cyanocyclohexanone, ketal. In the foregoing Formula the Y and m variables are as heretofore defined, except that Y cannot be the unprotected hydroxy nor the alkanoyloxy functionalities.

This process can also be used to prepare the 4-dialkylamino-4-hydroxy-substitutedphenylcyclohexanone ketals if the hydroxy function is protected by a protecting group, e.g., tetrahydropyranyl, which can be removed under mild hydrolytic conditions using aqueous acid, e.g., hydrochloric, acetic, and the like.

The basis for the new synthesis was provided by the teachings of Hauser, C. R. and D. Lednicer, J. Org. Chem. 24, p. 46 (1959) and Lednicer, D., and J. C. Babcock, J. Org. Chem. 27, p. 2541 (1962). These authors showed that the nitrile group of an α-amino nitrile is displaced by the organometallic reagent so that a different result obtains than that taught by Whitmore, Frank C., Organic Chemistry, at pp. 852-854 and p. 416 (published by D. VanNostrand Co., Inc., New York, 1951) where a Grignard reagent adds to nitriles to produce imines. In this new and improved process of this invention, the phenyl ring attaches directly to the 4-carbon of the cyclohexanone ring to which same carbon the amino group is attached.

The indicated reaction takes place when the selected Grignard reagent is heated at the reflux temperature in an organic solvent medium in the presence of a 4-amino-4-cyanocyclohexanone, ketal. A suitable organic solvent medium is tetrahydrofuran, and it is preferable that it be anhydrous. Prolonged heating might be necessary; those nitrile displacements already successfully completed have required from 18 hours to three days. In most cases, 15 to 24 hours would appear to be adequate reaction time.

The desired 4-dialkylamino-4-phenylcyclohexanone, ketals are recovered in the usual way by decomposition of the reaction mixture with aqueous ammonium chloride. The organic layer is recovered and further purification techniques are applied such as solvent evaporation, washing, drying, chromatography, and recrystallization.

The 4-dialkylamino-4-cyanocyclohexanone, ketal antecedent compounds are obtained from 4-oxocyclohexanone, monoketals by reaction with an alkali metal cyanide, e.g., potassium cyanide, and an amine acid addition salt as described. This reaction proceeds readily and no heating is required. Room temperatures with stirring are suitable. Recovery-purification methods are conventional.

The 4-oxocyclohexanone, monoketals are prepared by methods known in the art, e.g., as described by M. Haslanger and R. G. Lawton, Synthetic Commun., 4, 155 (1974).

The foregoing improved method of synthesis provides shorter synthesis to some compounds of the invention. Illustratively the 4-(meta-hydroxyphenyl)-4-dimethylaminocyclohexanone, and 4-(m-hydroxy)-4-(n-butylmethylamino)cyclohexanone ketal compounds of the invention have been prepared and found to possess unexpected narcotic antagonist activity and, advantageously, low to moderate physical dependence liability as well as the analgesic activity observed with other compounds of the invention. It provides access to many compounds that would otherwise require the complicated and time-consuming multiple reaction steps of the original synthesis.

PREPARATION A p-tert-Butylphenylacetonitrile

A solution consisting of 4 ml. thionyl chloride and 10 ml. benzene is added to a solution consisting of 10.0 gm. (0.061 mole) p-tert-butylbenzyl alcohol and 85 ml. benzene. The reaction mixture is stirred at 25° C. for 30 min. and then heated at the reflux temperature for 4 hours. After cooling, the benzene is removed by evaporation under reduced pressure. The residue thus obtained is distilled at 0.05 mm Hg. pressure, and 10.14 gm. (92% yield) of benzyl chloride having a boiling range of 62° to 65° C. is obtained.

Some 9.64 gm. (0.053 mole) of this benzyl chloride is mixed with 10.13 gm. potassium cyanide, 0.10 gm. potassium iodide in 75 ml. water, and 150 ml. methanol and heated at the reflux temperature for one (1) hour. After removing the bulk of the methanol by evaporation under reduced pressure, the residue thus obtained is extracted with diethyl ether and the resulting ether solution is washed first with water and then with brine. The washed, ether solution is then concentrated by evaporation of the ether, and the oil thus obtained is distilled at 0.03 mm pressure. There is thus obtained 6.38 gm. (70% yield) of p-tert-butylphenylacetonitrile having a boiling range between 79° and 84° C.

Analysis: Cal'd. for $C_{12}H_{15}N$: C, 83.19; H, 8.73; N, 8.09. Found: C, 82.56; H, 8.68; N, 7.34.

EXAMPLE 1

Preparation of 4-(p-chlorophenyl)-4-dimethylaminocyclohexanone, ethylene ketal free base and the hydrochloride thereof.

Part A: Preparation of precursor, the Dimethyl diester of 4-(p-chlorophenyl)-4-cyanopimelic acid A mixture consisting of 25.0 gm. (0.165 mole) p-chlorophenylacetonitrile, 77 ml. methyl acrylate, and 80 ml. tert-butyl alcohol is heated to the reflux temperature. The source of heat is removed, and a mixture consisting of 25 ml. of 40 percent methanolic tetramethylammonium hydroxide (Triton B ®) and 37 ml. tert-butyl alcohol is quickly added. Heating at the reflux temperature is resumed and continued for four (4) hours. The reaction mixture is allowed to cool, and is then diluted with 300 ml. water and 100 ml. benzene. The organic solvent and aqueous phases that form are separated and the aqueous phase is discarded. The organic phase is washed successively with 2.5 N hydrochloric acid, water, and finally with brine. (The washed solution is then dried over $Na_2SO_4$). The organic solvent is removed by evaporation under reduced pressure, and the residue thus obtained is distilled under reduced pressure. The initial pressure is 40 mm mercury at which pressure any remaining methyl acrylate or other volatile components are eliminated. The final pressure is 0.35 mm mercury, and 38.06 gm. (71.4% yield) of the dimethyl ester of 4-(p-chlorophenyl)-4-cyanopimelic acid is obtained as an oil. The compound has a boiling point at 186° to 191° C.

Part B: Preparation of first intermediate, 2-Carbomethoxy-4-(p-chlorophenyl)-4-cyanocyclohexanone A reaction mixture consisting of 34.97 gm. (0.108 mole) dimethyl ester of 4-(p-chlorophenyl)-4-cyanopimelic acid, (prepared in Part A, above), dissolved in 700 ml. tetrahydrofuran with 24.4 gm. (0.218 mole) potassium tert-butoxide added is heated at the reflux temperature for 4½ hours. After cooling, the reaction mixture is chilled in an ice-bath and 175 ml. 2.5 N acetic acid is added. The organic and aqueous phases separate and the organic phase is recovered. It is diluted with 600 ml. benzene before being washed successively with aqueous sodium bicarbonate, water, and brine. The organic solvents are then removed by distillation under reduced pressure. There is thus obtained 30.2 gm. (96% yield) of 2-carbomethoxy-4-(p-chlorophenyl)-4-cyanocyclohexanone having a melting point at 139° to 143° C.

Analysis: Calc'd. for $C_{15}H_{14}ClNO_3$: C, 61.75; H, 4.84; N, 4.80. Found: C, 61.65; H, 5.02; N, 4.85.

Part C: Preparation of second intermediate 4-(p-Chlorophenyl)-4-cyanocyclohexanone A reaction mixture consisting of 29.8 gm. (0.102 mole) of 2-carbomethoxy-4-(p-chlorophenyl)-4-cyanocyclohexanone (prepared in Part B, above), 660 ml. glacial acetic acid, and 330 ml. 10% aqueous sulfuric acid is heated on a steam bath at about 100° C. for 24 hours. The mixture is stirred continuously. After cooling, the mixture is diluted with 1300 ml. water, and extracted with benzene. The benzene phase is recovered and washed successively with water, with aqueous sodium bicarbonate, and with brine. The benzene is then removed by evaporation under reduced pressure to give a solid residue. The solid residue is recrystallized from diethyl ether to give 12.13 gm. (82% yield) of 4-(p-chlorophenyl)-4-cyanocyclohexanone having a melting point at 94.5° to 97° C.

Analysis: Calc'd. for $C_{13}H_{12}ClNO$: C, 66.81; H, 5.18; N, 5.99. Found: C, 67.03; H, 5.16; N, 5.95.

Part D: Preparation of third intermediate, 4-(p-chlorophenyl)-4-cyanocyclohexanone, ethylene ketal A reaction mixture consisting of 19.49 gm. (0.084 mole) of 4-(p-chlorophenyl)-4-cyanocyclohexanone (prepared in Part C, above), 4.8 ml. (B 5.33 gm.) (0.086 mole) ethylene glycol, 0.21 gm. (1.1 mmole) p-toluenesulfonic acid, and 150 ml. benzene is heated at the reflux temperature in a reaction vessel equipped with a Dean and Stark trap for six (6) hours. The reaction solution is then allowed to cool before washing it successively with aqueous sodium bicarbonate, with water, and with brine. The washed solution is then taken to dryness by evaporation of the benzene. The solid residue thus obtained is crystallized from cyclohexane to give 21.87 gm. (79% yield) of 4-(p-chlorophenyl)-4-cyanocyclohexanone, ethylene ketal having a melting point at 124° to 126.5° C.

Analysis: Calc'd. for $C_{15}H_{16}ClNO_2$: C, 64.86; H, 5.81; N, 5.04. Found: C, 64.77; H, 5.81; N, 4.92.

Part E: Preparation of fourth intermediate, 4-Carboxy-4-(p-chlorophenyl)cyclohexanone, ethylene ketal A reaction mixture consisting of 21.87 gm. (0.079 mole) 4-(p-chlorophenyl)-4-cyanocyclohexanone, ethylene ketal (prepared in Part D, above), 22.0 gm. (0.39 mole) potassium hydroxide and 220 ml. ethylene glycol is heated at the reflux temperature for 16 hours. After cooling and diluting with water, the solutin is chilled in an ice-bath, layered with diethyl ether and cautiously acidified with concentrated hydrochloric acid. The ether layer is recovered and the acidified aqueous solution is extracted two more times with ether. The ether fractions are combined and washed with brine before removing the ether by evaporation. The residue thus obtained is recrystallized from a mixture of methylene chloride and technical hexane to give 19.26 gm. (82% yield) of 4-carboxy-4-(p-chlorophenyl)cyclohexanone, ethylene ketal having a melting point at 162.5° to 164.5° C.

Analysis: Calc'd. for $C_{15}H_{17}ClO_4$: C, 60.71; H, 5.78; Cl, 11.95. Found: C, 61.01; H, 5.77; Cl, 12.12.

Part F: Preparation of fifth intermediate 4-(p-Chlorophenyl)-4-isocyanatocyclohexanone, ethylene ketal To a mixture consisting of 15.79 gm. (0.0532 mole) 4-carboxy-4-(p-chlorophenyl)cyclohexanone, ethylene ketal (prepared in Part E, above) 7.4 ml. (5.36 gm., 0.0532 mole) triethylamine, and 135 ml. anisole is added 14.7 gm. (0.053 mole) diphenylphosphoric azide. This reaction mixture is then heated at 90° to 100° C. in an oil bath for two (2) hours. The volatile components are then removed by evaporation under reduced pressure, and the gummy residue thus obtained is chromatographed on a 1500 ml. column of silica gel. The column is eluted with a mixture of ethyl-acetate and technical hexanes (in proportion of 1:9) and 400-ml. fractions are collected. After combining fractions 14 through 29 and removing the solvents by evaporation under reduced pressure, there is obtained 7.75 gm. of crude product. Recrystallization from petroleum ether gives 6.72 gm. (43% yield) of 4-(p-chlorophenyl)-4-isocyanatocyclohexanone, ethylene ketal having a melting point at 76.5° to 80° C.

Analysis: Calc'd. for $C_{15}H_{16}ClNO_3$: C, 61.33; H, 5.49; N, 4.77. Found: C, 61.44; H, 5.50; N, 4.59.

Part G: Preparation of sixth intermediate, 4-(p-Chlorophenyl)-4-methylaminocyclohexanone, ethylene ketal A solution consisting of 6.62 gm. (0.0226 mole) 4-(p-chlorophenyl)-4-isocyanatocyclohexanone, ethylene ketal (prepared in Part F, above) in 50 ml. tetrahydrofuran is mixed with a suspension of 1.29 gm. (0.045 mole) lithium aluminum hydride in 20 ml. tetrahydrofuran and the resulting reaction mixture is heated at the reflux temperature for four (4) hours. After cooling, followed by chilling in an ice bath, 1.3 ml. water, 1.3 ml. 15% sodium hydroxide, and finally another 3.9 ml. water are added successively. A gelatinous precipitate forms which is collected on a filter. The filtrate is saved, and the volatile components are removed by evaporation under reduced pressure. The residue thus obtained is recrystallized from petroleum ether to give 5.78 gm. (91% yield) of 4-(p-chlorophenyl)-4-methylaminocyclohexanone, ethylene ketal that has a melting point at 63.5° to 66.5° C.

Analysis: Calc'd. for $C_{15}H_{20}ClNO_2$: C, 63.93; H, 7.15; N, 4.97. Found: C, 64.14; H, 7.32; N, 5.15.

Part H: Preparation of object compound, 4-(p-Chlorophenyl)-4-dimethylaminocyclohexanone, ethylene ketal free base and the Hydrochloride thereof A reaction solution consisting of 5.68 gm. (0.0201 mole) 4-(p-chlorophenyl)-4-methylaminocyclohexanone, ethylene ketal (prepared in Part G, above), 22 ml. 37 percent formalin (aqueous formaldehyde), and 75 ml. methanol is heated at the reflux temperature for four (4) hours, after which heating the solution is allowed to cool and then chilled in an ice-bath. Small portions of sodium borohydride are cautiously added with stirring to a total of 2.89 gm. (0.076 mole). Stirring is continued for two (2) hours at 25° C. when the solution is concentrated by removing most of the solvent under reduced pressure. The concentrate is diluted with a mixture of 100 ml. methylene chloride and 20 ml. water. The aqueous phase that separates is discarded, and the organic phase is washed successively with water and then with brine. The methylene chloride solvent is then removed by evaporation under reduced pressure. The residue thus obtained is dissolved in the formalin and methanol as initially, heated at the reflux temperature, cooled in an ice bath, and treated again with the sodium borohydride as previously. Following the same work-up as described, the crude 4-(p-chlorophenyl)-4-dimethylaminocyclohexanone, ethylene ketal free base obtained following the removal of the methylene chloride is dissolved in a small amount of diethyl ether, and the ether solution is treated with 3 N hydrogen chloride in ether. A precipitate forms which is recrystallized from methylene chloride and ethyl acetate to give 3.96 gm. (59% yield) of object compound 4-(p-chlorophenyl)-4-dimethylaminocyclohexanone, ethylene ketal hydrochloride having a melting point at 261° to 262° C. (with decomposition).

Analysis: Calc'd. for $C_{16}H_{23}Cl_2NO_2$: C, 57.83; H, 6.98; N, 4.27. Found: C, 58.10; H, 7.01; N, 4.41.

EXAMPLE 2

Preparation of an object compound 4-(p-Chlorophenyl)-4-dimethylaminocyclohexanone A reaction solution consisting of 4.52 gm. (0.0136 mole) of 4-(p-chlorophenyl)-4-dimethylaminocyclohexanone, ethylene ketal hydrochloride (prepared in Example 1, Part H, above), 22.5 ml. 2.5 N hydrochloric acid, and 45 ml. methanol is set aside at 25° C. for 48 hours. The methanol medium is substantially removed by evaporation under reduced pressure to give a concentrate that is made strongly basic by additions of 50% aqueous sodium hydroxide. A precipitate forms which is collected on a filter and dissolved in diethyl ether. This ether solution is washed with brine to remove the residual water and the ether is then removed by evaporation under reduced pressure. The residue thus obtained is recrystallized from diethyl ether to give 2.30 gm. (70% yield) of 4-(p-chlorophenyl)-4-dimethylaminocyclohexanone having a melting point at 108° to 111° C.

Analysis: Calc'd. for $C_{14}H_{18}ClNO$: C, 66.79; H, 7.21; N, 5.57. Found: C, 67.10; H, 7.36; N, 5.42.

EXAMPLE 3

Preparation of 4-(p-Fluorophenyl)-4-dimethylaminocyclohexanone, ethylene ketal free base

Part A: Preparation of precursor, the Dimethyl diester of 4-cyano-4-(p-fluorophenyl)pimelic acid A reaction mixture consisting of 25.0 gm. (0.0185 mole) of p-fluorophenyl acetonitrile, 86 ml. methyl acrylate, and 90 ml. tert-butyl alcohol is heated to the reflux temperature. The source of heat is then removed and a mixture consisting of 28.1 ml. of 40% methanolic tetramethylammonium hydroxide (Tribon B ®) and 43 ml. tert-butyl alcohol is quickly added. Heating at the reflux temperature is resumed and continued for four (4) hours. The reaction mixture is allowed to cool and is then diluted with a mixture of 300 ml. water and 100 ml. benzene. When the organic aqueous phases forms, the aqueous phase is discarded and the organic (benzene) phase is saved. It is washed successively with 2.5 N hydrochloric acid, water, and finally with brine. The benzene is then removed by evaporation under reduced pressure, and the residue thus obtained is distilled under reduced pressure in order to removed any low-boiling by-products. The initial pressure is at 40 mm mercury, and the final pressure is at 0.25 mm mercury. There is thus obtained 50.99 gm. (72% yield) of the dimethyl ester of 4-cyano-4-(p-fluorophenyl)pimelic acid as an oil. Its boiling point is 179° to 181° C.

Part B: Preparation of first intermediate, 2-carbomethoxy-4-cyano-4-(p-fluorophenyl)cyclohexanone To a solution consisting of 42.71 gm. (0.139 mole) of the dimethyl ester of 4-(p-fluorophenyl)-4-cyanopimelic acid (prepared in Part A, above) and 900 ml. tetrahydrofuran is added 31.3 gm. (0.28 mole) potassium tert-butoxide. This reaction mixture is heated at the reflux temperature for four and one half (4½) hours. It is allowed to cool. It is then chilled in ice and 225 ml. of 2.5 N aqueous acetic acid is added. The organic layer that forms is recovered and diluted with 750 ml. benzene. The benzene:tetrahydrofuran solution is washed successively with sodium bicarbonate, with water, and finally with brine. The solvents are then removed by evaporation under reduced pressure to give 35.6 gm. (93% yield) of 2-carbomethoxy-4-cyano-4-(p-fluorophenyl)-cyclohexanone as a gum.

Part C: Preparation of second intermediate, 4-Cyano-4-(p-fluorophenyl)cyclohexanone A reaction mixture consisting of 33.9 gm. (0.123 mole) of 2-carbomethoxy-4-cyano-4-(p-fluorophenyl)-cyclohexanone (prepared in Part B, above), 900 ml. glacial acetic acid, and 450 ml. 10% aqueous sulfuric acid is heated with stirring on a steam bath for twenty-four (24) hours. After allowing the reaction mixture to cool, it is diluted with 2000 ml. water and extracted thoroughly with benzene. The benzene extracts are combined and washed successively with water, with aqueous sodium bicarbonate, and finally with brine. The benzene is then removed by evaporation under reduced pressure, and the solid residue thus obtained is recrystallized from diethyl ether to afford 16.23 gm. (67% yield) of 4-cyano-4-(p-fluorophenyl)cyclohexanone having a melting point at 84° to 88° C.

Analysis: Calc'd. for $C_{13}H_{12}FNO$: C, 71.87; H, 5.57; N, 6.45. Found: C, 71.64; H, 5.65; N, 6.30.

Part D: Preparation of third intermediate, 4-Cyano-4-(p-fluorophenyl)cyclohexanone, ethylene ketal A reaction mixture consisting of 16.23 gm. (0.075 mole) of 4-cyano-4-(p-fluorophenyl)cyclohexanone (prepared in Part C, above), 6 ml. ethylene glycol, 0.6 gm. p-toluenesulfonic acid, and 250 ml. benzene is heated at the reflux temperature in a reaction vessel fitted with a Dean and Stark trap for six (6) hours. The reaction solution is allowed to cool and then is washed successively with aqueous sodium bicarbonate, with water, and finally with brine. The benzene and volatile components are then removed by evaporation under reduced pressure and the solid residue thus obtained is recrystallized from technical hexanes to give 18.17 gm. (94% yield) of 4-cyano-4-(p-fluorophenyl)cyclohexanone, ethylene ketal having a melting point at 91° to 93.5° C.

Analysis: Calc'd. for $C_{15}H_{16}FNO_2$: C, 68.95; H, 6.17; N, 5.36. Found: C, 68.41; H, 6.05; N, 5.35.

Part E: Preparation of fourth intermediate, 4-Carboxy-4-(p-fluorophenyl)cyclohexanone, ethylene ketal A reaction mixture consisting of 18.17 gm. (0.070 mole) of 4-cyano-4-(p-fluorophenyl)cyclohexanone, ethylene ketal (prepared in Part D, above), 15.0 gm. (0.38 mole) sodium hydroxide, and 150 ml. ethylene glycol is heated at the reflux temperature for about sixteen (16) hours before it is allowed to cool, and is then diluted with water. The aqueous solution is then chilled in an ice-bath and layered with diethyl ether. The aqueous phase is cautiously acidified with concentrated hydrochloric acid. The ether layer is separated, and the aqueous layer is extracted two times with diethyl ether. The original ether layer and ether extracts are combined, washed once with brine, and the ether is removed by evaporation under reduced pressure. There is thus obtained 18.2 gm. (93% yield) of 4-carboxy-4-(p-fluorophenyl)cyclohexanone, ethylene ketal as a solid that cannot be recrystallized satisfactorily (melting range 117° to 122° C.).

Part F: Preparation of fifth intermediate, 4-(p-fluorophenyl)-4-isocyanatocyclohexanone, ethylene ketal To a suspension consisting of 24.5 gm. (0.0875 mole) of 4-carboxy-4-(p-fluorophenyl)cyclohexanone, ethylene ketal (prepared in Part E, above), 12.1 ml. (8.8 gm., 0.087 mole) of triethylamine, and 220 ml. anisole there is added 24.1 gm. diphenylphosphonic azide. This reaction mixture is then heated at 90° at 100° C. with stirring in an oil bath for two (2) hours. The reaction medium and other volatile components are removed by evaporation under reduced pressure. The gummy residue thus obtained is chromatographed on a 1000 ml. column of silica gel. Elution was effected with a solvent system consisting of 1 percent ethyl acetate in methylene chloride.

The appropriate fractions are combined, and the solvents are removed by evaporation under reduced pressure to give 8.49 gm. of 4-(p-fluorophenyl)-4-isocyanatocyclohexanone, ethylene ketal that has the qualities of a gum.

Part G: Preparation of sixth intermediate, 4-(fluorophenyl)-4-methylaminocyclohexanone, ethylene ketal free base and hydrochloride thereof A solution consisting of 10.11 gm. (0.0365 mole) of 4-(p-fluorophenyl)-4-isocyanatocyclohexanone, ethylene ketal (prepared in Part F, above) and 80 ml. tetrahydrofuran is added to a suspension consisting of 2.08 gm. (0.055 mole) lithium aluminum hydride and 30 ml. tetrahydrofuran, and this reaction mixture is heated at the reflux temperature with stirring for four (4) hours. The mixture is allowed to cool, and is then chilled in an icebath. To the chilled mixture is added in sequence: 2.1 ml. water, 2.1 ml. 15% aqueous sodium hydroxide, and another 6.3 ml. water. A gelatinous material is obtained that is removed by filtration. The filtrate is recovered and evaporated to dryness. The residue thus obtained is dissolved in a small amount of diethyl ether and enough 3 N hydrogen chloride in diethyl ether is added to precipitate all of the amine free base as the hydrochloride acid addition salt. The precipitate is collected on a filter and recrystallized from a mixture of methylene chloride and ethyl acetate to give 9.34 gm. (56% yield) of 4-(p-fluorophenyl)-4-methylaminocyclohexanone, ethylene ketal hydrochloride having a melting point at 262.5° to 263.5° C. (with decomposition).

Analysis: Calc'd. for $C_{15}H_{21}ClFNO_2$: C, 59.69; H, 7.01; N, 4.64. Found: C, 59.27; H, 7.21; N, 4.60.

Part H: Preparation of object compound, 4(p-Fluorophenyl)-4-dimethylaminocyclohexanone, ethylene ketal free base A solution consisting of the free base from 9.24 gm. (0.0307 mole) of 4-(p-fluorophenyl)-4-methylaminocyclohexanone, ethylene ketal hydrochloride (prepared in Part G, above), 33 ml. of 37% formalin, and 110 ml. methanol is heated at the reflux temperature for four (4) hours. The mixture is allowed to cool before chilling in an ice-bath and slowly adding small portions of sodium borohydride until a total of 4.4 gm. (0.115 mole) has been added. Stirring is continued for two (2) hours at about 25° C. A substantial part of the volatile liquid components, i.e., solvents is removed by evaporation under reduced pressure, and the concentrate thus obtained is diluted with 200 ml. methylene chloride and 50 ml. water. When the organic and aqueous phases have stabilized, the organic phase is recovered, washed with water and washed with brine. After removing the methylene chloride solvent, the residue thus obtained is again reacted with sodium borohydride and worked up as described immediately above. This time the residue from removal of the methylene chloride solvent is recrystallized from petroleum ether to give 7.29 gm. (89% yeild) of 4-(p-fluorophenyl)-4-dimethylaminocyclohexanone, ethylene ketal having a melting point at 79.5° to 82° C.

Analysis: Calc'd. for $C_{16}H_{22}FNO_2$: C, 68.79; H, 7.94; N, 5.02. Found: C, 69.16; H, 7.70; N, 4.91.

Example 4

Preparation of an object compound of 4-(p-Fluorophenyl)-4-dimethylaminocyclohexanone A solution consisting of 6.29 gm. (0.0226 mole) of 4-(p-fluorophenyl)-4-dimethylaminocyclohexanone, ethylene ketal (prepared in Example 3, Part H), 32 ml. of 2.5 N hydrochloric acid, and 64 ml. methanol is set aside at 25° C. for 48 hours. A substantial part of the methanol is then removed by evaporation under reduced pressure, and the concentrate is made strongly basic with 50% sodium hydroxide. A precipitate forms which is collected on a filter and dissolved in diethyl ether. The ether solution is washed with water and finally with brine before removing the ether by evaporation under reduced pressure. The residue thus obtained is recrystallized from diethyl ether to give 3.97 gm. (75% yield) of 4-(p-fluorophenyl)-4-dimethylaminocyclohexanone having a melting point at 126° to 128° C.

Analysis: Calc'd. for $C_{14}H_{18}FNO$: C, 71.46; H, 7.71; N, 5.95. Found: C, 71.45; H, 7.86; N, 5.83.

EXAMPLE 5

Preparation of 4-(3,4-dimethoxyphenyl)-4-dimethylaminocyclohexanone, ethylene ketal free base Part A: Preparation of precursor, the dimethyl ester of 4-cyano-4-(3,4-dimethoxyphenyl)pimelic acid Following the procedure of Example 1, Part A, but substituting 25.0 gm. (0.141 mole) 3,4-dimethoxyphenyl acetonitrile, 66 ml. methyl acrylate, and 70 ml. tert-butyl alcohol for the 25.0 gm. p-chlorophenyl acetonitrile, the 77 ml. methyl acrylate, and the 80 ml. tert-butyl alcohol, using 21.5 ml. of the 40% methanolic tetramethylammonium hydroxide, and 32 ml. of the tert-butyl alcohol, and final distillation at 0.20 mm pressure, there is prepared 32.22 gm. (65% yield) of the dimethyl ester of 4-cyano-4-(3,4-dimethoxyphenyl)pimelic acid as an oil having a boiling range of 210° to 214° C.

Part B: Preparation of first intermediate, 2-Carbomethoxy-4-cyano-4-(3,4-dimethoxyphenyl)-cyclohexanone Following the procedure of Example 1, Part B, but substituting 34.25 gm. (0.098 mole) of the dimethyl ester of 4-cyano-4-(3,4-dimethoxyphenyl)pimelic acid (prepared in Part A, above) for the dimethyl ester of 4-(p-chlorophenyl)-4-cyanopimelic acid and using 640 ml. of the tetrahydrofuran, 22.0 gm. (0.196 mole) of the potassium tert-butoxide and 155 ml. of the 2.5 N of the aqueous acetic acid instead of the 700 ml. the 24.4 gm. (0.218 mole), and the 175 ml. respectively, there is prepared 29.2 gm. (94% yield) of 2-carbomethoxy-4-cyano-4-(3,4-dimethoxyphenyl)cyclohexanone as crystals having a melting range of 110° to 113° C. An analytical sample recrystallized from a mixture of ethyl acetate and cyclohexane melts in the range of 112.5° to 114.5° C.

Analysis: Calc'd. for $C_{15}H_{17}NO_3$: C, 69.48; H, 6.61; N, 5.40. Found: C, 69.73; H, 6.64; N, 5.16.

Part C: Preparation of second intermediate, 4-Cyano-4-(3,4-dimethoxyphenyl)cyclohexanone Following the same procedure described in Example 1, Part C, but substituting 29.0 gm. (0.0915 mole) of 2-carbomethoxy-4-(3,4-dimethoxyphenyl)-4-cyanocyclohexanone (prepared in Part B, above) for the 29.8 gm. of 2-carbomethoxy-4-(p-chlorophenyl)-4-cyanocyclohexanone, using 600 ml. acetic acid and 300 ml. 10 percent aqueous sulfuric acid instead of the 660 ml. and 330 ml., respectively, heating on the steam bath for 48 hours instead of 24 hours, and recrystallizing from a mixture of ethyl acetate and hexane instead of diethyl ether, there is obtained 16.83 gm. (67% yield) of the desired 4-cyano-4-(3,4-dimethoxyphenyl)cyclohexanone which has a melting point at 112.5° to 114.5° C.

Analysis: Calc'd. for $C_{15}H_{17}NO_3$: C, 69.48; H, 6.61; N, 5.40. Found: C, 69.73; H, 6.64; N, 5.16.

Part D: Preparation of third intermediate, 4-Cyano(3,4-dimethoxyphenyl)cyclohexanone, ethylene ketal Following the procedure of Example 1, Part D, but substituting 15.96 gm. (0.0616 mole) of 4-cyano-4-(3,4-dimethoxyphenyl)cyclohexanone (prepared in Part C, above) for the 19.49 gm. of 4-(p-chlorophenyl)-4-cyanocyclohexanone; using 3.6 ml. ethylene glycol, 0.16 gm. p-toluene-sulfonic acid, and 110 ml. benzene instead of the 4.8 ml., 0.21 gm., and 150 ml., respectively and recrystallizing from diethyl ether instead of the cyclohexane there is obtained 16.85 gm. (90% yield) of 4-cyano-4-(3,4-dimethoxyphenyl)cyclohexanone, ethylene ketal having a melting range at 93.5° to 96.5° C.

Analysis: Calc'd. for $C_{17}H_{21}NO_4$: C, 67.31; H, 6.98; N, 4.62. Found: C, 67.29; H, 7.01; N, 4.44.

Part E: Preparation of fourth intermediate, 4-Carboxy-4-(3,4-dimethoxyphenyl)cyclohexanone, ethylene ketal Following the procedure of Example 1, Part E, but substituting 17.54 gm. (0.058 mole) of 4-cyano-4-(3,4-dimethoxyphenyl)cyclohexanone, ethylene ketal (prepared in Part D, above) for the 21.87 gm. of 4-(p-chlorophenyl)-4-cyanocyclohexanone, ethylene ketal; and using 17.5 gm. (0.31 mole) potassium hydroxide and 175 ml. ethylene glycol instead of the 22.0 gm. and 220 ml., respectively; there is obtained, after removal of the ether, 19.0 gm. (99% yield) of 4-carboxy-4-(3,4-dimethoxyphenyl)cyclohexanone, ethylene ketal as a gum that gives a reasonably expected infrared spectrum.

Part F: Preparation of fifth intermediate, 4-Isocyanato-4-(3,4-dimethoxyphenyl)cyclohexanone, ethylene ketal Following the procedure of Example 1, Part F, but substituting 22.9 gm. (0.0710 mole) of 4-carboxy-4-(3,4-dimethoxyphenyl)cyclohexanone, ethylene ketal (prepared in Part E, above) for the 15.79 gm. of 4-carboxy-4-(p-chlorophenyl)cyclohexanone, ethylene ketal, and using 10.0 ml. (7.26 gm., 0.073 mole) triethylamine, 215 ml. anisole, and 19.7 gm. diphenylphosphonic azide instead of the 7.4 ml., the 135 ml., and the 14.7 gm., respectively, there is obtained after chromatographing on a 2000 ml. column of silica gel and elution with 30 percent ethyl acetate in technical hexane 6.44 gm. (28% yield) of 4-isocyanato-4-(3,4-dimethoxyphenyl)cyclohexanone, ethylene ketal as a waxy solid.

Part G: Preparation of sixth intermediate, 4-(3,4-Dimethoxyphenyl)-4-methylaminocyclohexanone, ethylene ketal hydroiodide Following the procedure of Example 1, Part G, but substituting 6.44 gm. (0.020 mole) of 4-isocyanato-4-(3,4-dimethoxyphenyl)cyclohexanone, ethylene ketal (prepared in Part F, above) for the 6.62 gm. of 4-(p-chlorophenyl)-4-isocyanatocyclohexanone, using 95 ml. tetrahydrofuran and a suspension of 1.16 gm. (0.031 mole) lithium aluminum hydride in 11 ml. tetrahydrofuran instead of the 50 ml., the 1.29 gm., and 20 ml., respectively, and adding 1.2 ml. water, 1.2 ml. of 15 percent sodium hydroxide, and 3.6 ml. water instead of the 1.3 ml., 1.3 ml., and 3.9 ml., respectively, there is obtained a residue from the filtrate that is chromatographed on a 600 ml. column of silica gel using ammonium hydroxide (NH4OH)-saturated methylene chloride as solvent. After collecting and combining the appropriate fractions and removing the solvent by evaporation under reduced pressure, the residue is dissolved in methylene chloride. This solution is acidified with 10% aqueous hydriodic acid and the solvents are removed by evaporation under reduced pressure. There is thus obtained after recrystallization from a mixture of methylene chloride and diethyl ether 5.0 gm. (57% yield) of 4-(3,4-dimethoxyphenyl)-4-methylaminocyclohexanone, ethylene ketal hydroiodide having a melting point at 200.5° to 201.5° C.

Analysis: Calc'd. for $C_{17}H_{26}INO_4$: C, 46.90; H, 6.02; N, 3.22. Found: C, 46.82; H, 6.06; N, 3.27.

Part H: Preparation of object compound, 4-(3,4-dimethoxyphenyl)-4-dimethylaminocyclohexanone, ethylene ketal Following the procedure of Example 1, Part H, but substituting the free base from 5.0 gm. (0.0155 mole) of 4-(3,4-dimethoxyphenyl)-4-methylaminocyclohexanone, ethylene ketal hydroiodide (prepared in Part G, above) for the 5.68 gm. of 4-(p-chlorophenyl)-4-methylaminocyclohexanone, ethylene ketal, using 12.5 ml. 37 percent formalin and 43 ml. methanol instead of the 22 ml. and 75 ml., respectively, and using 1.65 gm. (0.043 mole) sodium borohydride instead of the 2.89 gm. there was obtained the desired free base which is recrystallized as such from technical hexane to give 3.40 gm. (92% yield) of 4-(3,4-dimethoxyphenyl)-4-dimethylaminocyclohexanone, ethylene ketal which has a melting range at 95° to 98.5° C.

Analysis: Calc'd. for $C_{18}H_{27}NO_4$: C, 67.26; H, 8.47; N, 4.36. Found: C, 67.42; H, 8.65; N, 4.34.

EXAMPLE 6

Preparation of an object compound, 4-(3,4-Dimethoxyphenyl)-4-dimethylaminocyclohexanone free base Following the procedure of Example 2, but substituting 2.4 gm. (0.0075 mole) of 4-(3,4-dimethoxyphenyl)-4-dimethylaminocyclohexanone, ethylene ketal free base (prepared in Example 5, Part H, above) for the 4-(p-chlorophenyl)-4-dimethylaminocyclohexanone, ethylene ketal hydrochloride, 12 ml. of 2.5 N hydrochloric acid for the 22.5 ml., and 24 ml. methanol for the 45 ml., there is prepared 1.48 gm. (71% yield) of 4-(3,4-dimethoxyphenyl)-4-dimethylaminocyclohexanone as the free base, having a melting point at 97° to 98.5° C.

Analysis: Calc'd. for $C_{16}H_{23}NO_3$: C, 69.28; H, 8.36; N, 5.05. Found: C, 69.14; H, 8.44; N, 5.07.

EXAMPLE 7

Preparation of 4-(p-Anisyl)-4-dimethylaminocyclohexanone, ethylene ketal free base and hydrochloride thereof

Part A: Preparation of precursor, the dimethyl ester of 4-cyano-4-(p-anisyl)pimelic acid Following the procedure of Example 1, Part A, but substituting 36.75 gm. (0.25 mole) p-anisyl acetonitrile, 116 ml. methyl acrylate, and 120 ml. tert-butyl alcohol for the 25.0 gm. p-chlorophenyl acetonitrile, the 77 ml. methyl acrylate, and the 80 ml. tert-butyl alcohol, and using 38 ml. of the 40% methanolic tetramethylammonium hydroxide and 56 ml. tert-butyl alcohol, followed by final distillation at 0.6 mm pressure, there is prepared 55.90 gm. (70% yield) of the dimethyl ester of 4-cyano-4-(p-anisyl)pimelic acid as an oil having a boiling range of 205° to 210° C.

Part B: Preparation of first intermediate, 2-Carbomethoxy-4-cyano-4-(p-anisyl)cyclohexanone Following the procedure of Example 1, Part B, but substituting 53.94 gm. (0.169 mole) of the dimethyl ester of 4-cyano-4-(p-anisyl)pimelic acid (prepared in Part A, above) for the dimethyl ester of 4-(p-chlorophenyl)-4-cyanopimelic acid and using 1100 ml. of the tetrahydrofuran, 38.0 ml. (0.34 mole) of the potassium tert-butoxide, and 270 ml. of the 2.5 N hydrochloric acid instead of the 700 ml., the 24.4 gm. (0.218 mole), and the 175 ml., respectively, there is prepared 46.2 gm. (95% yield) of 2-carbomethoxy-4-cyano-4-(p-anisyl)cyclohexanone as a gum.

Part C: Preparation of second intermediate, 4-Cyano-4-(p-anisyl)cyclohexanone

Following the procedure of Example 1, Part C, but substituting 41.5 gm. (0.145 mole) of 2-carbomethoxy-4-cyano-4-(p-methoxyphenyl)cyclohexanone [same as 2-carbomethoxy-4-cyano-4-(p-anisyl)cyclohexanone] (prepared in Part B, above) for the 29.8 gm. of 2-carbomethoxy-4-(p-chlorophenyl)-4-cyanocyclohexanone, using 940 ml. glacial acetic acid and 470 ml. 10 percent aqueous sulfuric acid instead of the 660 ml. and 330 ml. respectively, and heating for 48 hours instead of 24 hours there is obtained 23.6 gm. (71% yield) of the expected 4-cyano-4-(p-anisyl)cyclohexanone which compound has a melting range at 84° to 86.5° C. An analytical sample recrystallized from diethyl ether has a melting range at 77.5° to 79.5° C.

Analysis: Calc'd. for $C_{14}H_{15}NO_2$: C, 73.34; H, 6.59; N, 6.11. Found: C, 73.21; H, 6.65; N, 6.00.

Part D: Preparation of third intermediate, 4-Cyano-4-(p-anisyl)cyclohexanone, ethylene ketal Following the procedure of Example 1, Part D, but substituting 22.43 gm. (0.098 mole) of 4-cyano-4-(p-anisyl)cyclohexanone (prepared in Part C, above) for the 19.49 gm. of the 4-(p-chlorophenyl)-4-cyanocyclohexanone, and using 5.6 ml. (6.15 gm., 0.099 mole) ethylene glycol, 0.24 gm. p-toluenesulfonic acid, and 175 ml. benzene instead of the 4.8 ml., the 0.21 gm., and the 150 ml., respectively, there is obtained a residual solid that upon recrystallization from a mixture of methylene chloride and technical hexane instead of from cyclohexane gives 24.66 gm. (93% yield) of the expected intermediate 4-cyano-4-(p-anisyl)cyclohexanone, ethylene ketal that has a melting range at 101° to 103.5° C.

Analysis: Calc'd. for $C_{16}H_{19}NO_3$: C, 70.31; H, 7.01; N, 5.13. Found: C, 70.20; H, 7.01; N, 5.02.

Part E: Preparation of fourth intermediate, 4-Carboxy-4-(p-anisyl)cyclohexanone, ethylene ketal Following the procedure of Example 1, Part E, but substituting 27.98 gm. (0.103 mole) of 4-cyano-4-(p-anisyl)cyclohexanone, ethylene ketal (prepared in Part D, above) for the 21.87 gm. of 4-(p-chlorophenyl)-4-cyanocyclohexanone, ethylene ketal, and using 28.0 gm. (0.50 mole) potassium hydroxide and 280 ml. ethylene glycol instead of the 22 gm. and 220 ml., respectively, there is obtained 22.35 gm. (83% yield) of 4-carboxy-4-(p-anisyl)cyclohexanone, ethylene ketal that has a melting point at 154° to 155.5° C.

Analysis: Calc'd. for $C_{16}H_{20}O_5$: C, 65.74; H, 6.90. Found: C, 65.42; H, 6.93.

Part F: Preparation of fifth intermediate, 4-Isocyanato-4-(p-anisyl)cyclohexanone, ethylene ketal Following the procedure of Example 1, Part F, but substituting 10.0 gm. (0.034 mole) of 4-carboxy-4-(p-anisyl)cyclohexanone, ethylene ketal (prepared in Part E, above) for the 15.79 gm. of 4-carboxy-4-(p-chlorophenyl)-4-cyanocyclohexanone, ethylene ketal, and using 4.75 ml. (3.46 gm., 0.034 mole) triethylamine, 100 ml. anisole, and 9.42 gm. diphenylphosphonic azide instead of the 7.4 ml., the 135 ml., and the 14.7 gm., respectively, there is obtained a residual gum that is chromatographed on a 1000 ml. column of silica gel instead of 1500 ml., and elution is effected with a solvent system consisting of 2.5 percent ethyl acetate in methylene chloride instead of the mixture of ethyl acetate and technical hexane. There is thus obtained, after removal of the solvents by evaporation, 6.42 gm. of crude product that upon recrystallization from technical hexane affords 6.11 gm. (62% yield) of 4-isocyanato-4-(p-anisyl)cyclohexanone, ethylene ketal melting at 70.5° to 72° C.

Analysis: Calc'd. for $C_{16}H_{19}NO_4$: C, 66.41; H, 6.62; N, 4.89. Found: C, 66.47; H, 6.61; N, 4.77.

Part G: Preparation of sixth intermediate 4-(p-anisyl)-4-methylaminocyclohexanone, ethylene ketal p-toluenesulfonate Following the procedure of Example 1, Part G, but substituting 6.11 gm. of 4-isocyanato-4-(p-anisyl)cyclohexanone, ethylene ketal (prepared in Part F, above) for the 6.62 gm. of 4-(p-chlorophenyl)-4-isocyanatocyclohexanone, ethylene ketal; using 80 ml. tetrahydrofuran and 1.22 gm. (0.032 mole) lithium aluminum hydride instead of the 50 ml. and the 1.29 gm., respectively; and then adding 1.22 ml. water, 1.22 ml. 15 percent aqueous sodium hydroxide, and 3.66 ml. water instead of the 1.3 ml., the 1.3 ml., and the 3.9 ml. respectively, there is obtained a residue from the filtrate that is dissolved in a small amount of ether. To the ether solution is added 4.0 gm. p-toluenesulfonic acid dissolved in ether. The acid addition salt that precipitates is collected on a filter and recrystallized from a solvent mixture of ethyl acetate and methylene chloride. There is thus obtained 8.30 gm. (88% yield) of the desired intermediate 4-(p-anisyl)-4-methylaminocyclohexanone, ethylene ketal p-toluenesulfonate that has a melting point at 206° to 208° C.

Analysis: Calc'd. for $C_{23}H_{31}NO_6S$: C, 61.44; H, 6.95; N, 3.12. Found: C, 61.27; H, 6.95; N, 3.06.

Part H: Preparation of object compound, 4-(p-anisyl)-4-dimethylaminocyclohexanone, ethylene ketal hydrochloride Following the procedure of Example 1, Part H, but substituting the free base obtained from 8.30 gm. (0.018 mole) of 4-(p-anisyl)-4-methylaminocyclohexanone, ethylene ketal p-toluenesulfonate (prepared in Part G, above) for the 5.68 gm. of the 4-(p-chlorophenyl)-4-methylaminocyclohexanone, ethylene ketal, and using 20 ml. 37 percent formalin, 60 ml. methanol, and 2.44 gm. sodium borohydride instead of the 22 ml., 75 ml., and 2.89 gm., respectively, there is finally obtained a precipitate of the hydrochloride acid addition salt that is recrystallized from a mixture of methylene chloride and ethyl acetate thus affording 4.61 gm. (78% yield) of the object compound 4-(p-anisyl)-4-dimethylaminocyclohexanone, ethylene ketal hydrochloride that has a melting point at 203° to 204° C.

Analysis: Calc'd. for $C_{17}H_{26}ClNO_3$: C, 62.28; H, 7.99; N, 4.27. Found: C, 62.41; H, 8.20; N, 4.14.

EXAMPLE 8

Preparation of an object compound, 4-(p-anisyl)-4-dimethylaminocyclohexanone free base Following the procedure of Example 2, but substituting 4.61 gm. (0.014 mole) of 4-(p-anisyl)-4-dimethylaminocyclohexanone, ethylene ketal hydrochloride (prepared in Example 7, Part H, above) for the 4-(p-chlorophenyl)-4-dimethylaminocyclohexanone, ethylene ketal hydrochloride, 18.0 ml. of 2.5 N hydrochloric acid for the 22.5 ml., and 36 ml. methanol for the 45 ml., there is prepared (after recrystallization from technical hexane instead of diethyl ether) 2.29 gm. (66% yield) of 4-(p-anisyl)-4-dimethylaminocyclohexanone as the free base having a melting point at 89° to 91° C.

Analysis: Calc'd. for $C_{15}H_{21}NO_2$: C, 72.84; H, 8.56; N, 5.66. Found: C, 73.18; H, 8.63; N, 5.55.

EXAMPLE 9

Preparation of
4-(o-chlorophenyl)-4-dimethylaminocyclohexanone, ethylene ketal hydroiodide Part A: Preparation of precursor, the Dimethyl ester of 4-(o-chlorophenyl)-4-cyanopimelic acid Following the procedure of Example 1, Part A, but substituting o-chlorophenyl acetonitrile for p-chlorophenyl acetonitrile and decreasing the final distillation pressure to 0.08 mm Hg. there is prepared 39.11 gm. (73% yield) of the dimethyl ester of 4-(o-chlorophenyl)-4-cyanopimelic acid as an oil having a boiling range of 170° to 183° C.

Part B: Preparation of first intermediate,
2-Carbomethoxy-4-cyano-4-(o-chlorophenyl)cyclohexanone Following the procedure of Example 1, Part B, but substituting 39.11 gm. (0.121 mole) dimethyl-4-(o-chlorophenyl)-4-cyanopimelate (prepared in Part A, above) for the dimethyl ester of 4-(p-chlorophenyl)-4-cyanopimelic acid, and using 780 ml. of the tetrahydrofuran, 27.4 gm. (0.24 mole) of the potassium tert-butoxide, and 195 ml. of the 2.5 N acetic acid instead of the 700 ml., the 24.4 gm. (0.218 mole), and the 175 ml., respectively, there is prepared 33.4 gm. (95% yield) of 2-carbomethoxy-4-cyano-4-(o-chlorophenyl)cyclohexanone as a crystalline solid having a melting range of 113° to 118° C.

Part C: Preparation of second intermediate,
4-(o-chlorophenyl)-4-cyanocyclohexanone Following the procedure of Example 1, Part C, but substituting 33.4 gm. (0.115 mole) of 2-carbomethoxy-4-(o-chlorophenyl)-4-cyanocyclohexanone (prepared in Part B, above) for the 29.8 gm. of the 2-carbomethoxy-4-(p-chlorophenyl)-4-cyanocyclohexanone, using 730 ml. glacial acetic acid and 365 ml. 10 percent aqueous sulfuric acid instead of the 660 ml. and 330 ml., respectively, and heating for 48 hours instead of 24 hours there is obtained a residual solid that is recrystallized from a mixture of methylene chloride and technical hexane thus affording 20.54 gm. (80% yield) of 4-(o-chlorophenyl)-4-cyanocyclohexanone having a melting point at 106° to 108° C.

Analysis: Calc'd. for $C_{13}H_{12}ClNO$: C, 66.81; H, 5.18; N, 5.99. Found: C, 66.45; H, 5.13; N, 5.86.

Part D: Preparation of third intermediate,
4-(o-chlorophenyl)-4-cyanocyclohexanone, ethylene ketal Following the procedure of Example 1, Part D, but substituting 20.54 gm. (0.092 mole) of 4-(o-chlorophenyl)-4-cyanocyclohexanone (prepared in Part C, above) for the 19.49 gm. of the 4-(p-chlorophenyl)-4-cyanocyclohexanone, and using 5.1 ml. (5.66 gm., 0.92 mole) ethylene glycol, 0.25 gm. p-toluenesulfonic acid, and 160 ml. benzene instead of the 4.8 ml., the 0.21 gm., and the 150 ml., respectively, there is obtained 22.64 gm. (89% yield) of the expected compound 4-(o-chlorophenyl)-4-cyanocyclohexanone, ethylene ketal having a melting range at 98.5° to 101° C.

Analysis: Calc'd. for $C_{15}H_{16}ClNO_2$: C, 64.86; H, 5.81; N, 5.04. Found: C, 64.60; H, 5.79; N, 5.20.

Part E: Preparation of fourth intermediate,
4-carboxy-4-(o-chlorophenyl)cyclohexanone, ethylene ketal Following the procedure of Example 1, Part E, but substituting 22.54 gm. (0.081 mole) of 4-(o-chlorophenyl)-4-cyanocyclohexanone, ethylene ketal (prepared in Part D, above) for the 21.87 gm. of 4-(p-chlorophenyl)-4-cyanocyclohexanone, ethylene ketal and using 23.0 gm. (0.41 mole) potassium hydroxide and 230 ml. ethylene glycol instead of the 22.0 gm. and the 220 ml., respectively, there is obtained 18.49 gm. (77% yield) of 4-carboxy-4-(o-chlorophenyl)cyclohexanone, ethylene ketal having a melting point at 195° to 197° C.

Analysis: Calc'd. for $C_{15}H_{17}ClO_4$: C, 60.71; H, 5.78. Found: C, 61.11; H, 5.96.

Part F: Preparation of fifth intermediate,
4-(o-Chlorophenyl)-4-isocyanatocyclohexanone, ethylene ketal Following the procedure of Example 1, Part F, but substituting 18.49 gm. (0.0625 mole) of 4-carboxy-4-(o-chlorophenyl)cyclohexanone, ethylene ketal (prepared in Part E, above) for the 15.79 gm. of 4-carboxy-4-(p-chlorophenyl)cyclohexanone, ethylene ketal and using 8.7 ml. (6.3 gm., 0.063 mole) triethylamine, 160 ml. anisole, and 17.4 gm. diphenylphosphonic azide instead of the 7.4 ml., the 135 ml., and the 14.7 gm., respectively, there is obtained 15.49 gm. (85% yield) of 4-(o-chlorophenyl)-4-isocyanatocyclohexanone, ethylene ketal as an oil.

Part G: Preparation of sixth intermediate,
4-(o-chlorophenyl)-4-methylaminocyclohexanone, ethylene ketal Following the procedure of Example 1, Part G, but substituting 15.49 gm. (0.053 mole) of 4-(o-chlorophenyl)-4-isocyanatocyclohexanone, ethylene ketal (prepared in Part F, above) for the 6.62 gm. of the 4-(p-chlorophenyl)-4-isocyanatocyclohexanone, ethylene ketal; using 120 ml. tetrahydrofuran, 3.04 gm. (0.08 mole) lithium aluminum hydride, and 50 ml. tetrahydrofuran, respectively; and adding 3.0 ml. water, 3.0 ml. of the 15 percent aqueous sodium hydroxide, and 9.0 ml. water instead of the 1.3 ml., the 1.3 ml., and the 3.9 ml., respectively, there is obtained 14.27 gm. (96% yield) of 4-(o-chlorophenyl)-4-methylaminocyclohexanone, ethylene ketal as a noncrystalline gum.

Part H: Preparation of object compound,
4-(o-chlorophenyl)-4-dimethylaminocyclohexanone, ethylene ketal hydroiodide Following the procedure of Example 1, Part H, but substituting 14.27 gm. (0.051 mole) of the 4-(o-chlorophenyl)-4-methylaminocyclohexanone, ethylene ketal prepared in Part G, above for the 5.68 gm. of the 4-(p-chlorophenyl)-4-methylaminocyclohexanone, ethylene ketal and using 55 ml. of the 37 percent formalin, 190 ml. methanol, and 7.25 gm. (0.191 mole) of the sodium borohydride instead of the 22 ml., the 75 ml., and the 2.89 gm., respectively, there is obtained the free base product from the final removal of methylene chloride, after recycling. This is then dissolved in a small amount of methylene chloride and washed with 10 percent hydriodic acid. After removing the methylene chloride by evaporation under reduced pressure, the residue is recrystallized from a mixture of methanol and diethyl ether to afford 2.7 gm. of the object compound 4-(o-chlorophenyl)-4-dimethylaminocyclohexanone, ethylene ketal hydroiodide having a melting range of 208° to 213° C.

Analysis: Calc'd. for $C_{16}H_{23}ClINO_2$: C, 45.35; H, 5.47; N, 3.31. Found: C, 45.58; H, 5.65; N, 3.18.

EXAMPLE 10

Preparation of an object compound, 4-(o-Chlorophenyl)-4-dimethylaminocyclohexanone Following the procedure of Example 2, but substituting 10.0 gm. (0.034 mole) of 4-(o-chlorophenyl)-4-dimethylaminocyclohexanone, ethylene ketal (prepared in Example 9, Part H, above) for the 4.52 gm. of the 4-(p-chlorophenyl)-4-dimethylaminocyclohexanone, ethylene ketal hydrochloride, and using 50 ml. 2.5 N hydrochloric acid and 100 ml. methanol instead of the 22.5 ml. and the 45 ml., respectively, there is prepared 2.25 gm. (26.3% yield) of 4-(o-chlorophenyl)-4-dimethylaminocyclohexanone having a melting point at 81° to 84° C.

Analysis: Calc'd. for $C_{14}H_{17}ClNO$: C, 66.79; H, 7.21; N, 5.57. Found: C, 66.98; H, 7.54; N, 5.81.

EXAMPLE 11

Preparation of 4-(m-anisyl)-4-dimethylaminocyclohexanone, ethylene ketal hydrochloride Part A: Preparation of precursor, the Dimethyl ester of 4-(m-anisyl)-4-cyanopimelic acid Following the procedure of Example 1, Part A, but substituting 25.0 gm. (0.17 mole) m-anisyl acetonitrile for the 25.0 gm. of the p-chlorophenyl acetonitrile and using 79 ml. methyl acrylate, 27 ml. of the 40% methanolic tetramethylammonium hydroxide with 38 ml. tert-butyl alcohol, instead of the 77 ml., the 24 ml., and the 37 ml., respectively, and decreasing the final distillation pressure to 0.07 mm Hg, there is prepared 30.34 gm. (56% yield) of the dimethyl ester of 4-(m-anisyl)-4-cyanopimelic acid as an oil having a boiling range from 180° to 187° C.

Part B: Preparation of first intermediate, 4-(m-anisyl)-2-carbomethoxy-4-cyanocyclohexanone Following the procedure of Example 1, Part B, but substituting 30.34 gm. (0.0951 mole) of the dimethyl ester of 4-(m-anisyl)-4-cyanopimelic acid (prepared in Part A, above) for the 34.97 gm. of the dimethyl ester of 4-(p-chlorophenyl)-4-cyanopimelic acid and using 620 ml. of the tetrahydrofuran, 21.3 gm. (0.19 mole) of the potassium tert-butoxide, and 150 ml. of the 2.5 N glacial acetic acid instead of the 700 ml., the 24.4 gm. (0.218 mole), and the 175 ml., respectively, there is prepared 29.1 gm. (99% yield) of 4-(m-anisyl)-2-carbomethoxy-4-cyanocyclohexanone as a gum.

Part C: Preparation of second intermediate, 4-(m-anisyl)-4-cyanocyclohexanone

Following the same procedure as described in Example 1, Part C, but substituting 29.1 gm. (0.101 mole) of 4-(m-anisyl)-2-carbomethoxy-4-cyanocyclohexanone (prepared in Part B, above) for the 29.8 gm. of 2-carbomethoxy-4-(p-chlorophenyl)-4-cyanocyclohexanone, there is obtained 14.93 gm. (64% yield) of 4-(m-anisyl)-4-cyanocyclohexanone having a melting range at 72° to 76° C.

Analysis: Calc'd. for $C_{14}H_{15}NO_2$: C, 73.34; H, 6.59; N, 6.11. Found: C, 73.68; H, 6.76; N, 6.21.

Part D: Preparation of third intermediate, 4-(m-anisyl)-4-cyanocyclohexanone, ethylene ketal Following the procedure of Example 1, Part D, but substituting 14.93 gm. (0.065 mole) of 4-(m-anisyl)-4-cyanocyclohexanone (prepared in Part C, above) for the 19.49 gm. of the 4-(p-chlorophenyl)-4-cyanocyclohexanone, using 4.0 ml. ethylene glycol, 0.16 gm. p-toluenesulfonic acid, and 110 ml. benzene instead of the 4.8 ml., the 0.21 gm., and the 150 ml., respectively, and recrystallizing from technical hexane instead of cyclohexane, there is obtained 16.24 gm. (92% yield) of 4-(m-anisyl)-4-cyanocyclohexanone, ethylene ketal melting at 70° to 72° C.

Analysis: Calc'd. for $C_{16}H_{19}NO_3$: C, 70.31; H, 7.01; N, 5.13. Found: C, 70.09; H, 7.07; N, 4.96.

Part E: Preparation of fourth intermediate 4-(m-anisyl)-4-carboxycyclohexanone, ethylene ketal Following the procedure of Example 1, Part E, but substituting 16.24 gm. (0.059 mole) of 4-(m-anisyl)-4-cyanocyclohexanone, ethylene ketal (prepared in Part D, above) for the 21.87 gm. of the 4-carboxy-4-(p-chlorophenyl)cyclohexanone, ethylene ketal and using 7.83 gm. (0.19 mole) sodium hydroxide and 110 ml. ethylene glycol instead of the 22.0 gm. (0.39 mole) potassium hydroxide and 220 ml., respectively, there is obtained, without recrystallization, 17.31 gm. (99% yield) of 4-(m-anisyl)-4-carboxycyclohexanone, ethylene ketal having a melting range at 102° to 107° C.

Part F: Preparation of fifth intermediate, 4-(m-anisyl)-4-isocyanatocyclohexanone, ethylene ketal Following the procedure of Example 1, Part F, but substituting the 17.31 gm. (0.059 mole) of 4-(m-anisyl)-4-carboxycyclohexanone, ethylene ketal (prepared in Part F, above) for the 15.79 gm. of the 4-carboxy-4-(p-chlorophenyl)cyclohexanone, ethylene ketal and using 6.0 ml. (8.23 gm., 0.059 mole) triethylamine, 160 ml. anisole, and 16.31 gm. diphenylphosphonic azide instead of the 7.4 ml., the 135 ml., and the 14.7 gm., respectively, there is obtained after elution of the silica gel column with a 1.5 percent mixture of ethyl acetate in methylene chloride, 4.07 gm. of 4-(m-anisyl)-4-isocyanatocyclohexanone ethylene ketal.

Part G: Preparation of sixth intermediate, 4-(m-anisyl)-4-methylaminocyclohexanone, ethylene ketal hydrochloride Following the procedure of Example 1, Part G, but substituting 4.07 gm. (0.014 mole) of 4-(m-anisyl)-4-isocyanatocyclohexanone, ethylene ketal (prepared in Part F, above) for the 6.62 gm. 4-(p-chlorophenyl)-4-isocyanatocyclohexanone, ethylene ketal and using 80 ml. tetrahydrofuran, 0.76 gm. (0.02 mole) lithium aluminum hydride, and 10 ml. tetrahydrofuran instead of the 50 ml., the 1.29 gm., and the 20 ml., adding 0.76 ml. water, 0.76 ml. of 15 percent aqueous sodium hydroxide, and 2.28 ml. water instead of the 1.3 ml., the 1.3 ml., and the 3.9 ml., respectively, there is obtained a corresponding residue from the filtrate that is dissolved in a small amount of diethyl ether. The ether solution is acidified with an equivalent amount of 3 N hydrogen chloride in ether. The hydrochloride acid addition salt that precipitated is collected on a filter and recrystallized from a mixture of methylene chloride and ethyl acetate to afford 3.10 gm. (71% yield) of 4-(m-anisyl)-4-methylaminocyclohexanone, ethylene ketal hydrochloride having a melting point at 238° to 239° C.

Analysis: Calc'd. for $C_{16}H_{24}ClNO_3$: C, 61.23; H, 7.71; N, 4.46. Found: C, 60.07; H, 7.52; N, 4.29.

Part H: Preparation of object compound, 4-(m-anisyl)-4-(dimethylamino)cyclohexanone, ethylene ketal hydrochloride Following the procedure of Example 1, Part H, but substituting the free base from 3.10 gm. (0.0099 mole) of 4-(m-anisyl)-4-methylaminocyclohexanone ethylene ketal hydrochloride (prepared in Part G, above) for the 5.68 gm. of the 4-(p-chlorophenyl)-4-methylaminocyclohexanone, ethylene ketal and using 7.5 ml. of 37 percent formalin, 22.5 ml. methanol, and adding 0.91 gm. sodium borohydride instead of the 22 ml., the 75 ml., and the 2.89 gm. respectively, there is obtained a hydrochloride precipitate that upon recrystallization from a mixture of methylene chloride and ethyl acetate gives 2.21 gm. (68% yield) of 4-(m-anisyl)-4-(dimethylamino)cyclohexanone, ethylene ketal hydrochloride having a melting point at 184° to 185.5° C.

Analysis: Calc'd. for $C_{17}H_{26}ClNO_3$: C, 62.28; H, 7.99; N, 4.27. Found: C, 62.11; H, 8.24; N, 4.21.

EXAMPLE 12

Preparation of an object compound, 4-(m-anisyl)-4-dimethylaminocyclohexanone

Following the procedure of Example 2, but substituting 1.71 gm. (0.0052 mole) of 4-(m-anisyl)-4-dimethylaminocyclohexanone, ethylene ketal hydrochloride (prepared in Example 11, Part H, above) for the 4-(p-chlorophenyl)-4-dimethylaminocyclohexanone, ethylene ketal hydrochloride, 7.5 ml. of 2.5 N hydrochloride acid for the 22.5 ml., and 15 ml. methanol for the 45 ml., there is prepared (after recrystallization from petroluem ether instead of diethyl ether) 0.54 gm. (45% yield) of 4-(m-anisyl)-4-dimethylaminocyclohexanone as the free base having a melting point at 57° to 59° C.

Analysis: Calc'd. for $C_{15}H_{21}NO_2$: C, 72.84; H, 8.56; N, 5.66. Found: C, 72.88; H, 8.47; N, 5.72.

EXAMPLE 13

Preparation of 4-Dimethylamino-4-(p-tolyl)cyclohexanone, ethylene ketal hydrochloride Part A: Preparation of precursor, the Dimethyl ester of 4-cyano-4-(p-tolyl)pimelic acid Following the procedure of Example 1, Part A, but substituting 25.0 gm. (0.191 mole) p-tolyl acetonitrile for the 25.0 gm. of the p-chlorophenyl acetonitrile and using 89 ml. methyl acrylate, 90 ml. tert-butyl alcohol, 29 ml. of 40 percent methanolic tetramethylammonium hydroxide, and 43 ml. tert-butyl alcohol instead of the 77 ml., the 80 ml., the 25 ml., and the 37 ml., respectively, and decreasing the final distillation pressure to 0.07 mm mercury, there is prepared 42.44 gm. (73% yield) of the dimethyl ester of 4-cyano-4-(p-tolyl)pimelic acid as an oil having a boiling range of 170° to 180° C.

Part B: Preparation of first intermediate, 2-carbomethoxy-4-cyano-4-(p-tolyl)cyclohexanone Following the procedure of Example 1, Part B, but substituting 42.44 gm. (0.14 mole) of the dimethyl ester of 4-cyano-4-(p-tolyl)pimelic acid (prepared in Part A, above) for the dimethyl ester of 4-(p-chlorophenyl)-4-cyanopimelic acid and using 900 ml. of the tetrahydrofuran, 31.5 gm. (0.28 mole) of the potassium tert-butoxide, and 225 ml. of the 2.5 N aqueous acetic acid instead of the 700 ml., the 24.4 gm. (0.218 mole), and the 175 ml., respectively, there is prepared 39.3 gm. (99% yield) of 2-carbomethoxy-4-cyano-4-(p-tolyl)cyclohexanone as a gum.

Part C: Preparation of second intermediate, 4-Cyano-4-(p-tolyl)cyclohexanone

Following the procedure of Example 1, Part C, but substituting 39.3 gm. (0.145 mole) of 2-carbomethoxy-4-cyano-4-(p-tolyl)cyclohexanone (prepared in Part B, above) for the 29.8 gm. of the 2-carbomethoxy-4-(p-chlorophenyl)-4-cyanocyclohexanone and using 960 ml. glacial acetic acid and 480 ml. of 10 percent aqueous sulfuric acid instead of the 660 ml. and 330 ml., respectively, there is obtained after recrystallization from a mixture of diethyl ether and petroleum ether 22.84 gm. (74% yield) of 4-cyano-4-(p-tolyl)cyclohexanone having a melting range at 79° to 82° C.

Analysis: Calc'd. for $C_{14}H_{15}NO$: C, 78.84; H, 7.09; N, 6.57. Found: C, 78.96; H, 7.07; N, 6.53.

Part D: Preparation of third intermediate, 4-Cyano-4-(p-tolyl)cyclohexanone, ethylene ketal Following the procedure of Example 1, Part D, but substituting 22.74 gm. (0.107 mole) of 4-cyano-4-(p-tolyl)cyclohexanone (prepared in Part C, above) for the 19.49 gm. of the 4-(p-chlorophenyl)-4-cyanocyclohexanone and using 6.3 ml. (7.0 gm., 0.113 mole) ethylene glycol, 0.28 gm. p-toluenesulfonic acid, and 190 ml. benzene instead of the 4.8 ml., the 0.21 gm., and the 150 ml., respectively, there is thus obtained 25.29 gm. (92% yield) of 4-cyano-4-(p-tolyl)cyclohexanone, ethylene ketal having a melting range at 107.5° to 110° C.

Analysis: Calc'd. for $C_{16}H_{19}NO_2$: C, 74.68; H, 7.44; N, 5.44. Found: C, 75.04; H, 7.40; N, 5.48.

Part E: Preparation of fourth intermediate, 4-Carboxy-4-(p-tolyl)cyclohexanone, ethylene ketal Following the procedure of Example 1, Part E, but substituting 25.29 gm. (0.0985 mole) of 4-cyano-4-(p-tolyl)cyclohexanone, ethylene ketal (prepared in Part D, above) for the 21.87 gm. of the 4-(p-chlorophenyl)-4-cyanocyclohexanone, ethylene ketal and using 25.0 gm. (0.45 mole) potassium hydroxide and 250 ml. ethylene glycol instead of the 22.0 gm. and the 220 ml., respectively, there is obtained 23.04 gm. (85% yield) of the expected compound 4-carboxy-4-(p-tolyl)cyclohexanone, ethylene ketal having a melting range of 72° to 74° C.

Analysis: Calc'd. for $C_{16}H_{20}O_4$: C, 69.54; H, 7.30. Found: C, 69.79; H, 7.31.

Part F: Preparation of fifth intermediate, 4-Isocyanato-4-(p-tolyl)cyclohexanone, ethylene ketal Following the procedure of Example 1, Part F, but substituting 22.94 gm. (0.083 mole) of 4-carboxy-4-(p-tolyl)cyclohexanone, ethylene ketal (prepared in Part E, above) for the 15.79 gm. of the 4-carboxy-4-(p- chlorophenyl)cyclohexanone, ethylene ketal using 12.6 ml. (9.15 gm., 0.092 mole) triethylamine, 270 ml. anisole, and 24.5 gm. diphenylphosphonic azide for the 7.4 ml., the 135 ml., and the 14.7 gm., respectively, and chromatographing over a 2000 ml. column instead of a 1500 ml. column, there is obtained 19.0 gm. (84% yield) of 4-isocyanato-4-(p-tolyl)cyclohexanone, ethylene ketal as an oil.

Part G: Preparation of sicth intermediate, 4-Methylamino-4-(p-tolyl)cyclohexanone, ethylene ketal Following the procedure of Example 1, Part G, but substituting 19.07 gm. (0.0675 mole) of 4-isocyanato-4-(p-tolyl)cyclohexanone, ethylene ketal (prepared in Part F, above) for the 6.62 gm. of the 4-(p-chlorophenyl)4-isocyanatocyclohexanone, ethylene ketal, using 325 ml. tetrahydrofuran, 4.0 gm. (0.105 mole) lithium aluminum hydride, and 40 ml. tetrahydrofuran; and adding 4.0 ml. water, 4.0 ml. of 15 percent sodium hydroxide, and 12 ml. water instead of the 1.3 ml., 1.3 ml., and 3.9 ml., respectively, there is obtained 14.75 gm. (57% yield) of 4-methylamino-4-(p-tolyl)cyclohexanone, ethylene ketal having a melting range at 56° to 60° C.

Analysis: Calc'd. for $C_{16}H_{23}NO_2$: C, 73.53; H, 8.87; N, 5.36. Found: C, 73.19; H, 9.01; N, 5.46.

Part H: Preparation of object compound, 4-Dimethylamino-4-(p-tolyl)cyclohexanone, ethylene ketal hydrochloride Following the procedure of Example 1, Part H, but substituting 7.0 gm. (0.027 mole) of 4-methylamino-4-(p-tolyl)cyclohexanone, ethylene ketal (prepared in Part G, above) for the 5.68 gm. of the 4-(p-chlorophenyl)-4-methylaminocyclohexanone, ethylene ketal and initially using 29.2 ml. of 37 percent formalin, 100 ml. methanol, and 3.96 gm. (0.104 mole) sodium borohydride instead of the 22 ml., the 75 ml., and the 2.89 gm., respectively, there is obtained the free base; this on further treatment as in Example 1, Part H gives a hydrochloride acid addition salt precipitate that is recrystallized from a solvent mixture consisting of methylene chloride and ethyl acetate thus affording 6.27 gm. (76% yield) of the desired, object compound 4-dimethylamino-4-(p-tolyl)-cyclohexanone, ethylene ketal hydrochloride salt which melts at 228° to 229° C.

Analysis: Calc'd. for $C_{17}H_{26}ClNO_2$: C, 65.47; H, 8.40; N, 4.49. Found: C, 65.57; H, 8.30; N, 4.60.

EXAMPLE 14

Preparation of an object compound, 4-dimethylamino-4-(p-tolyl)cyclohexanone

Following the procedure of Example 2, but substituting 6.27 gm. (0.02 mole) of 4-dimethylamino-4-(p-tolyl)-cyclohexanone, ethylene ketal hydrochloride (prepared in Example 13, Part H, above) for the 4-(p-chlorophenyl)-4-dimethylaminocyclohexanone, ethylene ketal hydrochloride, 31 ml. 2.5 N hydrochloric acid for the 22.5 ml., and 62 ml. methanol for the 45 ml., there is prepared (after recrystallization from petroleum ether instead of diethyl ether) 2.54 gm. (55% yield) of 4-dimethylamino-4-(p-tolyl)cyclohexanone having a melting point at 65° to 67.5° C.

Analysis: Calc'd. for $C_{15}H_{21}NO$: C, 77.88; H, 9.15; N, 6.06. Found: C, 77.72; H, 9.14; N, 6.24.

EXAMPLE 15

Preparation of 4-Dimethylamino-4-(o-tolyl)cyclohexanone, ethylene ketal hydroiodide Part A: Preparation of precursor, the Dimethyl ester of 4-cyano-4-(o-tolyl)pimelic acid Following the procedure of Example 1, Part A, but substituting 25.0 gm. (0.191 mole) o-tolyl acetonitrile for the 25.0 gm. of the p-chlorophenyl acetonitrile and using 89 ml. methyl acrylate, 90 ml. tert-butyl alcohol, 29 ml. of 40 percent methanolic tetramethylammonium hydroxide, and 43 ml. tert-butyl alcohol instead of the 77 ml., the 80 ml., the 24 ml., and the 37 ml., respectively, and decreasing the final distillation pressure to 0.03 mm mercury, there is prepared 21.76 gm. (37% yield) of the dimethyl ester of 4-cyano-4-(o-tolyl)pimelic acid as an oil having a boiling range between 168° to 175° C.

Part B: Preparation of first intermediate, 2-Carbomethoxy-4-cyano-4-(o-tolyl)cyclohexanone Following the procedure of Example 1, Part B, but substituting 21.76 gm. (0.0715 mole) of the dimethyl ester of 4-cyano-4-(o-tolyl)pimelic acid (prepared in Part A, above) for the 34.97 gm. of the dimethyl ester of 4-(p-chlorophenyl)-4-cyanopimelic acid and using 460 ml. of the tetrahydrofuran, 16.3 gm. (0.145 mole) of the potassium tert-butoxide, and 115 ml. of the 2.5 N aqueous acetic acid instead of the 700 ml., the 24.4 gm. and the 175 ml., respectively, there is prepared 18.0 gm. (93% yield) of 2-carbomethoxy-4-cyano-4-(o-tolyl)cyclohexanone as a crystalline solid having a melting range at 107° to 113° C.

Part C: Preparation of second intermediate, 4-Cyano-4-(o-tolyl)cyclohexanone

Following the procedure of Example 1, Part C, but substituting 18.0 gm. (0.0663 mole) of the 2-carbomethoxy-4-cyano-4-(o-tolyl)cyclohexanone (prepared in Part B, above), for the 29.8 gm. of the 2-carbomethoxy-4-(p-chlorophenyl)-4-cyanocyclohexanone, using 440 ml. of the acetic acid and 220 ml. of the 10 percent aqueous sulfuric acid instead of the 660 ml., and the 330 ml., respectively, and heating for 48 hours instead of 24 hours there is prepared 4-cyano-4-(o-tolyl)cyclohexanone which upon recrystallization from a mixture of diethyl ether and technical hexane affords 11.05 gm. of the compound having a melting range at 86.5° to 89° C.

Analysis: Calc'd. for $C_{14}H_{15}NO$: C, 78.84; H, 7.09; N, 6.57. Found: C, 78.85; H, 7.29; N, 6.55.

Part D: Preparation of third intermediate, 4-Cyano-4-(o-tolyl)cyclohexanone, ethylene ketal Following the procedure of Example 1, Part D, but substituting 10.95 gm. (0.0513 mole) of 4-cyano-4-(o-tolyl) cyclohexanone (prepared in Part C, above) for the 19.49 gm. (0.084 mole) of the 4-(p-chlorophenyl)-4-cyanocyclohexanone and using 3.1 ml. (3.44 gm., 0.044 mole) ethylene glycol, 0.14 gm. p-toluenesulfonic acid, and 90 ml. benzene instead of the 4.7 ml., the 0.21 gm., and the 150 ml., respectively, there is thus obtained a residual solid that is recrystallized from a mixture of diethyl ether and petroleum ether thus affording 11.22 gm. (85% yield) of 4-cyano-4-(o-tolyl)cyclohexanone, ethylene ketal having a melting range at 65.5° to 68.5° C.

Analysis: Calc'd. for $C_{16}H_{19}NO_2$: C, 74.68; H, 7.44; N, 5.44. Found: C, 74.56; H, 7.50; N, 5.29.

Part E: Preparation of fourth intermediate, 4-Carboxy-4-(o-tolyl)cyclohexanone, ethylene ketal Following the procedure of Example 1, Part E, but substituting 11.22 gm. (0.044 mole) of 4-cyano-4-(o-tolyl)cyclohexanone, ethlene ketal (prepared in Part D, above) for the 21.87 gm. of the 4-(p-chlorophenyl)-4-cyanocyclohexanone, ethylene ketal and using 11.0 gm. (0.20 mole) potassium hydroxide and 110 ml. ethylene glycol instead of the 2..0 gm. and 220 ml., respectively, there is obtained 7.70 gm. (63.3% yield) of 4-carboxy-4-(o-tolyl)cyclohexanone, ethylene ketal having a melting range at 174° to 177° C.

Analysis:

Calc'd. for $C_{16}H_{20}O_4$: C, 69.54; H, 7.30. Found: C, 69.43; H, 7.62.

Part F: Preparation of fifth intermediate, 4-Isocyanato-4-(o-tolyl)cyclohexanone, ethylene ketal Following the procedure of Example 1, Part F, but substituting 7.70 gm. (0.028 mole) of 4-carboxy-4-(o-tolyl)-cyclohexanone, ethylene ketal (prepared in Part E, above) for the 15.79 gm. of the 4-carboxy-4-(p-chlorophenyl)cyclohexanone, ethylene ketal and using 4.3 ml. (3.12 gm., 0.031 mole) triethylamine, 90.0 ml. anisole, and 8.4 gm. diphenylphosphonic azide instead of the 7.4 ml., the 135 ml., and the 14.7 gm., respectively, followed by chromatographic separation on a 400 ml. column of silica gel instead of the 1500 ml. column and elution with 2 percent ethyl acetate in methylene chloride instead of ethyl acetate and technical hexane, there is obtained 6.09 gm. (79.6% yield) of 4-isocyanato-4-(o-tolyl)cyclohexanone, ethylene ketal as a gum.

Part G: Preparation of sixth intermediate, 4-Methylamino-4-(o-tolyl)cyclohexanone, ethylene ketal hydrochloride Following the procedure of Example 1, Part G, but substituting 6.09 gm. (0.022 mole) of 4-isocyanato-4-(o-tolyl)cyclohexanone, ethylene ketal (prepared in Part F, above) for the 6.62 gm. of the 4-(p-chlorophenyl)-4-isocyanatocyclohexanone ethylene ketal, using 105 ml. tetrahydrofuran, 1.28 gm. (0.034 mole) lithium aluminum hydride, and 10 ml. tetrahydrofuran instead of the 50 ml., the 1.29 gm., and the 20 ml., respectively, there is obtained a corresponding residue from the filtrate that is dissolved in a small amount of diethyl ether and the solution is acidified with just enough 3 N hydrogen chloride in ether to precipitate the hydrochloride salt which is collected on a filter and recrystallized from a mixture of methylene chloride and ethyl acetate to afford 4.03 gm. (59.7% yield) of the desired 4-methylamino-4-(o-tolyl)cyclohexanone, ethylene ketal hydrochloride having a melting point at 231° to 233° C.

Analysis: Calc'd. for $C_{16}H_{24}ClNO_2.\frac{1}{2}H_2O$: C, 62.62; H, 8.21; N, 4.57. Found: C, 62.78; H, 8.01; N, 4.72.

Part H: Preparation of object compound, 4-Dimethylamino-4-(o-tolyl)cyclohexanone, ethylene ketal hydroiodide A solution of the free base from 3.93 gm. (0.013 mole) of 4-methylamino-4-(o-tolyl)cyclohexanone, ethylene ketal hydrochloride (prepared in Part G, above) with 14.4 ml. of 37 percent formalin in 50 ml. methanol is heated at the reflux temperature for four (4) hours. The refluxed solution is allowed to cool, and it is then chilled in an icebath. Small portions of sodium borohydride are added cautiously with stirring to a total of 1095 gm. (0.051 mole). Stirring is continued for two (2) hours at 25° C., after which the bulk of the solvent is removed under reduced pressure. The concentrate thus obtained is dispersed in a mixture of 200 ml. methylene chloride and 25 ml. water. A methylene chloride phase separates upon discontinuance of agitation. It is recovered and washed with water and brine before the methylene chloride is removed by evaporation under reduced pressure. The residue thus obtained is recycled through the same reaction and work up. A portion (1.68 g.) of this second residue is dissolved in methylene chloride and washed with 10 percent hydriodic acid. The methylene chloride phase is separated, the solvent removed by evaporation under reduced pressure and the residue thus obtained is recrystallized from a mixture of methylene chloride and ether to afford 2.03 gm. (37.1% yield) of the desired object compound, 4-dimethylamino-4-(o-tolyl)cyclohexanone, ethylene ketal hydroiodide having a melting point at 182° to 183.5° C.

Analysis: Calc'd. for $C_{17}H_{26}INO_2.H_2O$: C, 48.45; H, 6.70; N, 3.33. Found: C, 48.77; H, 6.54; N, 3.41.

EXAMPLE 16

Preparation of an object compound, 4-Dimethylamino-4-(o-tolyl)cyclohexanone free base and the hydroiodide thereof Following the procedure of Example 2, but substituting 2.0 gm. (0.0073 mole) of 4-dimethylamino-4-(o-tolyl)cyclohexanone, ethylene ketal hydroiodide (prepared in Example 15, Part H, above) for the 4-(p-chlorophenyl)-4-dimethylaminocyclohexanone, ethylene ketal hydrochloride and using 10 ml. of the 2.5 N hydrochloric acid and 20 ml. of the methanol instead of 22.5 ml. and 45 ml., respectively, there is obtained 4-dimethylamino-4-(o-tolyl)cyclohexanone free base as the residue. This residue is dissolved in 50 ml. methylene chloride and shaken with 10 ml. 10 percent aqueous hydriodic acid. The methylene chloride layer is separated and the solvent removed by evaporation under reduced pressure. The residue thus obtained is recrystallized from a mixture of methanol and diethyl ether. There is thus obtained 0.94 gm. (35.8% yield) of 4-dimethylamino-4-(o-tolyl)cyclohexanone hydroiodide having a melting range of 162° to 165° C.

Analysis: Calc'd. for $C_{15}H_{22}INO$: C, 50.15; H, 6.17; N, 3.90. Found: C, 49.86; H, 6.37; N, 4.00.

EXAMPLE 17

Preparation of 4-Dimethylamino-4-phenylcyclohexanone, ethylene ketal hydrochloride Part A: Preparation of precursor, the Dimethyl ester of 4-cyano-4-phenylpimelic acid Following the procedure of Example 1, Part A, but substituting 20.26 gm. (0.25 mole) of phenyl acetonitrile for the 25.0 gm. of p-chlorophenyl acetonitrile and using 116 ml. methyl acrylate, 120 ml. tert-butyl alcohol, 38 ml. of the 40 percent methanolic tetramethylammonium hydroxide, and 56 ml. tert-butyl alcohol instead of the 77 ml., the 80 ml., the 24 ml., and the 37 ml. quantities stated, respectively, and increasing the final distillation pressure to 0.45 mm of mercury, there is prepared 55.15 gm. (70% yield) of the dimethyl ester of 4-cyano-4-phenylpimelic acid as an oil having a boiling range from 183° to 186° C.

Part B: Preparation of first intermediate, 2-Carbomethoxy-4-cyano-4-phenylcyclohexanone Following the procedure of Example 1, Part B, but substituting 2.0 gm. (0.0069 mole) of the dimethyl ester of 4-cyano-4-phenylpimelic acid (prepared in Part A, above) for the 34.97 gm. of the dimethyl ester of 4-(p-chlorophenyl)-4-cyanopimelic acid and using 45 ml. of the tetrahydrofuran, 1.57 gm. (0.014 mole) of the potassium tert-butoxide, and 10 ml. of the 2.5 N acetic acid instead of the 700 ml., the 24.4 gm., and the 175 ml., respectively, there is thus obtained a residue which upon recrystallization from technical hexane gives 1.07 gm. (60% yield) of the desired 2-carbomethoxy-4-cyano-4-phenylcyclohexanone having a melting point at 79.5° to 81.5° C.

Analysis: Calc'd. for $C_{15}H_{15}NO_3$: C, 70.02; H, 5.88; N, 5.44. Found: C, 69.77; H, 5.88; N, 5.54.

Part C: Preparation of second intermediate, 4-Cyano-4-phenylcyclohexanone

Following the procedure of Example 1, Part C, but substituting 44.7 gm. (0.174 mole) of 2-carbomethoxy-4-cyano-4-phenylcyclohexanone (prepared as in Part B, above) for the 29.8 gm. of the 2-carbomethoxy-4-(p-chlorophenyl)-4-cyanocyclohexanone and using 1200 ml. of the glacial acetic acid, and 600 ml. of the 10% aqueous sulfuric acid instead of the 660 ml. and the 330 ml., respectively, and finally recrystallizing the residual solid from a mixture of ethyl acetate and hexane, there is obtained 25.75 gm. (75% yield) of the desired 4-cyano-4-phenylcyclohexanone having a melting range from 112° to 115.5° C.

Part D: Preparation of third intermediate, 4-Cyano-4-phenylcyclohexanone, ethylene ketal Following the procedure of Example 1, Part D, but substituting 10.0 gm. (0.05 mole) of 4-cyano-4-phenylcyclohexanone (prepared in Part C, above) for the 4-(p-chlorophenyl)-4-cyanocyclohexanone and using 2.85 ml. (3.17 gm., 0.051 mole) of the ethylene glycol, 0.12 gm. of the p-toluenesulfonic acid, and 90 ml. of the benzene solvent instead of the 4.8 ml., the 0.21 gm., and the 150 ml., respectively, there is obtained 11.27 gm. (92% yield) of the desired 4-cyano-4-phenylcyclohexanone, ethylene ketal as crystals having a melting range of 120° to 122.5° C.

Analysis: Calc'd. for $C_{15}H_{17}NO_2$: C, 74.05; H, 7.04; N, 5.76. Found: C, 74.10; H, 6.98; N, 5.77.

Part E: Preparation of fourth intermediate, 4-Carboxy-4-phenylcyclohexanone, ethylene ketal Following the procedure of Example 1, Part E, but substituting 11.27 gm. (0.0464 mole) of 4-cyano-4-phenylcyclohexanone, ethylene ketal (prepared in Part D, above) for the 21.87 gm. of the 4-(p-chlorophenyl)-4-cyanocyclohexanone, ethylene ketal, and using 11.3 gm. (0.2 mole) of the potassium hydroxide, and 90 ml. of the ethylene glycol instead of the 22.0 gm. and 220 ml., respectively, there is obtained 10.51 gm. (86% yield) of the desired 4-carboxy-4-phenylcyclohexanone, ethylene ketal as crystals having a melting range from 136° to 140.5° C.

Analysis: Calc'd. for $C_{15}H_{18}O_4$: C, 68.68; H, 6.92. Found: C, 68.27; H, 6.90.

Part F: Preparation of fifth intermediate, 4-Isocyanato-4-phenylcyclohexanone, ethylene ketal Following the procedure of Example 1, Part F, but substituting 2.62 gm. (0.01 mole) of 4-carboxy-4-phenylcyclohexanone ethylene ketal (prepared in Part E, above) for the 15.79 gm. of the 4-carboxy-4-(p-chlorophenyl)cyclohexanone, ethylene ketal and using 1.38 ml. (1.01 gm., 0.01 mole) of the triethylamine, 25 ml. of the anisole, 2.75 gm. of the diphenylphosphonic azide, and a 400 ml. silica gel column instead of the 7.4 ml. (5.36 gm., 0.532 mole), the 135 ml., the 14.7 gm., and the 1500 ml. column, respectively, there is obtained 1.94 gm. (75% yield) of the desired 4-isocyanato-4-phenylcyclohexanone, ethylene ketal which has a melting range from 47° to 50° C.

Analysis: Calc'd. for $C_{15}H_{17}NO_3$: C, 69.48; H, 6.61; N, 5.40. Found: C, 69.56; H, 7.01; N, 5.39.

Part G: Preparation of sixth intermediate, 4-Methylamino-4-phenylcyclohexanone, ethylene ketal hydrochloride A solution consisting of 0.96 gm. (0.0037 mole) of 4-isocyanato-4-phenylcyclohexanone, ethylene ketal (prepared in Part F, above) and 15 ml. tetrahydrofuran is added to a well-stirred suspension prepared by dispersing 0.20 gm. (0.0053 mole) lithium aluminum hydride in 5 ml. tetrahydrofuran. The resulting reaction mixture is heated at the reflux temperature with stirring for four (4) hours. The mixture is then allowed to cool before chilling it in an ice-bath. To the chilled mixture is added 0.2 ml. water, 0.2 ml. 15% aqueous sodium hydroxide, and a further 0.6 ml. water. A gelatinous precipitate forms and the whole preparation is poured onto a filter. The filtrate is collected and the volatile components are removed by evaporation under reduced pressure. The residue thus obtained is dissolved in a small amount of diethyl ether and 3 N hydrogen chloride in ether is added to the solution to give the desired, insoluble acid addition salt. After collecting the crude salt on a filter and recrystallizing it from a mixture of methylene chloride and ethyl acetate, there is obtained 0.82 gm. (78% yield) of 4-methylamino-4-phenylcyclohexanone, ethylene ketal hydrochloride having a melting point at 243° to 245° C.

Analysis: Calc'd. for $C_{15}H_{22}ClNO_2$: C, 63.48; H, 7.82; N, 4.94. Found: C, 63.51; H, 7.89; N, 5.00.

Part H: Preparation of object compound, 4-Dimethylamino-4-phenylcyclohexanone, ethylene ketal hydrochloride A reaction solution consisting of the free base from 1.0 gm. (0.00354 mole) 4-methylamino-4-phenylcyclohexanone, ethylene ketal hydrochloride (prepared as in Part G, above), 3.6 ml. 37% formalin, and 12 ml. methanol is heated at the reflux temperature for four (4) hours. This reaction mixture is allowed to cool to room temperature before chilling it in an ice-bath. Small portions of sodium borohydride are cautiously added with stirring, to a total amount of 0.48 gm. (0.125 mole). Stirring is continued at 25° C. for two (2) hours, and then the volatile solvents are removed by evaporation under reduced pressure. The residue thus obtained is dispersed in a mixture of 50 ml. methylene chloride and 10 ml. water and the liquids are allowed to separate. The methylene chloride phase is recovered and washed with water and then with brine. After removing the methylene chloride solvent by evaporation under reduced pressure, the residue is dissolved in a small amount of ether. A solution of hydrogen chloride in ether (3 N) is added so as to produce the hydrochloride acid addition salt which precipitates out. The precipitate is collected on a filter and recrystallized from a mixture of methylene chloride and ethyl acetate to give 0.72 gm. (68% yield) of the desired final product, 4-dimethylamino-4-phenylcyclohexanone, ethylene ketal hydrochloride having a melting range from 226° to 229° C. An analytical sample is obtained by recrystallization from methylene chloride and ethyl acetate having a melting range from 236° to 238° C.

Analysis: Calc'd. for $C_{16}H_{24}ClNO_2$: C, 64.52; H, 8.12; N, 4.70. Found: C, 64.47; H, 7.85; N, 4.92.

EXAMPLE 18

Preparation of 4-Dimethylamino-4-phenylcyclohexanone

Following the procedure of Example 2, but substituting 13.66 gm. (0.052 mole) 4-dimethylamino-4-phenylcyclohexanone, ethylene ketal (prepared in Example 17, Part H, above) for the 4.52 gm. of the 4-(p-chlorophenyl)-4-dimethylaminocyclohexanone, ethylene ketal hydrochloride and using 70 ml. 2.5 N hydrochloric acid and 14 ml. methanol instead of the 22.5 ml. and 45 ml., respectively, there is prepared 7.76 gm. (69% yield) of 4-dimethylamino-4-phenylcyclohexanone having a melting point at 98° to 99.5° C. An analytical sample has a melting range at 100° to 103° C.

Analysis: Calc'd. for $C_{14}H_{19}NO$: C, 77.38; H, 8.81; N, 6.45. Found: C, 77.39; H, 8.86; N, 6.41.

EXAMPLE 19

Part A

Following the procedure of Example 1, Part A, but substituting the primary reactant p-bromophenyl acetonitrile for the p-chlorophenyl acetonitrile and modifying other factors of the procedure as noted in Table A, there is prepared the corresponding precursor dimethyl ester of 4-(p-bromophenyl)-4-cyanopimelic acid as an oil.

EXAMPLE 20

Part A

Following the procedure of Example 1, Part A, but substituting the primary reactant m-chlorophenyl acetonitrile for the p-chlorophenyl acetonitrile and modifying other factors of the procedure as noted in Table A, there is prepared the corresponding precursor dimethyl ester of 4-(m-chlorophenyl)-4-cyanopimelic acid as an oil.

EXAMPLE 21

Part A

Following the procedure of Example 1, Part A, but substituting the primary reactant 3,4-dichlorophenyl acetonitrile for the p-chlorophenyl acetonitrile and modifying other factors of the procedure as noted in Table A, there is prepared the corresponding precursor dimethyl ester of 4-(3,4-dichlorophenyl)-4-cyanopimelic acid as an oil.

EXAMPLE 22

Part A

Following the procedure of Example 1, Part A, but substituting the primary reactant 2,4-dichlorophenyl acetonitrile for the p-chlorophenyl acetonitrile and modifying other factors of the procedure as noted in Table A, there is prepared the corresponding precursor, dimethyl ester of 4-(2,4-dichlorophenyl)-4-cyanopimelic acid as an oil.

TABLE A

| Factor in procedure | Example 19 | Example 20 | Example 21 | Example 22 |
|---|---|---|---|---|
| Weight of Starting Compound (gm.) | 25.0 | 25.0 | 25.0 | 25.0 |
| Molar Amount | (0.128) | (0.165) | (0.134) | (0.134) |
| Methyl Acrylate (ml.) | 60.0 | 77.0 | 63.0 | 63.0 |
| Tert-butyl alcohol (ml.) | 60.0 | 80.0 | 66.0 | 66.0 |
| 40% Methanolic tetramethyl ammonium hydroxide (ml.) | 19.5 | 25.0 | 21.5 | 21.5 |
| Tert-butyl Alcohol (ml.) | 29.0 | 37.0 | 30.0 | 30.0 |
| Initial Distillation Pressure (mm Hg) | 40 | 40 | 40 | 40 |
| Final Distillation Pressure (mm Hg) | 0.04 | 0.04 | 0.05 | 0.04 |
| Weight of Product (gm.) | 32.77 | 34.21 | 33.72 | 31.93 |
| Percent Yield | 69.5 | 64.0 | 70.2 | 66.5 |
| Boiling Range(°C.) | 183 to 193 | 175 to 181 | 187 to 196 | 183 to 189 |

EXAMPLE 19

Part B

Following the procedure of Example 1, Part B, but substituting the precursor, dimethylester of 4-(p-bromophenyl)-4-cyanopimelic acid (prepared in Part A, above) for the 34.97 gm. of the dimethyl ester of 4-(p-chlorophenyl)-4-cyanopimelic acid and modifying other factors of the procedure as noted in Table B, there is prepared the corresponding first intermediate 4-(p-bromophenyl)-2-carbomethoxy-4-cyanocyclohexanone as crystals having a melting range at 164° to 166° C.

Analysis: Calc'd. for $C_{15}H_{14}BrNO_3$: C, 53.59; H, 4.20; N, 4.51. Found: C, 53.49; H, 4.46; N, 4.29.

EXAMPLE 20

Part B

Following the procedure of Example 1, Part B, but substituting the precursor, dimethyl ester of 4-(m-chlorophenyl)-4-cyanopimelic acid (prepared in Part A, above) for the 34.97 gm. of the dimethyl ester of 4-(p-chlorophenyl)-4-cyanopimelic acid and modifying other factors of the procedure as noted in Table B, there is prepared the corresponding first intermediate, 2-carbomethoxy-4-(m-chlorophenyl)-4-cyanocyclohexanone as crystals having a melting point at 123.5° to 125.0° C.

Analysis: Calc'd. for $C_{15}H_{14}ClNO_3$: C, 61.75; H, 4.84; N, 4.80. Found: C, 61.52; H, 4.96; N, 4.86.

EXAMPLE 21

Part B

Following the procedure of Example 1, Part B, but substituting the precursor, dimethyl ester of 4-(3,4- dichlorophenyl)-4-cyanopimelic acid (prepared in Part A, above) for the 34.97 gm. of the dimethyl ester of 4-(p-chlorophenyl)-4-cyanopimelic acid and modifying other factors of the procedure as noted in Table B, there is prepared the corresponding first intermiedate 2-carbomethoxy-4-(3,4-dichlorophenyl)-4-cyanocyclohexanone as crystals having a melting range at 82° to 87° C. An analytical sample recrystallized from diethyl ether has a melting point at 112° to 113° C.

Analysis: Calc'd. for $C_{15}H_{13}Cl_2NO_3$: C, 55.23; H, 4.12; N, 4.30. Found: C, 55.47; H, 4.07; N, 4.48.

EXAMPLE 22

Part B

Following the procedure of Example 1, Part B, but substituting the precursor, dimethyl ester of 4-(2,4-dichlorophenyl)-4-cyanopimelic acid (prepared in Part A, above) for the 34.97 gm. of the dimethyl ester of 4-(p-chlorophenyl)-4-cyanopimelic acid and modifying other factors of the procedure as noted in Table B, there is prepared the corresponding first intermediate 2-carbomethoxy-4-(2,4-dichlorophenyl)-4-cyanocyclohexanone as a gum.

EXAMPLE 20

Part C

Following the procedure of Example 1, Part C, but substituting the first intermediate, 2-carbomethoxy-4-(m-chlorophenyl)-4-cyanocyclohexanone (prepared in Part B, above) for the 29.8 gm. of the 2-carbomethoxy-4-(p-chlorophenyl)-4-cyanocyclohexanone and modifying other factors of the procedure as noted in Table C, there is prepared the corresponding second intermediate, 4-(m-chlorophenyl)-4-cyanocyclohexanone as crystals having a melting range at 71° to 73.5° C.

Analysis: Calc'd. for $C_{13}H_{12}ClNO$; C, 66.81; H, 5.18; N, 5.99. Found: C, 66.91; H, 5.11; N, 5.95.

EXAMPLE 21

Part C

Following the procedure of Example 1, Part C, but substituting the first intermediate, 2-carbomethoxy-4-(3,4-dichlorophenyl)-4-cyanocyclohexanone, (prepared in Part B, above) for the 29.8 gm. of the 2-carbomethoxy-4-(p-chlorophenyl)-4-cyanocyclohexanone and modifying other factors of the procedure as noted in Table C, there is prepared the corresponding second intermediate, 4-(3,4-dichlorophenyl)-4-cyanocyclohexanone as crystals having a melting point at 156° to 157.5° C.

Analysis: Calc'd. for $C_{13}H_{11}Cl_2CO$: C, 58.22; H, 4.14; N, 5.22. Found: C, 58.61; H, 4.37; N, 5.50.

TABLE B

| Factor in Procedure | Example 19 | Example 20 | Example 21 | Example 22 |
| --- | --- | --- | --- | --- |
| Weight of Precursor (gm.) | 32.77 | 34.21 | 33.22 | 31.93 |
| Molar Amount | (0.089) | (0.106) | (0.0928) | (0.89) |
| Tetrahydrofuran (ml.) | 750 | 700 | 600 | 575 |
| Potassium tert-butoxide (gm.) | 20.0 | 23.9 | 21.0 | 20.2 |
| Molar Amount | (0.178) | (0.213) | (0.187) | (0.187) |
| Heating time (hours) | 5 | 5 | 5 | 5 |
| 2.5 N Acetic Acid (ml.) | 143 | 170 | 150 | 140 |
| Recrystallization solvent | Acetone + technical hexane | methylene chloride + technical hexane | diethyl ether | — |
| Yield of first Intermediate (gm.) | 20.18 | 23.47 | 31.4 | — |
| Percent Yield | (67.4) | (75.9) | — | — |

EXAMPLE 19

Part C

Following the procedure of Example 1, Part C, but substituting the first intermediate 4-(p-bromophenyl)-2-carbomethoxy-4-cyanocyclohexanone, (prepared in Part B, above) for the 29.8 gm. of the 2-carbomethoxy-4-(p-chlorophenyl)-4-cyanocyclohexanone and modifying other factors of the procedure as noted in Table C, there is prepared the corresponding second intermediate 4-(p-bromophenyl)-4-cyanocyclohexanone as crystals having a melting range at 110° to 113° C.

Analysis: Calc'd. for $C_{13}H_{12}BrNO$: C, 56.13; H, 4.35; N, 5.04. Found: C, 56.35; H, 4.34; N, 5.06.

EXAMPLE 22

Part C

Following the procedure of Example 1, Part C, but substituting the first intermediate 2-carbomethoxy-4-(2,4-dichlorophenyl)-4-cyanocyclohexanone (prepared in Part B, above) for the 29.8 gm. of the 2-carbomethoxy-4-(p-chlorophenyl)-4-cyanocyclohexanone and modifying other factors of the procedure as noted in Table C, there is prepared the corresponding second intermediate 4,(2,4-dichlorophenyl)-4-cyanocyclohexanone as crystals having a melting range at 119° to 122.5° C.

Analysis: Calc'd. for $C_{13}H_{11}Cl_2NO$: C, 58.22; H, 4.14; N, 5.22. Found: C, 58.21; H, 3.95; N, 5.41.

TABLE C

| Factor in Procedure | Example 19 | Example 20 | Example 21 | Example 22 |
| --- | --- | --- | --- | --- |
| Weight of first Intermediate (gm.) | 20.18 | 23.0 | 30.9 | 32.0 |
| Molar amount | (0.06) | (0.079) | (0.095) | (0.098) |
| Vol. Glacial Acetic Acid (ml.) | 380 | 500 | 600 | 620 |
| Vol. 10% sulfuric acid (ml.) | 190 | 250 | 300 | 310 |
| Benzene extraction & solvent evaporation omitted | — | — | — | — |
| Recrystallization Solvent | methylene chloride + Technical | petroleum ether | methylene chloride + Technical | Methylene Chloride + Technical |

TABLE C-continued

| Factor in Procedure | Example 19 | Example 20 | Example 21 | Example 22 |
|---|---|---|---|---|
| | hexane | | hexane | hexane |
| Weight of Second Intermediate (gm.) | 11.71 | 10.05 | 14.72 | 14.24 |
| Percentage Yield | (70.2) | (54.4) | (57.8) | (54.2) |

EXAMPLE 19

Part D

Following the procedure of Example 1, Part D, but substituting the second intermediate, 4-(p-bromophenyl)-4-cyanocyclohexanone (prepared in Part C, above) for the 19.49 gm. of the 4-(p-chlorophenyl)-4-cyanocyclohexanone and modifying other factors of the procedure as noted in Table D, there is prepared the corresponding third intermediate, 4-(p-bromophenyl)-4-cyanocyclohexanone, ethylene ketal as crystals having a melting range at 127° to 131° C.

Analysis: Calc'd. for $C_{15}H_{16}H_{16}BrNO_2$: C, 55.91; H, 5.00; N, 4.35. Found: C, 55.78; H, 5.13; N, 4.39.

EXAMPLE 22

Part D

Following the procedure of Example 1, Part D, but substituting the second intermediate, 4-(2,4-dichlorophenyl)-4-cyanocyclohexanone (prepared in Part C, above) for the 19.49 gm. of the 4-(p-chlorophenyl)-4-cyanocyclohexanone and modifying other factors of the procedure as noted in Table D, there is prepared the corresponding third intermediate, 4-(2,4-dichlorophenyl)-4-cyanocyclohexanone, ethylene ketal as crystals having a melting range at 109.5° to 112.0° C.

Analysis: Calc'd. for $C_{15}H_{15}Cl_2NO_2$: C, 57.71; H, 4.84; N, 4.49. Found: C, 57.70; H, 4.81; N, 4.71.

TABLE D

| Factor in Procedure | Example 19 | Example 20 | Example 21 | Example 22 |
|---|---|---|---|---|
| Weight of second intermediate (gm.) | 11.71 | 9.95 | 14.62 | 14.14 |
| Molar amount | (0.042) | (0.0426) | (0.0546) | (0.053) |
| Vol. Ethylene Glycol (ml.) | 3.0 | 2.5 | 3.1 | 3.0 |
| Weight of p-toluene sulfonic acid (gm.) | 0.14 | 0.12 | 0.15 | 0.15 |
| Vol. Benzene (ml.) | 120 | 80.0 | 95.0 | 92.0 |
| Crystallization Solvent | cyclohexane | diethyl ether + petroleum ether | cyclohexane | methylene chloride + technical Hexane |
| Weight of third intermediate (gm.) | 13.05 | 10.78 | 16.42 | 15.14 |
| Percentage Yield | (96.4) | (91.1) | (96.3) | (91.5) |

EXAMPLE 20

Part D

Following the procedure of Example 1, Part D, but substituting the second intermediate, 4-(m-chlorophenyl)-4-cyanocyclohexanone (prepared in Part C, above) for the 19.49 gm. of the 4-(p-chlorophenyl)-4-cyanocyclohexanone and modifying other factors of the procedure as noted in Table D, there is prepared the corresponding third intermediate, 4-(m-chlorophenyl)-4-cyanocyclohexanone, ethylene ketal as crystals having a melting range at 68° to 71° C.

Analysis: Calc'd. for $C_{15}H_{16}ClNO_2$: C, 64.86; H, 5.81; N, 5.04. Found: C, 64.94; H, 5.91; N, 4.81.

EXAMPLE 21

Part D

Following the procedure of Example 1, Part D, but substituting the second intermediate, 4-(3,4-dichlorophenyl)-4-cyanocyclohexanone, (prepared in Part C, above) for the 19.49 gm. of the 4-(p-chlorophenyl)-4-cyanocyclohexanone and modifying other factors of the procedure as noted in Table D, there is prepared the corresponding third intermediate, 4-(3,4-dichlorophenyl)-4-cyanocyclohexanone, ethylene ketal as crystals having a melting range at 120.5° to 123° C.

Analysis: Calc'd. for $C_{15}H_{15}Cl_2NO_2$: C, 57.51; H, 4.84; N, 4.49. Found: C, 57.44; H, 5.05; N, 4.50.

EXAMPLE 19

Part E

Following the procedure of Example 1, Part E, but substituting the third intermediate, 4-(p-bromophenyl)-4-cyanocyclohexanone, ethylene ketal, (prepared in Part D, above) for the 21.87 gm. of the 4-(p-chlorophenyl)-4-cycnocyclohexanone, ethylene ketal and modifying other factors of the procedure as noted in Table E, there is prepared the corresponding fourth intermediate, 4-(p-bromophenyl)-4-carboxycyclohexanone, ethylene ketal as crystals having a melting range at 176° to 178° C.

Analysis: Calc'd. for $C_{15}H_{17}BrO_4$: C, 52.80; H, 5.02. Found: C, 53.40; H, 4.92.

EXAMPLE 20

Part E

Following the procedure of Example 1, Part E, but substituting the third intermediate, 4-(m-chlorophenyl)-4-cyanocyclohexanone, ethylene ketal, (prepared in Part D, above) for the 21.87 gm. of the 4-(p-chlorophenyl)-4-cyanocyclohexanone, ethylene ketal and modifying other factors of the procedure as noted in Table E, there is prepared the corresponding fourth intermediate, 4-carboxy-4-(m-chlorophenyl)cyclohexanone, ethylene ketal as crystals having a melting point at 140° to 141.5° C.

Analysis: Calc'd. for $C_{15}H_{17}ClO_4$: C, 60.71; H, 5.78. Found: C, 60.51; H, 5.78.

EXAMPLE 21

Part E

Following the procedure of Example 1, Part E, but substituting the third intermediate, 4-(3,4-dichlorophenyl)-4-cyanocyclohexanone, ethylene ketal (prepared in Part D, above) for the 21.87 gm. of the 4-(p-chlorophenyl)-4-cyanocyclohexanone, ethylene ketal and modifying other factors of the procedure as noted in Table E, there is prepared the corresponding fourth intermediate, 4-carboxy-4-(3,4-dichlorophenyl)cyclohexanone, ethylene ketal as crystals having a melting range at 119° to 121.5° C.

Analysis: Calc'd. for $C_{15}H_{16}Cl_2O_4$: C, 54.39; H, 4.87. Found: C, 54.69; H, 5.11.

EXAMPLE 22

Part D

Following the procedure of Example 1, Part E, but substituting the third intermediate, 4-(2,4-dichlorophenyl)-4-cyanocyclohexanone, ethylene ketal (prepared in Part D, above) for the 21.87 gm. of the 4-(p-chlorophenyl)-4-cyanocyclohexanone, ethylene ketal and modifying other factors of the procedure as noted in Table E, there is prepared the corresponding fourth intermediate, 4-carboxy-4-(2,4-dichlorophenyl)cyclohexanone, ethylene ketal as crystals having a melting range at 192° to 195.5° C.

Analysis: Calc'd. for $C_{15}H_{16}Cl_2O_4$: C, 54.39; H, 4.87. Found: C, 54.63; H, 5.03.

Analysis: Calc'd. for $C_{15}H_{16}BrNO_3$: C, 53.27; H, 4.77; N, 4.14. Found: C, 53.43; H, 4.89; N, 4.02.

EXAMPLE 20

Part F

Following the procedure of Example 1, Part F, but substituting the fourth intermediate, 4-carboxy-4-(m-chlorophenyl)cyclohexanone, ethylene ketal (prepared in Part E, above) for the 15.79 gm. of the 4-carboxy-4-(p-chlorophenyl)cyclohexanone, ethylene ketal and modifying other factors of the procedure as noted in Table F, there is prepared the corresponding fifth intermediate, 4-(m-chlorophenyl)-4-isocyanatocyclohexanone, ethylene ketal as a gum having an I.R. maximum at about 2290 cm.$^{-1}$.

EXAMPLE 21

Part F

Following the procedure of Example 1, Part F, but substituting the fourth intermediate, 4-carboxy-4-(3,4-dichlorophenyl)cyclohexanone, ethylene ketal (prepared in Part E, above) for the 15,79 gm. of the 4-carboxy-4-(p-chlorophenyl)cyclohexanone, ethylene ketal and modifying other factors of the procedure as noted in Table F, there is prepared the corresponding fifth intermediate, 4-(3,4-dichlorophenyl)-4-isocyanatocyclohexanone, ethylene ketal as an oil having an I.R. maximum at about 2250 cm.$^{-1}$.

TABLE E

| Factor in Procedure | Example 19 | Example 20 | Example 21 | Example 22 |
|---|---|---|---|---|
| Weight of third intermediate (gm.) | 13.05 | 10.78 | 16.32 | 15.04 |
| Molar Amount | (0.04) | (0.045) | (0.052) | (0.048) |
| Weight of Potassium Hydroxide (gm.) | (sodium hydroxide) 2.0 | 2.23 | 16.3 | 15.0 |
| Volume of Ethylene Glycol (ml.) | 100 | 100 | 165 | 150 |
| Extracting Solvent | diethyl ether | diethyl ether | methylene chloride | methylene chloride |
| Recrystallization Solvent | methylene chloride + technical hexane | methylene chloride + technical hexane | diethyl ether + petroleum ether | ethyl acetate |
| Weight of fourth Intermediate (gm.) | 12.56 | 10.49 | 13.69 | 11.25 |
| Percentage Yield | (92.0) | (78.6) | (79.5) | (70.8) |

EXAMPLE 19

Part F

Following the procedure of Example 1, Part F, but substituting the fourth intermediate, 4-(p-bromophenyl)-4-carboxycyclohexanone, ethylene ketal, (prepared in Part E, above) for the 15.79 gm. of the 4-carboxy-4-(p-chlorophenyl)cyclohexanone, ethylene ketal and modifying other factors of the procedure as noted in Table F, there is prepared the corresponding fifth intermediate, 4-(p-bromophenyl)-4-isocyanatocyclohexanone, ethylene ketal as crystals having a melting range at 87° to 89° C.

EXAMPLE 22

Part F

Following the procedure of Example 1, Part F, but substituting the fourth intermediate, 4-carboxy-4-(2,4-dichlorophenyl)cyclohexanone, ethylene ketal (prepared in Part E, above) for the 15.79 gm. of the 4-carboxy-4-(p-chlorophenyl)cyclohexanone, ethylene ketal and modifying other factors of the procedure as noted in Table F, there is prepared the corresponding fifth intermediate, 4-(2,4-dichlorophenyl)-4-isocyanatocyclohexanone, ethylene ketal as crystals having a melting range at 85° to 89.5° C.

Analysis: Calc'd. for $C_{15}H_{15}Cl_2NO_3$: C, 54.89; H, 4.61; N, 4.27. Found: C, 55.02; H, 4.61; N, 4.36.

TABLE F

| Factor in Procedure | Example 19 | Example 20 | Example 21 | Example 22 |
|---|---|---|---|---|
| Weight of fourth Intermediate (gm.) | 12.56 | 10.49 | 13.59 | 11.15 |
| Molar Amount | (0.038) | (0.035) | (0.041) | (0.034) |
| Volume of triethylamine (ml.) | 5.26 | 4.92 | 5.7 | 4.7 |
| Volume of anisole (ml.) | 100 | 100 | 105 | 85 |
| Weight of diphenylphosphonic | | | | |

TABLE F-continued

| Factor in Procedure | Example 19 | Example 20 | Example 21 | Example 22 |
|---|---|---|---|---|
| azide (gm.) | 10.46 | 9.76 | 11.45 | 9.40 |
| Volume of Silica gel in column (ml.) | 600 | 600 | 1000 | 600 |
| Developing solvent | methylene chloride | methylene chloride | ethyl acetate 1 pt:3 pts. methylene chloride | 1.5% ethyl acetate in methylene chloride |
| Recrystallization Solvent | diethyl ether + petroleum ether | — | — | diethyl ether + petroleum ether |
| Weight of fifth Intermediate (gm.) | 6.25 | 10.0 | 9.51 | 8.64 |
| Percentage Yield | — | (97.3) | (70.7) | (77.4) |

EXAMPLE 19

Part G

Following the procedure of Example 1, Part G, but substituting the fifth intermediate, 4-(p-bromophenyl)-4-isocyanatocyclohexanone, ethylene ketal (prepared in Part F, above) for the 6.62 gm. of the 4-(p-chlorophenyl)-4-isocyanatocyclohexanone, ethylene ketal, modifying other factors of the procedure as noted in Table G, and including the additional step of dissolving the residue from the filtrate into a small amount of diethyl ether and treating this solution with sufficient 3 N hydrogen chloride in ether to form the hydrochloride acid addition salt, there is prepared the corresponding sixth intermediate, 4-(p-bromophenyl)-4-methylaminocyclohexanone, ethylene ketal hydrochloride as crystals having a melting point at 266° to 267° C.

Analysis: Calc'd. for $C_{15}H_{21}BrClNO_2$: C, 48.99; H, 5.76; N, 3.81. Found: C, 48.59; H, 5.46; N, 3.63.

EXAMPLE 20

Part G

Following the procedure of Example 1, Part G, but substituting the fifth intermediate, 4-(2,4-dichlorophenyl)-4-isocyanatocyclohexanone, ethylene ketal (prepared in Part F, above) for the 6.62 gm. of the 4-(p-chlorophenyl)-4-isocyanatocyclohexanone, ethylene ketal, modifying other factors of the procedure as noted in Table G, and including the additional step of dissolving the residue from the filtrate into a small amount of diethyl ether and treating this solution with sufficient 3 N hydrogen chloride in ether to form the hydrochloride acid addition salt, there is prepared the corresponding sixth intermediate 4-(m-chlorophenyl)-4-methylaminocyclohexanone, ethylene ketal hydrochloride as crystals having a melting range at 252° to 254° C.

Analysis: Calc'd. for $C_{15}H_{21}Cl_2NO_2$: C, 56.61; H, 6.65; N, 4.40. Found: C, 56.74; H, 6.68; N, 4.64.

EXAMPLE 21

Part G

Following the procedure of Example 1, Part G, but substituting the fifth intermediate, 4-(3,4-dichlorophenyl)-4-isocyanatocyclohexanone, ethylene ketal (prepared in Part G, above) for the 6.62 gm. of the 4-(p-chlorophenyl)-4-isocyanatocyclohexanone, ethylene ketal, modifying other factors of the procedure as noted in Table G, and including the additional step of dissolving the residue from the filtrate into a small amount of diethyl ether and treating this solution with sufficient 3 N hydrogen chloride in ether to form the hydrochloride acid addition salt, there is prepared the corresponding sixth intermediate, 4-(3,4-dichlorophenyl)-4-methylaminocyclohexanone, ethylene ketal hydrochloride as crystals having a melting range at 225° to 27° C.

Analysis: Calc'd. for $C_{15}H_{20}Cl_3NO_2$: C, 51.08; H, 5.72; N, 3.97. Found: C, 51.49; H, 5.91; N, 4.20.

EXAMPLE 22

Part G

Following the procedure of Example 1, Part G, but substituting the fifth intermediate, 4-(2,4-dichlorophenyl)-4-isocyanatocyclohexanone, ethylene ketal (prepared in Part F, above) for the 6.62 gm. of the 4-chlorophenyl)-4-isocyanatocyclohexanone, ethylene ketal, modifying other factors of the procedure as noted in Table G, and including the additional step of dissolving the residue from the filtrate into a small amount of diethyl ether and treating this solution with sufficient 3 N hydrogen chloride in ether to form the hydrochloride acid addition salt, there is prepared the corresponding sixth intermediate, 4-(2,4-dichlorophenyl)-4-methylaminocyclohexanone, ethylene ketal hydrochloride as crystals having a melting range at 201° to 2.305° C.

Analysis: Calc'd. for $C_{15}H_{20}Cl_3NO_2 \cdot \frac{1}{4}H_2O$: C, 50.22; H, 5.62; N, 3.91. Found: C, 50.42; H, 5.92; N, 3.80.

TABLE G

| Factor in Procedure | Example 19 | Example 20 | Example 21 | Example 22 |
|---|---|---|---|---|
| Weight of fifth intermediate (gm.) | 6.25 | 10.0 | 9.51 | 8.54 |
| Molar amount | (0.018) | (0.034) | (0.029) | (0.026) |
| Volume of tetrahydrofuran (ml.) | 80 | 150 | 135 | 120 |
| Lithium Aluminum hydride (gm.) | 1.0 | 1.5 | 1.67 | 1.5 |
| Second volume of tetrahydrofuran (ml.) | 20 | 20 | 13 | 12 |
| First volume of water (ml.) | 1.0 | 1.5 | 1.7 | 1.5 |
| Volume of 15% sodium Hydroxide (ml.) | 1.0 | 1.5 | 1.7 | 1.5 |
| Second volume of water (ml.) | 3.0 | 1.5 | 5.1 | 4.5 |
| Recrystallization Solvent | methylene | methylene | methanol | methylene |

TABLE G-continued

| Factor in Procedure | Example 19 | Example 20 | Example 21 | Example 22 |
|---|---|---|---|---|
| | chloride + ethyl acetate | chloride + ethyl acetate | + diethyl ether | chloride + ethyl acetate |
| Weight of sixth intermediate (gm.) | 4.30 | 6.09 | 4.70 | 6.25 |
| Percentage Yield | (68.5) | (56.3) | (46.0) | (68.2) |

EXAMPLE 19

Part H

Following the procedure of Example 1, Part H, but substituting the free base from the sixth intermediate, 4-(p-bromophenyl)-4-methylaminocyclohexanone, ethylene ketal hydrochloride, (prepared in Part G, above) for the 4.68 gm. of the 4-(p-chlorophenyl)-4-methylaminocyclohexanone, ethylene ketal free base, and modifying other factors of the procedure as noted in Table H, there is prepared the corresponsing object compound, 4-(p-bromophenyl)-4-dimethylaminocyclohexanone, ethylene ketal hydrochloride as crystals having a melting point at 254° to 255.5° C.

Analysis:
Calc'd. for $C_{16}H_{23}BrClNO_2$: C, 51.01; H, 6.14; N, 3.72. Found: C, 51.29; H, 6.30; N, 3.85.

EXAMPLE 20

Part H

Following the procedure of Example 1, Part H, but substituting the free base from the sixth intermediate, 4-(m-chlorophenyl)-4-methylaminocyclohexanone, ethylene ketal hydrochloride, (prepared in Part G, above) for the 5.68 gm. of the 4-(p-chlorophenyl)-4-methylaminocyclohexanone, ethylene ketal free base and modifying other factors of the procedure as noted in Table H, there is prepared the corresponding object compound, 4-(m-chlorophenyl)-4-dimethylaminocyclohexanone, ethylene ketal hydrochloride as crystals having a melting range at 224° to 227° C.

Analysis: Calc'd. for $C_{16}H_{23}Cl_2NO_2$: C, 57.83; H, 6.98; N, 4.22. Found: C, 57.71; H, 7.03; N, 4.31.

EXAMPLE 21

Part H

Following the procedure of Example 1, Part H, but substituting the free base from the sixth intermediate, 4-(3,4-dichlorophenyl)-4-methylaminocyclohexanone, ethylene ketal hydrochloirde (prepared in Part G, above) for the 5.68 gm. of the 4-(p-chlorophenyl)-4-methylaminocyclohexanone, ethylene ketal free base and modifying other factors of the procedure as noted in Table H, there is prepared the corresponding object compound, 4-(3,4-dichlorophenyl)-4-dimethylaminocyclohexanone, ethylene ketal as crystals having a melting range at 77° to 81° C.

Analysis: Calc'd. for $C_{16}H_{21}NO_2$: C, 58.19; H, 6.41; N, 4.24. Found: C, 58.30; H, 6.38; N, 4.48.

EXAMPLE 22

Part H

Following the procedure of Example 1, Part H, but substituting the free base from the sixth intermediate, 4-(2,4-dichlorophenyl)-4-methylaminocyclohexaone, ethylene ketal hydrochloride, (prepared in Part G, above) for the 5.68 gm. of the 4-(p-chlorophenyl)-4-methylaminocyclohexanone, ethylene ketal free base and modifying other factors of the procedure as noted in Table H, there is prepared the corresponding object compound, 4-(2,4-dichlorophenyl)-4-dimethylaminocyclohexanone, ethylene ketal hydrochloride as crystals having a melting range at 229.5° to 232° C.

Analysis: Calc'd. for $C_{16}H_{22}Cl_3NO_2.\tfrac{1}{2}H_2O$: C, 51.14; H, 6.17; N, 3.73. Found: C, 51.47; H, 6.28; N, 3.99.

TABLE H

| Factor in Procedure | Example 19 | Example 20 | Example 21 | Example 22 |
|---|---|---|---|---|
| Weight of sixth intermediate (gm.) | 4.30 | 6.09 | 4.6 | 6.15 |
| Molar amount | (0.013) | (0.019) | (0.013) | (0.017) |
| Volume of 37% Formalin (ml.) | 18 | 27 | 14.2 | 18.9 |
| Volume of methanol (ml.) | 54 | 80 | 48 | 64 |
| Weight of sodium borohydride (gm.) | 2.86 | 3.83 | 1.93 | 2.57 |
| Recrystallization Solvent | methylene chloride + ethyl acetate | methylene chloride + ethyl acetate | ether + petroleum ether | methylene chloride + ethyl acetate |
| Weight of object compound (gm.) | 2.40 | 3.29 | 2.22* | 2.51 |
| Percentage Yield | (50.9) | (52.1) | (51.3) | (40.3) |

*This compound was not prepared as the hydrochloride acid addition salt. The procedure is modified by merely omitting the step of adding 2.5 N hydrogen chloride in ether.

EXAMPLE 23

Following the procedure as described in Example 2, but separately substituting the object compound, 4-(p-bromophenyl)-4-dimethylaminocyclohexanone, ethylene ketal hydrochloride (prepared in Example 19, Part H, above) for the 4.52 gm. of the 4-(p-chlorophenyl)-4-dimethylaminocyclohexanone, ethylene ketal hydrochloride and modifying other factors of the procedure as noted in Table J, there is prepared the corresponding further object compound, 4-(p-bromophenyl)-4-dimethylaminocyclohexanone as crystals having a melting range at 115° to 118° C.

Analysis: Calc'd. for $C_{14}H_{18}BrNO$: C, 56.76; H, 6.12; N, 4.73. Found: C, 56.79; H, 6.14; N, 4.91.

EXAMPLE 24

Following the procedure as described in Example 2, but substituting the object compound, 4-(m-chlorophenyl)-4-dimethylaminocyclohexanone, ethylene ketal hydrochloride (prepared in Example 20, Part H, above)

for the 4.52 gm. of the 4-(p-chlorophenyl)-4-dimethylaminocyclohexanone, ethylene ketal hydrochloride and modifying other factors of the procedure as noted in Table J, there is prepared the corresponding further object compound, 4-(m-chlorophenyl)-4-dimethylaminocyclohexanone, as crystals having a melting range at 93° to 95° C.

Analysis: Calc'd. for $C_{14}H_{18}ClNO$: C, 66.79; H, 7.21; N, 5.59. Found: C, 67.35; H, 7.33; N, 5.87.

EXAMPLE 25

Following the procedure as described in Example 2, but substituting the object compound, 4-(3,4-dichlorophenyl)-4-dimethylaminocyclohexanone, ethylene ketal hydrochloride (prepared in Example 21, Part H, above) for the 4.52 gm. of the 4-(p-chlorophenyl)-4-dimethylaminocyclohexanone, ethylene ketal hydrochloride and modifying other factors of the procedure as noted in Table J, there is prepared the corresponding further object compound, 4-(3,4-dichlorophenyl)-4-dimethylaminocyclohexanone as crystals having a melting range at 88.5° to 91° C.

Analysis: Calc'd. for $C_{14}H_{17}Cl_2NO$: C, 58.75; H, 5.99; N, 4.99. Found: C, 59.02; H, 6.14; N, 5.22.

EXAMPLE 26

Following the procedure as described in Example 2, but substituting the object compound, 4-(2,4-dichlorophenyl)-4-dimethylaminocyclohexanone, ethylene ketal hydrochloride (prepared in Example 22, Part H, above) for the 4.52 gm. of the 4-(p-chlorophenyl)-4-dimethylaminocyclohexanone, ethylene ketal hydrochloride and modifying other factors of the procedure as noted in Table J, there is prepared the corresponding further object compound, 4-(2,4-dichlorophenyl)-4-dimethylaminocyclohexanone, as crystals having a melting range at 116.5° to 120° C.

Analysis: Calc'd. for $C_{14}H_{17}Cl_2NO$: C, 58.75; H, 5.99; N, 4.90. Found: C, 58.84; H, 6.25; N, 4.87.

brine and taken to dryness. The residue is distilled first at 40 mm Hg to remove low-boiling by-products, then at 0.05 mm Hg to afford the product as an oil. There is obtained 7.70 g. (73%) of pimelate, boiling point 162°-180° C.

Part B: Preparation of 4-(2-thienyl)-4-cyano-2-carbomethoxycyclohexanone

To a solution of 8.80 g. (0.0298 mole) of dimethyl-4-(2-thienyl)-4-cyanopimelate (prepared in Part A, above) in 200 ml. THF there is added 6.70 g. (0.06 mole) of potassium tert-butoxide. Following 4.5 hours' heating at reflux the mixture is cooled in ice and treated with 47 ml. 2.5 N acetic acid. The organic layer is separated and diluted with benzene. That solution is washed in turn with aqueous sodium bicarbonate ($NaHCO_3$), water and brine and taken to dryness. There is obtained 8.0 g. (99%) of 4-(2-thienyl)-4-cyano-2-carbomethoxycyclohexanone as a crystalline material, m.p. 76°-78° C.

Analysis: Calc'd. for $C_{13}H_{13}NO_3S$: C, 59.30; H, 4.98; N, 5.32. Found: C, 59.16; H, 5.13; N, 5.19.

Part C: Preparation of 4-(2-thienyl)-4-cyanocyclohexanone

A mixture of 8.0 g. (0.0304 mole) of 4-(2-thienyl)-4-cyano-2-carbomethoxycyclohexanone in 200 ml. acetic acid and 100 ml. 10% aqueous sulfuric acid is heated on the steam bath with mechanical stirring for 24 hours. The mixture is then allowed to cool, diluted with water and extracted thoroughly with benzene. The organic layer is washed in turn with water, aqueous sodium bicarbonate and brine and taken to dryness. The residual solid is recrystallized from methylene chloride:Skellysolve B to afford 4.10 g. (66% yield) of 4-(2-thienyl)-4-cyanocyclohexanone, m.p. 117.5°-119° C.

Analysis: Calc'd. for $C_{11}H_{11}NOS$: C, 64.36; H, 5.40; N, 6.82. Found: C, 64.75; H, 5.49; N, 6.85.

TABLE J

| Factor in Procedure | Example 23 | Example 24 | Example 25 | Example 26 |
| --- | --- | --- | --- | --- |
| Weight of Starting Compound (gm.) | 1.40 | 2.28 | 1.72 | 1.76 |
| Molar Amount | (0.0039) | (0.0069) | (0.0052) | (0.0048) |
| Volume of 2.5 N Hydrochloric Acid (ml.) | 7.0 | 11.5 | 8.5 | 9.0 |
| Volume of methanol (ml.) | 14 | 23 | 17 | 18 |
| Recrystallization Solvent | acetone + technical hexane | diethyl ether + petroleum ether | diethyl ether + petroleum ether | diethyl ether |
| Weight of object Compound (gm.) | 0.80 | 1.41 | 1.00 | 0.94 |
| Percentage Yield | (69) | (81.2) | (71.7) | (68.4) |

EXAMPLE 27

Preparation of 4-dimethylamino-4-(2-thienyl)cyclohexanone, ethylene ketal

Part A: Preparation of Dimethyl 4-(2-thienyl)-4-cyanopimelate

A mixture of 5.0 g. (0.406 mole) of 2-thiophene acetonitrile and 19 ml. of methyl acrylate in 20 ml. t-butyl alcohol is brought to reflux. The heat is removed and there is added quickly 6.5 ml. of 40% methanolic Triton B® in 9 ml. t-butyl alcohol. Following 4 hours heating at reflux the mixture is allowed to cool and diluted with water and benzene. The organic layer is separated, washed in turn with 2.5 N hydrochloric acid, water and

Part D: Preparation of 4-(2-thienyl)-4-cyanocyclohexanone, ethylene ketal

A mixture of 4.0 g. (0.0195 mole) of 4-(2-thienyl)-4-cyanocyclohexanone, 1.2 ml. (1.32 g., 0.02 mole) ethylene glycol and 0.05 g. p-toluenesulfonic acid in 35 ml. benzene is heated at reflux under a Dean-Stark trap for 6 hours. The solution is then allowed to cool, washed in turn with aqueous sodium bicarbonate, water and brine and taken to dryness. The residual solid is recrystallized from benzene to give 4.38 g. (90% yield) of 4-(2-thienyl)-4-cyanocyclohexanone, ethylene ketal, m.p. 90.5°-92° C.

Analysis: Calc'd. for $C_{13}H_{15}NO_2S$: C, 62.62; H, 6.06; N, 5.62. Found: C, 62.47; H, 5.99; N, 5.71.

Part E: Preparation of 4-carboxy-4-(2-thienyl)cyclohexanone, ethylene ketal

A mixture of 4.98 g. (0.02 mole) of 4-cyano-4-(2-thienyl)cyclohexanone ethylene ketal and 0.70 g. (0.02 mole) of sodium hydroxide in 40 ml. ethylene glycol is heated overnight at reflux. The mixture is allowed to cool and diluted with water. The solution is then cooled in ice, covered with ether and cautiously acidified. The organic layer is separated and the aqueous layer is washed twice more with ether. The extracts are combined, washed once with brine and taken to dryness. The residual solid is recrystallized from methylene chloride:Skellysolve B to afford 4.64 g. (82% yield) of 4-carboxy-4-(2-thienyl)cyclohexanone, ethylene ketal, m.p. 125°–127° C.

Analysis: Calc'd. for $C_{13}H_{16}O_4S$: C, 58.19; H, 6.01. Found: C, 58.38; H, 5.93.

Part F: Preparation of 4-isocyanato-4-(2-thienyl)cyclohexanone, ethylene ketal To a mixture of 4.64 g. (0.017 mole) of 4-carboxy-4-(2-thienyl)cyclohexanone ethylene ketal and 2.4 ml. (1.75 g., 0.017 mole) triethylamine in 60 ml. anisole there is added 4.68 g. diphenylphosphonic azide. The mixture is then stirred in an oil bath at 90°–100° C. for 2 hours; the solvent is removed under oil pump vacuum. The residual gum is chromatographed on 400 ml. silica gel (elution with 5% ethyl acetate:Skellysolve B). The appropriate fractions are combined to give 1.28 g. (28%) of crude isocyanate as a mobile oil; (Infrared absorption: γmax 2280 cm$^{-1}$).

Part G: Preparation of 4-methylamino-4-(2-thienyl)cyclohexanone, ethylene ketal hydrochloride A solution of 2.21 g. (8.3 mmole) of 4-isocyanato-4-(2-thienyl)cyclohexanone ethylene ketal in 40 ml. tetrahydrofuran (THF) is added to a suspension of 0.32 g. (8.4 mmole) of lithium aluminum hydride (LAH) in 5 ml. THF. Following 4 hours' stirring under reflux the mixture is cooled in ice. There is then added in turn 0.32 ml. water, 0.32 ml. 15% NaOH and 0.96 ml. water. The inorganic gel is collected on a filter and the filtrate taken to dryness. A solution of the residue in a small amount of ether is treated with a just-sufficient amount of 3 N hydrogen chloride in ether. The precipitated salt is recrystallized from methylene chloride:ethyl acetate to afford 0.84 g. (35% yield) of 4-methylamino-4-(2-thienyl)cyclohexanone, ethylene ketal hydrochloride, m.p. 211°–214° C.

Analysis: Calc'd. for $C_{13}H_{20}ClNO_2S$: C, 53.87; H, 6.96; N, 4.83. Found: C, 53.47; H, 6.81; N, 5.04.

Part H: Preparation of object compound, 4-dimethylamino-4-(2-thienyl)cyclohexanone, ethylene ketal A solution of the free base from 0.84 g. (2.9 mmole) of 4-methylamino-4-(2-thienyl)cyclohexanone ethylene ketal hydrochloride and 2.2 ml. 37% formalin in 6.6 ml. methanol is heated at reflux for 4 hours. The mixture is cooled in ice and treated cautiously in small portion with 0.27 g. (7.1 mmole) sodium borohydride. Following 2 hours' stirring at room temperature the bulk of the solvent is removed in vacuum. The residue is taken up in methylene chloride and water. The organic layer is washed with water and brine and taken to dryness. The residue is recycled twice through the same reaction conditions and workup. The solid which is finally obtained is recrystallized twice from ether (cooling in Dry-Ice:acetone) to afford 0.14 g. (18% yield) of 4-dimethylamino-4-(2-thienyl)cyclohexanone, ethylene ketal, m.p. 99°–103° C.

Analysis: Calc'd. for $C_{14}H_{21}NO_2S$: C, 62.88; H, 7.92; N, 5.24. Found: C, 62.75; H, 8.21; N, 5.49.

EXAMPLE 28

Preparation of 4-dimethylamino-4-(2-thienyl)cyclohexanone

Following the procedure of Example 2, but substituting the appropriate quantity of 4-dimethylamino-4-(2-thienyl)cyclohexanone ethylene ketal (prepared above in Example 27H) for the 4-(p-chlorophenyl)-4-dimethylaminocyclohexanone, ethylene ketal hydrochloride there is prepared (after recrystallization from methanol-water) the title compound in 64% yield, m.p. 102°–103° C.

Analysis: Calc'd. for $C_{12}H_{17}NOS$: C, 64.53; H, 7.67; N, 6.27. Found: C, 64.41; H, 7.76; N, 5.94.

EXAMPLE 29

Alternate preparation of 4-methylamino-4-(2-thienyl)cyclohexanone ethylene ketal hydrochloride

Part A: Preparation of precursor, 4-(2-thienyl)-4-ethoxycarbonylaminocyclohexanone ethylene ketal To a solution of 2.68 g. (0.010 mole) of 4-carboxy-4-(2-thienyl)cyclohexanone ethylene ketal and 1.39 ml. triethylamine in 40 ml. ethanol there is added 2.75 g. diphenylphosphonic azide. Following 5 hours' heating at reflux the bulk of the solvent is removed in vacuum. The residue is dissolved in water and ether:benzene. The organic layer is washed in turn with water, ice cold 2.5 N hydrochloric acid, water, saturated sodium bicarbonate and brine and taken to dryness. The residual solid is recrystallized from cyclohexane to give 1.58 g. (51% yield) of 4-(2-thienyl)-4-ethoxycarbonylaminocyclohexanone ethylene ketal, m.p. 113°–117° C.

Analysis: Calc'd. for $C_{15}H_{21}NO_4S$: C, 57.85; H, 6.80; N, 4.50. Found: C, 57.50; H, 6.79; N, 4.55.

Part B: Preparation of 4-methylamino-4-(2-thienyl)cyclohexanone ethylene ketal hydrochloride To a suspension of 2.0 g. of lithium aluminum hydride in 50 ml. of THF (tetrahydrofuran) is added a solution of 11.58 g. (0.037 mole) of 4-(2-thienyl)-4-ethoxycarbonylaminocyclohexanone ethylene ketal (prepared in Part A, above) in 150 ml. of THF. The reaction mixture is heated at reflux temperature for 5 hours, and then is cooled. To this cooled reaction mixture are added, in order, 2 ml. H$_2$O, 2 ml. 15% NaOH, and 6 ml. H$_2$O. The inorganic gel which accumulates is filtered off and the filtrate is taken to dryness. The residue is dissolved in ether and a just-sufficient volume of 2.5 N HCl in ether is added to give the title compound. Recrystallization is effected from methylene chloride-ethyl acetate to give 7.25 g. of the 4-methylamino-4-(2-thienyl)cyclohexanone ethylene ketal hydrochloride, m.p. 212°–214° C.

EXAMPLE 30

Preparation of 4-(p-t-butylphenyl)-4-dimethylaminocyclohexanone

Part A: 4-p-t-butylphenyl-4-isocyanatocyclohexanone ethylene ketal

Following the procedure of Example 1, Parts A–F, but initially substituting p-t-butylphenylacetonitrile (prepared as in the "Preparation" above) for p-chlorophenylacetonitrile, and substituting appropriate quantities of each appropriate corresponding intermediate subsequently in each step, there is obtained a 71% yield of 4-p-t-butylphenyl-4-isocyanatocyclohexanone ethylene ketal, on elution from a silica gel column with a 2:1 mixture of ethyl acetate in methylene chloride, and recrystallization from Skellysolve B, m.p. 103°–105.5° C.

Analysis: Calc'd. for $C_{19}H_{25}NO_3$: C, 72.35; H, 7.99; N, 4.44. Found: C, 72.66; H, 8.03; N, 4.50.

Part B: Preparation of 4-(p-t-butylphenyl)-4-methylaminocyclohexanone ethylene ketal Following the procedure of Example 1, Part G, but substituting an appropriate quantity of 4-(p-t-butylphenyl)-4-isocyanatocyclohexanone ethylene ketal for 4-p-chlorophenyl-4-isocyanatocyclohexanone there is obtained 4-(p-t-butylphenyl)-4-methylaminocyclohexanone ethylene ketal which as a m.p. 118.5°–121° C. (94% yield).

Analysis: Calc'd. for $C_{19}H_{29}NO_2$: C, 75.20; H, 9.63; N, 4.62. Found: C, 75.32; H, 9.92; N, 4.15.

Part C: Preparation of 4-(p-t-butylphenyl)-4-dimethylaminocyclohexanone ethylene ketal Following the procedure of Example 1, Part H, but substituting 4-methylamino-4-(p-t-butylphenyl)cyclohexanone ethylene ketal (Part B, above) for 4-(p-chlorophenyl)-4-methylaminocyclohexanone ethylene ketal there is obtained 4-(p-t-butylphenyl)-4-dimethylaminocyclohexanone ethylene ketal in 90% yield, m.p. 103.5°–107° C.

Analysis: Calc'd. for $C_{20}H_{31}NO_2$: C, 75.66; H, 9.84; N, 4.41. Found: C, 75.49; H, 9.73; N, 4.68.

Part D: Preparation of 4-(p-t-butylphenyl)-4-dimethylaminocyclohexanone

Following the procedure of Example 2, but substituting 4-(p-t-butylphenyl)-4-dimethylaminocyclohexanone ethylene ketal (Part C, above) for 4-(p-chlorophenyl)-4-dimethylaminocyclohexanone ethylene ketal hydrochloride there is obtained a 60% yield of the 4-(p-t-butylphenyl)-4-dimethylaminocyclohexanone after recrystallization from petroleum ether, m.p. 82.5°–87° C.

Analysis: Calc'd. for $C_{18}H_{27}NO$: C, 79.07; H, 9.96; N, 5.12. Found: C, 78.85; H, 10.05; N, 4.85.

EXAMPLE 31

Preparation of 4-(m-tolyl)-4-dimethylaminocyclohexanone

Part A: Preparation of 4-(m-tolyl)-4-isocyanatocyclohexanone ethylene ketal

Following the procedure of Example 15, parts A–F, but initially substituting m-tolylacetonitrile for o-tolylacetonitrile and subsequently substituting each intermediate appropriately and in appropriate quantities, there is obtained a 90% yield of 4-(m-tolyl)-4-isocyanatocyclohexanone ethylene ketal as an oil. (Infrared absorption $\bar{\nu}$ at 2250–2270 cm$^{-1}$) eluted from a silica gel column with methylene chloride instead of 2% ethyl acetate in methylene chloride.

Part B: Preparation of 4-(m-tolyl)-4-methylaminocyclohexanone ethylene ketal hydrochloride Following the procedure of Example 15, Part G, but substituting 4-isocyanato-4-(m-tolyl)cyclohexanone ethylene ketal for 4-isocyanato-4-(o-tolyl)cyclohexanone ethylene ketal there is obtained a 58% yield of 4-(m-tolyl)-4-methylaminocyclohexanone ethylene ketal hydrochloride, m.p. 219°–221° C.

Analysis: Calc'd. for $C_{16}H_{24}ClNO_2$: C, 64.52; H, 8.12; N, 4.70. Found: C, 64.35; H, 8.18; N, 4.93.

Part C: Preparation of 4-(m-tolyl)-4-dimethylamino cyclohexanone ethylene ketal hydroiodide Following the procedure of Example 15, Part H, but substituting 4-(m-tolyl)-4-methylaminocyclohexanone ethylene ketal hydrochloride for 4-(o-tolyl)-4-methylaminocyclohexanone ethylene ketal hydrochloride there is obtained an 85% yield of 4-(m-tolyl)-4-dimethylaminocyclohexanone ethylene ketal hydroiodide, m.p. 214°–215.5° C.

Analysis: Calc'd. for $C_{17}H_{26}INO_2$: C, 50.62; H, 6.50; N, 3.47. Found: C, 50.60; H, 6.58; N, 3.59.

Part D: Preparation of the object compound 4-(m-tolyl)-4-dimethylaminocyclohexanone hydroiodide salt Following the procedure of Example 16, but substituting 4-(m-tolyl)-4-dimethylaminocyclohexanone ethylene ketal hydroiodide for the 4-(o-tolyl)-4-dimethylaminocyclohexanone ethylene ketal hydroiodide there is obtained the 4-(m-tolyl)-4-dimethylaminocyclohexanine hydroiodide salt in 75% yield after recrystallization from methylene chloride:ethyl acetate; m.p. 172°–174.5° C.

Analysis: Calcd'd. for $C_{15}H_{22}INO$: C, 50.15; H, 6.17; N, 3.90. Found: C, 49.91; H, 6.22; N, 4.14.

EXAMPLE 32

Preparation of 4-amino-4-phenylcyclohexanone, ethylene ketal hydrochloride

A reaction mixture consisting of 21.9 gm. (0.085 mole) 4-isocyanato-4-phenylcyclohexanone ethylene ketal (prepared as in Example 17, Part G), 10.9 gm. sodium hydroxide, and 210 ml. ethylene glycol is heated at the reflux temperature for sixty-six (66) hours. A solution results which is cooled in an ice-water bath. A small amount of ice is added to the solution followed by 23 ml. of concentrated hydrochloric acid which is added dropwise with stirring. After five minutes, the acidified solution is made strongly basic by adding 50% aqueous sodium hydroxide. The basic solution is diluted with 800 ml. water. The strongly basic, dilute aqueous solution is then extracted four times with 200 ml. portions of diethyl ether. The extracts are combined and washed with water and with brine, before removing the ether by evaporation under reduced pressure. The residue thus obtained is dissolved in 50 ml. of diethyl ether and the oily solution is treated with an equivalent of 3 N hydrogen chloride in diethyl ether. A precipitate forms which is collected on a filter and recrystallized from a mixture of methylene chloride and ethyl acetate. There is thus obtained 15.2 gm. (52% yield) of 4-amino-4-phenylcyclohexanone, ethylene ketal hydrochloride which has a melting point at 226° to 228° C. (with decomposition). A second crop of crystals weighs 1.60 gm. and has a melting range from 222° to 226° C. An analytical sample has a melting point at 248° to 249° C.

Analysis: Calc'd. for $C_{14}H_{20}ClNO_2$: C, 62.33; H, 7.47; N, 5.19. Found: C, 61.93; H, 7.58; N, 5.53.

EXAMPLE 33

Preparation of 4-(N-allyl-N-methylamino)-4-phenylcyclohexanone, ethylene ketal hydrochloride A reaction mixture consisting of the free base from 2.46 gm. (0.0087 mole) of 4-methylamino-4-phenylcyclohexanone ethylene ketal hydrochloride (prepared in Example 17, Part G, above), 1.05 gm. (0.75 ml.) allyl bromide, 1.28 gm. potassium carbonate, 10.0 ml. dimethylformamide, and 40.0 ml. benzene is heated at the reflux temperature, with stirring, for eighteen (18) hours. After cooling, this mixture is washed with water and then with brine before the volatile solvents are removed by evaporation under reduced pressure. The residue thus obtained is dissolved in diethyl ether and 0.6 N hydrogen chloride in diethyl ether is added in order to form the hydrochloride salt. The hydrochloride thus formed, precipitates and is collected on a filter. The filter cake is recrystallized from a mixture of methylene chloride and ethyl acetate and there is thus obtained 1.82 gm. (65% yield) of 4-(N-allyl-N-methylamino)-4-phenylcyclohexanone, ethylene ketal hydrochloride having a melting range from 163° to 167° C.

Analysis: Calc'd. for $C_{18}H_{26}ClNO_2$: C, 64.94; H, 8.17; N, 4.21. Found: C, 65.33; H, 7.93; N, 4.03.

EXAMPLE 34

Preparation of 4-(N-allyl-N-methylamino)-4-phenylcyclohexanone hydroiodide

A reaction solution consisting of 1.82 gm. (0.0058 mole) of 4-(N-allyl-N-methylamino)-4-phenylcyclohexanone, ethylene ketal hydrochloride (prepared in Example 33, above), 8.0 ml. of 2.5 N hydrochloric acid and 16.0 ml. methanol is set aside in a stoppered reaction vessel at 25° C. for sixty-six (66) hours. After removing most of the solvent by evaporation under reduced pressure, the concentrate thus obtained is extracted with methylene chloride. The methylene chloride solution is washed first with saturated aqueous sodium bicarbonate, then with water, and finally with 10% hydroiodic acid. The methylene chloride solvent is then removed by evaporation, and the residue obtained is recrystallized two times from a mixture of methylene chloride and ethyl acetate. There is thus obtained 0.88 gm. (42% yield) of 4-(N-allyl-N-methylamino)-4-phenylcyclohexanone hydroiodide having a melting point at 182° to 183° C.

Analysis: Calc'd. for $C_{16}H_{22}INO$: C, 51.76; H, 5.97; N, 3.77. Found: C, 51.73; H, 5.96; N, 3.84.

EXAMPLE 35

Preparation of 4-[[(ethoxycarbonyl)methyl]-methylamino]-4-phenylcyclohexanone, ethylene ketal, p-toluenesulfonate A reaction mixture consisting of 8.77 gm. (0.031 mole) of 4-methylamino-4-phenylcyclohexanone, ethylene ketal hydrochloride (prepared as in Example 17, Part G, above), 5.16 gm. (3.42 ml.) ethyl bromoacetate, 4.29 gm. potassium carbonate, and 120 ml. dimethylformamide is heated in an oil bath to 100° C. and then held at that temperature with stirring for eighteen (18) hours. After removing the solvent medium by evaporation under reduced pressure, the residue obtained is dissolved in a mixture of 25 ml. water and 150 ml. benzene. The benzene layer is allowed to separate from the water and is recovered. It is washed with water and then with brine. The benzene is then removed by evaporation under reduced pressure. The residue thus obtained is dissolved in diethyl ether and to the ether solution is added 5.9 gm. p-toluenesulfonic acid dissolved in the minimum possible amount of diethyl ether. A gummy precipitate forms which is recrystallized two times from a mixture of methylene chloride and ethyl acetate. There is thus obtained 10.0 gm. (63% yield) of 4-[[(ethoxycarbonyl)methyl]methylamino]-4-phenylcyclohexanone, ethylene ketal, p-toluenesulfonate having a melting range from 108° to 115° C. An analytical sample melts from 115° to 117° C.

Analysis: Calc'd. for $C_{26}H_{35}NO_8S$: C, 59.86; H, 6.76; N, 2.68. Found: C, 60.90; H, 7.16; N, 2.58.

EXAMPLE 36

Preparation of 4-[(2-hydroxyethyl)methylamino]-4-phenylcyclohexanone, ethylene ketal hydrochloride A solution consisting of 4.52 gm. (0.0136 mole) of 4-[[(ethoxycarbonyl)methyl]methylamino]-4-phenylcyclohexanone, ethylene ketal, p-toluenesulfonate (prepared in Example 35, above), and 100 ml. tetrahydrofuran is added to a suspension of 0.52 gm. lithium aluminum hydride in 10 ml. tetrahydrofuran. This reaction is heated at the reaction mixture is heated at the reflux temperature for four (4) hours, after which heating it is allowed to cool and then chilled in an ice bath. To the chilled solution is added 0.52 ml. water followed by 0.52 ml. of 15% aqueous sodium hydroxide, and finally followed by another 1.56 ml. water. A gel forms and the gelatinous liquid is poured through a filter. The filtrate is collected and the liquids removed by evaporation under reduced pressure. The residue thus obtained is chromatographed on a 400 ml. column of silica gel and the chromatogram is developed by elution with a 3% solution of methanol in methylene chloride which has been saturated with ammonia. The fractions containing the prospective product, as determined by thin layer chromatography, are combined and the solvents removed by evaporation under reduced pressure. The residue thus obtained is dissolved in diethyl ether and then hydrogen chloride saturated diethyl ether is added. A precipitate forms which is collected on a filter and recrystallized from a mixture of methylene chloride and ethyl acetate. There is thus obtained 2.56 gm. (58% yield) of 4-[(2-hydroxyethyl)methylamino]-4-phenylcyclohexanone ethylene ketal hydrochloride having a melting range from 184° to 186° C. A second crop of crystals obtained by removing some of the solvent mixture from the mother liquors by evaporation under reduced pressure weighs 0.56 gm. and has a melting range from 176° to 182° C.

Analysis: Calc'd. for $C_{17}H_{26}ClNO_3$: C, 62.28; H, 7.99; N, 4.27. Found: C, 62.14; H, 8.21; N, 4.10.

EXAMPLE 37

Preparation of 4-[(2-hydroxyethyl)methylamino]-4-phenylcyclohexanone

A reaction mixture consisting of 1.50 gm. (0.0046 mole) of 4-[(2-hydroxyethyl)methylamino]-4-phenylcyclohexanone, ethylene ketal, hydrochloride (prepared in Example 36, above), 3 ml. of 2.5 N hydrochloric acid, and 30 ml. acetone is stirred at 25° C. for eighteen (18) hours. After removing most of the acetone by evaporation under reduced pressure, the concentrate thus obtained is basified with sodium bicarbonate. The basic mixture is then extracted three times with 25 ml. portions of methylene chloride. The methylene chloride extracts are combined and the solvent is removed by evaporation under reduced pressure. The residue thus obtained is recrystallized two times from a mixture of acetone and technical hexane to give 0.71 gm. (62% yield) of 4-[(2-hydroxyethyl)methylamino]-4-phenylcyclohexanone having a melting range from 139° to 141° C.

Analysis: Calc'd. for $C_{15}H_{21}NO_2$: C, 72.84; H, 8.56; N, 5.66. Found: C, 72.80; H, 8.68; N, 5.56.

EXAMPLE 38

Preparation of 4-Methylacetamido-4-phenylcyclohexanone, ethylene ketal

A reaction solution consisting of the free base from 1.08 gm. (0.0038 mole) of 4-methylamino-4-phenylcyclohexanone, ethylene ketal hydrochloride (prepared in Example 17, Part G, above), 6.0 ml. pyridine, and 2.0 ml. acetic anhydride is set aside for eighteen (18) hours at 25° C. and then poured into ice:water. The ice:water mixture is then extracted three times with 25 ml. portions of methylene chloride. The combined methylene chloride extracts are first washed with ice-cold 2.5 N hydrochloric acid, followed by a washing with water, and finally a washing with saturated aqueous sodium bicarbonate. The methylene chloride is then removed by evaporation under reduced pressure, and the residue thus obtained is chromatographed on a 100 ml. column of silica gel. The chromatogram is developed with a solvent mixture consisting of 15% ethyl acetate in methylene chloride. The appropriate fractions are combined, and the solvents are removed by evaporation under reduced pressure. The residue thus obtained is recrystallized from a mixture of methylene chloride and technical hexane to give 0.57 gm. (52% yield) of 4-methylacetamido-4-phenylcyclohexanone, ethylene ketal having a melting point at 98° to 99.5° C.

Analysis: Calc'd. for $C_{17}H_{23}NO_3$: C, 70.56; H, 8.01; N, 4.84. Found: C, 70.78; H, 7.93; N, 4.98.

EXAMPLE 39

Preparation of 4-Methylamino-4-phenylcyclohexanone hydrochloride

A reaction mixture consisting of 1.0 gm. (0.0035 mole) of 4-methylamino-4-phenylcyclohexanone, ethylene ketal, hydrochloride (prepared in Example 17, Part G, above) 2.0 ml. of 2.5 N hydrochloric acid, and 20 ml. acetone is stirred continuously for eighteen (18) hours, at 25° C. The reaction mixture is then made basic by adding solid sodium bicarbonate, and most of the solvent is removed by evaporation under reduced pressure. The concentrated material thus obtained is ectracted four times with 20 ml. portions of methylene chloride. The extracts are combined and the methylene chloride is removed by evaporation under reduced pressure. A gummy residue is obtained that is dissolved in diethyl ether. The ether solution is treated with hydrogen chloride in ether. A precipitate forms which is collected on a filter and recrystallized from a mixture of methylene chloride and ethyl acetate. There is thus obtained 0.53 gm. (74% yield) of 4-methylamino-4-phenylcyclohexanone hydrochloride having a melting range from 218° to 220° C.

Analysis: Calc'd. for $C_{13}H_{18}ClNO$: C, 65.12; H, 7.56; N, 5.84. Found: C, 64.35; H, 7.64; N, 5.85.

EXAMPLE 40

Preparation of 4-(m-hydroxyphenyl)-4-(methyl-n-butylamino)cyclohexanone

Part A:
4-Cyano-4-(m-hydroxyphenyl)cyclohexan-1-one

To an ice-cooled solution of 10.0 g. (0.044 mole) of 4-cyano-4-(m-anisyl)cyclohexan-1-one (prepared in Example 11, Part C), in 125 ml. methylene chloride there is added dropwise 13 ml. of boron tribromide. Following 4 hours stirring in the cold the mixture is poured onto ice and diluted with 50 ml. chloroform. The organic layer is washed with water, aqueous sodium bicarbonate and brine, and taken to dryness. The residual solid is recrystallized from acetone:Skellysolve B to give 7.60 g. of 4-cyano-4-(m-hydroxyphenyl)cyclohexan-1-one, m.p. 130°-133° C.

Analysis: Calc'd. for $C_{13}H_{13}NO_2$: C, 72.54; H, 6.09; N, 6.51. Found: C, 72.50; H, 6.14; N, 6.35.

Part B:
4-Cyano-4-(m-hydroxyphenyl)cyclohexan-1-one, ethylene ketal

A mixture of 8.80 g. (0.041 mole) of 4-cyano-4-(m-hydroxyphenyl)cyclohexan-1-one, 2.50 ml. ethylene glycol and 0.26 g. p-toluenesulfonic acid in 170 ml. benzene is heated at reflux under a Deane-Stark trap for 4 hours. The mixture is then allowed to cool, washed with aqueous sodium bicarbonate and taken to dryness. The residual solid is recrystallized from methylene chloride:Skellysolve B to give 9.85 g. of 4-cyano-4-(m-hydroxyphenyl)cyclohexan-1-one, ethylene ketal, m.p. 109°-110.5° C.

Analysis: Calc'd. for $C_{15}H_{17}NO_3$: C, 69.48; H, 6.61; N, 5.32. Found: C, 69.23; H, 6.69; N, 5.32.

Part C:
4-Cyano-4-(m-benzyloxyphenyl)cyclohexan-1-one, ethylene ketal

To a solution of 9.85 g. of 4-cyano-4-(m-hydroxyphenyl)cyclohexan-1-one, ethylene ketal (prepared in Part B, above) in 40 ml. DMF and 80 ml. benzene there is added 1.85 g. of a 50% dispersion of sodium hydride in mineral oil. The mixture is stirred for 15 mins. at room temperature and 1 hour at reflux. Benzyl chloride (6.53 g.) is then added, the mixture heated for an additional 4 hours and allowed to cool. The reaction mixture is washed in turn with water and brine and taken to dryness. The residual solid is recrystallized from ether:-petroleum ether to give 11.70 g. of 4-cyano-4-(m-benzyloxyphenyl)cyclohexan-1-one, ethylene ketal, m.p. 67°-69° C.

Analysis: Calc'd. for $C_{22}H_{23}NO_3$: C, 75.62; H, 6.63; N, 4.01. Found: C, 75.34; H, 6.66; N, 4.01.

Part D:
4-(m-benzyloxyphenyl)cyclohexan-1-one-4-carboxylic acid, ethylene ketal

A mixture of 7.00 g. (0.020 mole) of 4-cyano-4-(m-benzyloxyphenyl)cyclohexan-1-one, ethylene ketal (prepared in Part C, above) and 1.20 g. sodium hydroxide in 50 ml. ethylene glycol is heated at reflux for 17 hours. The solution is allowed to cool, diluted to 300 ml. with water and covered with 100 ml. ether. The aqueous layer is acidified with 5 ml. concentrated hydrochloric acid and the organic layer separated. The aqueous layer is then extracted with 100 ml. portions of ether and methylene chloride. The organic layer and extracts are combined, washed with water and brine and taken to dryness. There is obtained 7.22 g. of 4-(m-benzyloxyphenyl)cyclohexan-1-one-4-carboxylic acid, ethylene ketal, m.p. 108°-110.5° C. A small sample is recrystallized from ether to give the analytical sample, m.p. 118.5°-120.5° C.

Analysis: Calc'd for $C_{22}H_{24}O_5$: C, 71.72; H, 6.57. Found: C, 71.80; H, 6.89.

Part E:
4-(m-benzyloxyphenyl)-4-(methylamino)cyclohexan-1-one, ethylene ketal

A mixture of 7.22 g. (0.020 mole) of 4-(m-benzyloxyphenyl)cyclohexan-1-one-4-carboxylic acid, ethylene ketal, (prepared in Part D, above) 5.52 g. of diphenylphosphorylazide and 2.8 ml. triethylamine in 50 ml. anisole is heated in an oil bath at 90° for 2 hours. The bulk of the solvent is then removed in vacuum and the residue chromatographed over 600 ml. silica gel. The column is eluted with 2% ethyl acetate in methylene chloride and those fractions which contain product as determined by tlc are combined. There is obtained 4.97 g. of the intermediate isocyanate as an oil.

A solution of this oil (isocyanate) in 80 ml. THF is added to a suspension of 0.78 g. lithium aluminum hydride in 10 ml. THF. Following 6 hours heating at reflux the mixture is cooled in an ice bath and treated in turn with 0.7 ml. water, 0.7 ml. 15% sodium hydroxide and 2.4 ml. water. The inorganic gel is separated on a filter and the filtrate taken to dryness. The residual solid is recrystallized from petroleum ether to afford 3.31 g. of 4-(m-benzyloxyphenyl)-4-(methylamino)cyclohexan-1-one, ethylene ketal, m.p. 64°-66° C.

Analysis: Calc'd for $C_{22}H_{27}NO_3$: C, 74.75; H, 7.70; N, 3.96. Found: C, 75.03; H, 7.53; N, 3.93.

Part F:
4-(Methyl-n-butylamino)-4-(m-benzyloxyphenyl)cyclohexan-1-one, ethylene ketal To an ice cold solution of 3.31 g. (9.4 mmole) of 4-methylamino-4-(m-benzyloxyphenyl)cyclohexan-1-one, ethylene ketal (prepared in Part E, above) and 1.30 ml. triethylamine in 40 ml. THF there is added dropwise 1.0 g. (1.10 ml.) butyryl chloride. Following 6 hours' standing in the cold the bulk of the solvent is removed in vacuum. The residual is diluted with ice-water and ether. The organic layer is separated and washed in turn with water, saturated sodium bicarbonate and brine. The solution is taken to dryness to give the amide as a gum. Infrared spectrum is consistent with the structure assigned (absorption at 1660 cm$^{-1}$). A solution of the crude amide thus obtained in 80 ml. THF is added to a suspension of 0.50 g. lithium aluminum hydride in 10 ml. THF. Following 6 hours' heating at reflux the mixture is cooled in ice and treated in turn with 0.50 ml. water, 0.50 ml. 15% sodium hydroxide and 1.5 ml. water. The inorganic gel is collected on a filter and the filtrate taken to dryness. There is obtained 3.50 g. of 4-(methyl-n-butylamino)-4-(m-benzyloxyphenyl)cyclohexan-1-one, ethylene ketal as an amorphous gum which shows a single spot on thin layer chromatography (tlc).

Part G:
4-(Methyl-n-butylamino)-4-(m-hydroxyphenyl)cyclohexan-1-one, ethylene ketal hydrochloride A mixture of 3.56 g. of the crude tertiary amine (prepared in Part F, above), 3.6 ml. 3 N ethereal hydrogen chloride and 1.78 g. 10% palladium on charcoal in 150 ml. ethyl acetate is shaken in an atmosphere of hydrogen for 18 hours. The catalyst and some precipitated product are then collected on a filter. The collected solid is washed thoroughly with chloroform. The combined filtrate and washes are then taken to dryness. The residual solid is recrystallized from methylene chloride-:acetone to give 2.00 g. of 4-(methyl-n-butylamino)-4-(m-hydroxyphenyl)cyclohexan-1-one, ethylene ketal hydrochloride, m.p. 208°-210° C.; m.m.p. (mixed melting point) with authentic material (prepared in Example 42) 208°-210° C.

Part H: Preparation of 4-(m-hydroxyphenyl)-4-(methyl-n-butylamino)cyclohexanone

Following the procedure of Example 2, but substituting 4-(m-hydroxyphenyl)-4-(methyl-n-butylamino)cyclohexan-1-one, ethylene ketal hydrochloride (prepared in Part G, above) for the 4-(p-chlorophenyl)-4-dimethylaminocyclohexanone, ethylene ketal hydrochloride there is obtained the object compound 4-(m-hydroxyphenyl)-4-(methyl-n-butylamino)cyclohexanone. Recrystallization from ether: petroleum ether gives an analytical sample, m.p. 89°-91° C.

Analysis: Calc'd for $C_{17}H_{25}NO_2$: C, 74.14; H, 9.15; N, 5.08. Found: C, 74.32; H, 9.04; N, 5.26.

Example 41

Alternative preparation for a preferred compound 4-(p-Chlorophenyl)-4-dimethylaminocyclohexanone, ethylene ketal free base and the hydrochloride thereof Part A: Preparation of precursor Cyclohexane-1,4-dione, ethylene monoketal A reaction mixture consisting of 10 gm. (0.085 mole) 4-hydroxycyclohexanone, 4.75 ml. ethylene glycol, 0.20 gm. p-toluenesulfonic acid, and 100 ml. benzene is heated at the reflux temperature in a reaction vessel fitted with a Dean and Stark trap for 2 hours. After the reaction mixture has cooled, it is washed first with water and then with brine. The benzene is then removed by evaporation under reduced pressure giving the intermediate 4-hydroxycyclohexanone ethylene monoketal as a viscous oil weighing 14.12 gm. The 4-hydroxycyclohexanone ethylene monoketal is dissolved in 100 ml. methylene chloride and added with stirring to a suspension consisting of 55.0 gm. chromium trioxide (predried for 24 hours under reduced pressure over phosphorous pentoxide), one liter dry methylene chloride, and 52.8 gm. 3,5-dimethylpyrazole. After continued stirring for ten (10) min. this dark reaction mixture is poured onto a two liter column of silica gel. When the reaction mixture has been completely adsorbed, the chromatogram is developed with a 1:1 mixture of ethyl acetate and technical hexane (Skellysolve B—a mixture of isomeric hexanes having a boiling range between 60° and 70° C.). The appropriate fractions as determined by TLC are collected and combined, after which the solvents are removed by evaporation under reduced pressure. The crystals thus obtained are recrystallized from technical hexane, and there is thus obtained 10.82 gm. (91% yield) of the desired cyclohexane - 1,4-dione, ethylene monoketal having a melting point at 68° to 69° C. [The literature value is 71.5° to 72.5° C.]

Part B: Preparation of first intermediate
4-Cyano-4-dimethylaminocyclohexanone, ethylene ketal A reaction mixture consisting of 3.0 gm. (0.019 mole) of the cyclohexane-1,4-dione, ethylene monoketal prepared in Part A, above, 3.0 gm. potassium cyanide, 4.5 gm. dimethylamine hydrochloride, 3.0 ml. methanol, and 25 ml. saturated aqueous dimethylamine is stirred at 25° C. for 48 hours. The reaction mixture is then extracted successively with five 40 ml.-portions of diethyl ether. The ether extracts are combined and the ether is removed by evaporation under reduced pressure. The residue thus obtained is dissolved in methylene chloride. Some small amount of water present is separated, and the organic solvent portion is conserved for removal of the methylene chloride by evaporation under reduced pressure. The residual solid thus obtained is recrystallized from technical hexane to give 3.6 gm. (78% yield) of the desired intermediate 4-cyano-4-dimethylaminocyclohexanone ethylene ketal having a melting point at 79° to 81° C.

Analysis: Calc'd. for $C_{11}H_{17}N_2O_2$: C, 62.83; H, 8.63; N, 13.33. Found: C, 62.92; H, 8.66; N, 13.58.

Part C: Preparation of object compound,
4-(p-Chlorophenyl)-4-dimethylaminocyclohexanone, ethylene ketal hydrochloride To a Grignard reagent prepared from 2.73 gm. of p-chlorobromobenzene, 0.35 gm. magnesium and 30 ml. tetrahydrofuran (THF), is added 1.50 g. (0.071 mole) of 4-cyano-4-dimethylaminocyclohexanone ethylene ketal (prepared in Part B) in 40 ml. of THF. The reaction mixture is heated for three (3) days at the reflux temperature. It is then cooled, chilled in an ice bath and 20 ml. saturated ammonium chloride in benzene added. The organic phase is separated. It is washed initially with water and then with brine. Finally, the solvents are removed by evaporation under reduced pressure. The residue thus obtained is dissolved in diethyl ether and 4 N ethereal hydrogen chloride is added until precipitation is complete. The salt thus obtained is collected on a filter as a gummy material. It is suspended in methylene chloride and one N aqueous sodium hydroxide is added. The organic layer is separated and the methylene chloride is removed by evaporation under reduced pressure. The residue thus obtained is added onto a 200 ml. column of silica gel, the chromatogram is developed with methylene chloride containing 4% methanol and 20-ml. fractions are collected. The solvent is removed by evaporation under reduced pressure and the residue is dissolved in diethyl ether. The ether solution is treated with 4 N ethereal hydrogen chloride until precipitation of the desired 4-(p-chlorophenyl)-4-dimethylaminocyclohexanone ethylene ketal hydrochloride is complete. The precipitate is collected on a filter and crystallized from a mixture of methylene chloride and ethyl acetate to give 0.80 gm. (34% yield) of pure 4-(p-chlorophenyl)-4-dimethylaminocyclohexanone ethylene ketal hydrochloride having a melting point at 252° to 254° C.

EXAMPLE 42

Alternative preparation for a preferred compound
4-(m-hydroxyphenyl)-4-(methyl-n-butylamino)cyclohexanone, ethylene ketal hydrochloride Part A:
4-(methyl-n-butylamino)-4-cyanocyclohexan-1-one, ethylene ketal A mixture of 2.05 g. (15 mmole) of 1,4-cyclohexanedione ethylene monoketal (prepared as in Example 41, Part A), 2.05 g. potassium cyanide, 5.40 g. methyl-n-butylamine, in 8 ml. water and 12 ml. 2.5 N hydrochloric acid is stirred at room temperature for 5 days. The mixture is then extracted thoroughly with 5 portions, of 40 ml. each, methylene chloride. The extracts are combined and taken to dryness. To a solution of the residual gum in 50 ml. ether there is added sufficient 3 N ethereal hydrogen chloride to precipitate all the basic material. That precipitate is recrystallized from methylene chloride: ethyl acetate to give 2.65 g. of 4-(methyl-n-butylamino)-4-cyanocyclohexan-1-one, ethylene ketal (hydrochloride salt), m.p. 114°–120° C.

Analysis: Calc'd. for $C_{14}H_{25}ClN_2O_2.1\frac{1}{2}H_2O$: C, 53.23; H, 4.93; N, 8.87. Found: C, 53.62; H, 8.67; N, 8.71.

A suspension of the salt in 50 ml. of methylene chloride is shaken with 40 ml. 1 N sodium hydroxide. The organic layer is separated and taken to dryness to give 2.49 g. of the 4-(methyl-n-butylamino)-4-cyanocyclohexan-1-one, ethylene ketal as an oil.

Part B:
4-(methyl-n-butylamino)-4-(m-hydroxyphenyl)-cyclohexan-1-one, ethylene ketal hydrochloride To the Grignard reagent prepared from the tetrahydropyranyl ether of 4.80 g. of m-bromophenol, 0.81 g. magnesium and 60 ml. THF there is added a solution of 2.49 g. 4-(methyl-n-butylamino)-4-cyanocyclohexan-1-one, ethylene ketal (prepared in Part A, above) in 25 ml. THF. Following 24 hours' heating at reflux the mixture is cooled in an ice bath and treated with 25 ml. each saturated aqueous ammonium chloride and benzene. The organic layer is washed with water and brine and taken to dryness. The residue is dissolved in 25 ml. ether and treated with just sufficient 3 N ethereal hydrogen chloride to precipitate the basic material. This gum is dissolved in 40 ml. water. Following 5 mins. standing at room temperature the solution is neutralized with solid sodium bicarbonate. The mixture is then extracted with 3 portions (40 ml. each) of methylene chloride. The extracts are then taken to dryness. The residual gum is chromatographed on a 1"×48" column of tlc grade silica gel (elution with 7.5% methanol in chloroform). Those fractions which contain product (as determined by tlc analysis) are combined and taken to dryness. The residual gum is converted to the hydrochloride salt and this is recrystallized from methylene chloride:acetone. There is obtained 152 mg. of 4-(methyl-n-butylamino)-4-(m-hydroxyphenyl)cyclohexan-1-one, ethylene ketal hydrochloride, m.p. 206°-208° C.

Analysis: Calc'd. for $C_{19}H_{30}ClNO_3$: C, 64.11; H, 8.51; N, 3.94. Found: C, 64.46; H, 8.44; N, 3.75.

EXAMPLE 43

Preparation of 4-(m-hydroxyphenyl)-4-dimethylaminocyclohexanone, ethylene ketal A reaction solution consisting of 5.0 gm. (0.029 mole) m-bromophenol, 5.0 gm. dihydropyran, 0.30 gm. p-toluenesulfonic acid, and 80 ml. anhydrous diethyl ether is stirred at 25° C. for four (4) hours. The mixture is washed successively with 25 ml. portions of 1 N aqueous sodium hydroxide, with water, and with brine. The thus washed organic layer is taken to dryness by removing the solvent by evaporation under reduced pressure. There is thus obtained 7.42 gm. of m-(tetrahydropyranyl-2-oxy)bromobenzene which is converted to the corresponding Grignard reagent by dissolving in 60 ml. of tetrahydrofuran and adding the solution to 0.70 gm. magnesium. To this Grignard is added 1.50 gm. (0.0071 mole) of 4-cyano-4-dimethylaminocyclohexanone ethylene ketal (prepared in Example 41, Part B, above) dissolved in 30 ml. tetrahydrofuran. This reaction mixture is heated at the reflux temperature for 22 hours. After cooling, the mixture is treated with 10 ml. saturated ammonium chloride in benzene. The organic solvent portion is initially washed with water and then with brine. The organic solvent is then removed by evaporation under reduced pressure. The residue thus obtained is dissolved in diethyl ether and treated with 4 N ethereal hydrogen chloride until precipitation of the hydrochloride salt is complete. The salt is collected on a filter and then suspended in 25 ml. water containing 1 ml. 2.5 N hydrochloric acid. The acidified mixture is stirred at 25° C. for one hour, when sodium bicarbonate (solid) is added until the pH is 8. This slightly basic mixture is extracted thoroughly with diethyl ether. The ether extracts are combined and the ether removed be evaporation under reduced pressure. The residue thus obtained is transferred to a column of the grade silica gel 1" in cross section by 48" in length. The chromatogram is developed with a solvent medium consisting of 0.5% ammonia and 7.5% methanol in chloroform, and 20-ml. fractions are collected. Those fractions which contain product (as determined by tlc analysis) are combined. The solvent is removed by evaporation under reduced pressure to give 0.96 gm. (48% yield) of crude 4-(m-hydroxyphenyl)-4-dimethylaminocyclohexanone, ethylene ketal having a melting point at 169° to 175° C. An analytical sample is obtained by recrystallization from a mixture of ethyl acetate and cyclohexane. The melting point is 175° to 177° C.

Analysis: Calc'd. for $C_{16}H_{23}NO_3$: C, 69.28; H, 8.36; N, 5.05. Found: C, 69.08; H, 8.13; N, 5.02.

EXAMPLE 44

Preparation of 4-(m-hydroxyphenyl)-4-dimethylaminocyclohexanone

A reaction mixture consisting of 1.92 gm. (0.0069 mole) of 4-(m-hydroxyphenyl)-4-dimethylaminocyclohexanone, ethylene ketal (prepared in Example 43, above), 15 ml. 2.5 N hydrochloric acid, and 30 ml. methanol is stirred continuously for three (3) days (72 hours). The bulk of the solvent is then removed by evaporation under reduced pressure, and solid sodium bicarbonate is added until the pH is brought to 8. This basic mixture is then extracted with six 20 ml. portions of chloroform. The extracts are combined and the chloroform removed by evaporation under reduced pressure. The residue thus obtained is recrystallized from a mixture of acetone and technical hexane to give 0.48 gm. (30% yield) of 4-(m-hydroxyphenyl)-4-dimethylaminocyclohexanone having a melting point at 127° to 130° C.

Analysis: Calc'd. for $C_{14}H_{19}NO_2$: C, 72.07; H, 8.21; N, 6.01. Found: C, 72.02; H, 8.13; N, 5.87.

EXAMPLE 45

Part A

Following the procedure of Example 40, Part F, but separately substituting acetyl chloride, 2,2-dimethylpropionyl chloride, cyclohexanecarbonyl chloride, cyclopentanecarbonyl chloride and 2-cyclopentylacetyl chloride for n-butyryl chloride there are prepared the corresponding:

4-(m-benzyloxyphenyl)-4-(ethylmethylamino)cyclohexanone ethylene ketal, 4-(m-benzyloxyphenyl)-4-(pivalylmethylamino)cyclohexanone ethylene ketal, 4-(m-benzyloxyphenyl)-4-(N-cyclohexylmethyl-N-methylamino)cyclohexanone ethylene ketal, and 4-(m-benzyloxyphenyl)-4-(N-cyclopentylmethyl-N-methylamino)cyclohexanone ethylene ketal, respectively.

Part B

Following the procedure of Example 40, Part G, but substituting the compounds obtained in Part A (above) for 4-(methyl-n-butylamino)-4-(m-benzyloxyphenyl)cyclohexanone ethylene ketal there are obtained 4-(m-hydroxyphenyl)-4-(ethylmethylamino)cyclohexanone ethylene ketal hydrochloride, 4-(m-hydroxyphenyl)-4-(pivalylmethylamino)cyclohexanone ethylene ketal hydrochloride, 4-(m-hydroxyphenyl)-4-(N-cyclohexylmethyl-N-methylamino)cyclohexanone ethylene ketal hydrochloride, and 4-(m-hydroxyphenyl)-4-(N-cyclopentylmethyl-N-methylamino)cyclohexanone ethylene ketal hydrochloride, respectively.

Part C

Following the procedure of Example 44 but substituting the compounds prepared in Part B (above) for the 4-(m-hydroxyphenyl)-4-(dimethylamino)cyclohexanone ethylene ketal there are prepared the object compounds 4-(m-hydroxyphenyl)-4-(ethylmethylamino)cyclohexanone, 4-(m-hydroxyphenyl)-4-(pivalylmethylamino)cyclohexanone, 4-(m-hydroxyphenyl)-4-(N-cyclohexylmethyl-N-methylamino)cyclohexanone, and 4-(m-hydroxyphenyl(-4-(N-cyclopentylmethyl-N-methylamino)cyclohexanone, respectively.

EXAMPLE 46

Preparation of
4-(p-hydroxyphenyl)-4-(methyl-n-butylamino)cyclohexanone

Part A

Following the procedure of Example 40, Parts A-E, but initially substituting 4-p-anisyl-4-cyanocyclohexanone (prepared in Example 7, Part C) for the 4-m-anisyl-4-cyanocyclohexanone and subsequently substituting the appropriate intermediates in appropriate quantities there is obtained 4-methylamino-4-(p-benzyloxyphenyl)cyclohexanone ethylene ketal.

Part B

Following the procedure of Example 40, Part F, but substituting the appropriate quantity of 4-(p-benzyloxyphenyl)-4-methylaminocyclohexanone ethylene ketal for 4-(m-benzyloxyphenyl)-4-methylaminocyclohexanone ethylene ketal there is obtained 4-(n-butylmethylamino)-4-(p-benzyloxyphenyl)cyclohexanone ethylene ketal.

Part C

Following the procedure of Example 40, Part G, but substituting 4-(p-benzyloxyphenyl)-4-(n-butylmethylamino)cyclohexanone ethylene ketal (prepared in Part B, above) for 4-(m-benzyloxyphenyl)-4-(n-butylmethylamino)cyclohexanone ethylene ketal there is obtained 4-(p-hydroxyphenyl)-4-(n-butylmethylamino)cyclohexanone ethylene ketal hydrochloride.

Part D

Following the procedure of Example 44, but substituting 4-(p-hydroxyphenyl)-4-(n-butylmethylamino)cyclohexanone ethylene ketal hydrochloride (prepared in Part C, above) for the 4-(m-hydroxyphenyl)-4-dimethylaminocyclohexanone, ethylene ketal there is obtained 4-(p-hydroxyphenyl)-4-(n-butylmethylamino)cyclohexanone.

EXAMPLE 47

Part A

Following the procedure of Example 42, Part A, but substituting an appropriate quantity of diethylamine for n-butylmethylamine there is obtained 4-cyano-4-diethylaminocyclohexanone ethylene ketal.

Part B

Following the procedure of Example 42, Part B, but substituting the appropriate quantities of the compound prepared above in Part A for 4-(methyl-n-butylamino)-4-cyanocyclohexanone, ethylene ketal, and of the tetrahydropyranyl ether of p-bromophenol for the corresponding ether of m-bromophenol, there is obtained 4-(p-hydroxyphenyl)-4-diethylaminocyclohexanone ethylene ketal hydrochloride.

Part C

Following the procedure of Example 44, but substituting an appropriate quantity of the compound prepared above (Part B) for 4-(m-hydroxyphenyl)-4-dimethylaminocyclohexanone ethylene ketal there is obtained 4-(p-hydroxyphenyl)-4-diethylaminocyclohexanone.

EXAMPLE 48

Following the procedure of Example 1, Part A; Example 3, Part A; and Example 17, Part A, but separately substituting (2-bromo-5-methoxyphenyl)acetonitrile,
(3-bromo-4-phenethyl)acetonitrile,
(5-bromo-4-anisyl)acetonitrile,
[5-bromo-3-(n-propoxy)phenyl]acetonitrile,
(3-chloro-4-fluorophenyl)acetonitrile,
(3-chloro-6-methoxyphenyl)acetonitrile,
(2,6-dichlorophenyl)acetonitrile,
(3,5-diisopropylphenyl)acetonitrile,
(4,5-dimethoxyphenyl)acetonitrile,
(o-ethylphenyl)acetonitrile, for (p-chlorophenyl)acetonitrile, there are prepared the corresponding:
dimethyldiester of 4-(2-bromo-5-methoxyphenyl)-4-cyanopimelic acid,
4-(3-bromo-4-phenethyl)-4-cyanopimelic acid,
4-(5-bromo-4-anisyl)-4-cyanopimelic acid,
4-(5-bromo-3-n-propoxyphenyl)-4-cyanopimelic acid,
4-(3-chloro-4-fluorophenyl)-4-cyanopimelic acid,
4-(3-chloro-6-methoxyphenyl)-4-cyanopimelic acid,
4-(2,6-dichlorophenyl)-4-cyanopimelic acid,
4-(3,5-diisopropylphenyl)-4-cyanopimelic acid,
4-(4,5-dimethoxyphenyl)-4-cyanopimelic acid,
4-(o-ethylphenyl)-4-cyanopimelic acid, respectively.

EXAMPLE 49

Following the procedure of Examples 1, 4, and 17, Parts B, C, D, E, F, G, and H, but substituting as indicated a priori the intermediates prepared in Example 48, above, and those intermediates thus sequentially prepared, there are prepared finally the corresponding:

4-(2-bromo-5-methoxyphenyl)-4-dimethylaminocyclohexanone, ethylene ketal free base and the HCl salt thereof,
4-(3-bromo-4-phenethyl)-4-dimethylaminocyclohexanone, ethylene ketal free base and the HCl salt thereof,
4-(5-bromo-4-anisyl)-4-dimethylaminocyclohexanone, ethylene ketal free base and the HCl salt thereof,
4-(5-bromo-3-n-propoxyphenyl)-4-dimethylaminocyclohexanone, ethylene ketal free base and the HCl salt thereof,
4-(3-chloro-4-fluorophenyl)-4-dimethylaminocyclohexanone ethylene ketal free base and the HCl salt thereof,
4-(3-chloro-6-methoxyphenyl)-4-dimethylaminocyclohexanone ethylene ketal free base and the HCl salt thereof,
4-(2,6-dichlorophenyl)-4-dimethylaminocyclohexanone, ethylene ketal free base and the HCl salt thereof,
4-(3,5-diisopropylphenyl)-4-dimethylaminocyclohexanone, ethylene ketal free base and the HCl salt thereof,
4-(4,5-dimethoxyphenyl)-4-dimethylaminocyclohexanone, ethylene ketal free base and the HCl salt thereof,
4-(o-ethylphenyl)-4-dimethylaminocyclohexanone, ethylene ketal free base and the HCl salt thereof,

EXAMPLE 50

Part A

Following the procedure of Example 41, Part A, but separately substituting trimethylene glycol (1,3-propanediol), 2,2-dimethyl-1,3-propanediol [prepared as described in J. Amer. Chem. Soc. 70, 946 (1948)], 2-phenyl-1,3-propanediol, 2-allyl-1,3-propanediol, for the ethylene glycol, there are prepared the corresponding precursors:

cyclohexane-1,4-dione, trimethylene monoketal,
cyclohexane-1,4-dione, (2,2-dimethyltrimethylene)-monoketal,
cyclohexane-1,4-dione, (2-phenyltrimethylene)monoketal,
cyclohexane,-1,4-dione, (2-allyltrimethylene)monoketal, respectively.

Part B

Following the procedure of Example 41, Part B, but substituting cyclohexane-1,4-dione, trimethylene monoketal, cyclohexane-1,4-dione, (2,2-dimethyltrimethylene)monoketal, cyclohexane-1,4-dione, (2-phenyltrimethylene)monoketal, and cyclohexane-1,4-dione, (2-allyltrimethylene)monoketal for the cyclohexane-1,4-dione, ethylene monoketal, there are prepared the corresponding intermediates:

4-cyano-4-dimethylaminocyclohexanone, trimethylene ketal,
4-cyano-4-dimethylaminocyclohexanone, (2,2-dimethyltrimethylene) ketal,
4-cyano-4-dimethylaminocyclohexanone, (2-phenyltrimethylene) ketal, and
4-cyano-4-dimethylaminocyclohexanone, (2-allyltrimethylene) ketal respectively.

Part C

Following the procedure of Example 41, Part C, but separately substituting each intermediate prepared in Part B, above for the 4-cyano-4-dimethylaminocyclohexanone, ethylene ketal, there are prepared the corresponding object compounds:

4-(p-chlorophenyl)-4-dimethylaminocyclohexanone, trimethylene ketal hydrochloride,
4-(p-chlorophenyl)-4-dimethylaminocyclohexanone, (2,2-dimethyltrimethylene) ketal hydrochloride,
4-(p-chlorophenyl)-4-dimethylaminocyclohexanone, (2-phenyltrimethylene) ketal hydrochloride, and 4-(chlorophenyl)-4-dimethylaminocyclohexanone, (2-allyltrimethylene) ketal hydrochloride, respectively.

EXAMPLE 51

Part A

Following the procedure of Example 42, Part A, but separately substituting each intermediate prepared in Example 50, Part A, for the cyclohexane-1,4-dione ethylene monoketal there are prepared the corresponding intermediates:

4-cyano-4-n-butylmethylaminocyclohexanone, trimethylene ketal,
4-cyano-4-n-butylmethylaminocyclohexanone, (2,2-dimethyltrimethylene) ketal,
4-cyano-4-n-butylmethylaminocyclohexanone, (2-phenyltrimethylene) ketal, and
4-cyano-4-n-butylmethylaminocyclohexanone, (2-allyltrimethylene) ketal, respectively.

Part B

Following the procedure of Example 42, Part B, but separately substituting each intermediate prepared in Part A (above) for 4-cyano-4-(methyl-n-butylamino)cyclohexanone, ethylene ketal, there are prepared the corresponding object compounds:

4-(m-hydroxyphenyl)-4-n-butylmethylaminocyclohexanone, trimethylene ketal hydrochloride,
4-(m-hydroxyphenyl)-4-n-butylmethylaminocyclohexanone, (2,2-dimethyltrimethylene) ketal hydrochloride,
4-(m-hydroxyphenyl)-4-n-butylmethylaminocyclohexanone, (2-phenyltrimethylene) ketal hydrochloride, and
4-(m-hydroxyphenyl)-4-n-butylmethylaminocyclohexanone, (2-allyltrimethylene) ketal hydrochloride, respectively.

EXAMPLE 52

Following the procedure of Example 42, Part A, but separately substituting diethylamine, di-n-propylamine, N-allyl-N-ethylamine, di-n-butylamine, n-butylethylamine, and N-methyl-N-cyclopropylamine, for n-butylmethylamine, there are prepared the corresponding intermediates:

4-cyano-4-diethylaminocyclohexanone, ethylene ketal,
4-cyano-4-di-n-propylaminocyclohexanone, ethylene ketal,
4-cyano-4-(N-allyl-N-ethylamino)cyclohexanone, ethylene ketal,
4-cyano-4-di-n-butylaminocyclohexanone, ethylene ketal,
4-cyano-4-(n-butylethylamino)cyclohexanone, ethylene ketal, and
4-cyano-4-(N-methyl-N-cyclopropylamino)cyclohexanone, ethylene ketal, respectively.

EXAMPLE 53

Following the procedure of Example 42, Part B, but separately substituting each intermediate prepared as in Example 52, for the 4-cyano-4-n-butylmethylaminocyclohexanone, ethylene ketal, there are prepared the corresponding object compounds:

4-(m-hydroxyphenyl)-4-diethylaminocyclohexanone, ethylene ketal hydrochloride,
4-(m-hydroxyphenyl)-4-di-n-propylaminocyclohexanone, ethylene ketal hydrochloride,
4-(m-hydroxyphenyl)-4-(N-allyl-N-ethylamino)cyclohexanone, ethylene ketal hydrochloride,
4-(m-hydroxyphenyl)-4-di-n-butylaminocyclohexanone, ethylene ketal hydrochloride,
4-(m-hydroxyphenyl)-4-(n-butylethylamino)cyclohexanone, ethylene ketal hydrochloride, and
4-(m-hydroxyphenyl)-4-(N-methyl-N-cyclopropylamino)cyclohexanone, ethylene ketal hydrochloride, respectively.

EXAMPLE 54

Following the procedure of Example 44, but separately substituting each compound prepared in Example 53 for the 4-(m-hydroxyphenyl)-4-dimethylaminocyclohexanone, ethylene ketal, there are prepared the corresponding:

4-(m-hydroxyphenyl)-4-diethylaminocyclohexanone,
4-(m-hydroxyphenyl)-4-di-n-propylaminocyclohexanone,
4-(m-hydroxyphenyl)-4-(N-allyl-N-ethylamino)cyclohexanone,
4-(m-hydroxyphenyl)-4-di-n-butylaminocyclohexanone,
4-(m-hydroxyphenyl)-4-(n-butylethylamino)cyclohexanone, and 4-(m-hydroxyphenyl)-4-(N-methyl-N-cyclopropylamino)cyclohexanone, respectively.

EXAMPLE 55

Preparation of 4-(m-trifluoromethylphenyl)-4-dimethylaminocyclohexanone ethylene ketal hydrochloride A Grignard reagent is prepared using 4.79 gm. (0.024 mole) m-trifluoromethylbromobenzene, 0.59 gm. magnesium and 50 ml. tetrahydrofuran; to this is added 1.50 gm. (0.0071 mole) 4-cyano-4-dimethylaminocyclohexanone ethylene ketal (prepared in Example 41, Part B, dissolved in 40 ml. tetrahydrofuran. This reaction mixture is heated at the reflux temperature for 17 hours. It is then cooled, chilled in ice, and 20 ml. saturated aqueous ammonium chloride and benzene are added. The organic solution is then separated, initially washed with water, and then washed with brine. The solvents are then removed by evaporation under reduced pressure. The residue thus obtained is dissolved in diethyl ether, and 4 N ethereal hydrogen chloride is added until precipitation of the hydrochloride salt as a gum is complete. The supernatant liquid is decanted and the remaining gum is dissolved in methylene chloride. One N aqueous sodium hydroxide is added. The organic layer is then separated and the methylene chloride is removed by evaporation under reduced pressure. The residue thus obtained is transferred onto a 200 ml. column of silica gel and the chromatogram is developed with methylene chloride containing 3% metahnol. The appropriate fractions, as determined by TLC, are collected and combined. The solvent is removed by evaporation under reduced pressure, and the gummy residue thus obtained is dissolved in diethyl ether. The ether solution is treated with 4 N ethereal hydrogen chloride until precipitation of the hydrochloride salt is complete. The precipitate is collected on a filter and then recrystallized from a mixture of methylene chloride and ethyl acetate to give 0.63 gm. (24% yield) of 4-(m-trifluoromethylphenyl)-4-dimethylaminocyclohexanone ethylene ketal hydrochloride having a melting point at 231° to 232° C.

Analysis: Calc'd. for $C_{17}H_{23}ClF_3NO_2$: C, 55.81; H, 6.33; N, 3.83. Found: C, 55.63; H, 6.66; N, 3.94.

EXAMPLE 56

Preparation of 4-(p-trifluoromethylphenyl)-4-dimethylaminocyclohexanone, ethylene ketal hydrochloride Following substantially the same procedure as described in Example 55, but substituting 4.79 gm. (0.024 mole) p-trifluoromethylbromobenzene for the 4.79 gm. (0.024 mole) m-trifluoromethylbromobenzene, there is prepared 0.90 gm. (34% yield) of 4-(p-trifluoromethylphenyl)-4-dimethylaminocyclohexanone, ethylene ketal hydrochloride having a melting point at 243° to 244° C.

Analysis: Calc'd. for $C_{17}H_{23}ClF_3NO_2 \cdot \frac{1}{2}H_2O$: C, 54.47; H, 6.45; N, 3.74. Found: C, 54.56; H, 6.24; N, 4.13.

EXAMPLE 57

Preparation of 4-(p-chlorophenyl)-2-methyl-4-dimethylaminocyclohexanone

A solution consisting of 0.51 gm. (0.005 mole) diisopropylamine in 10 ml. tetrahydrofuran is chilled in an ice:methanol bath and 3 ml. of 1.68 N butyllithium in pentane is added. To this mixture is then added a solution consisting of 1.25 gm. (0.005 mole) 4-(p-chlorophenyl)-4-dimethylaminocyclohexanone (prepared in Example 2) in 20 ml. tetrahydrofuran. After 5 min. stirring, 1.42 gm. methyl iodide is added. This reaction is stirred for another 30 min. in the cold, and then it is allowed to warm up to 25° C. Striring is continued for 2½ hours, when 20 ml. saturated aqueous ammonium chloride is added. Benzene is also added. The organic solvents are removed by evaporation under reduced pressure. The residue thus obtained is transferred to a chromatographic column containing 200 ml. silica gel. The chromatogram is developed with 2 liters of a mixture of 3% methanol in methylene chloride followed by 2 liters of a mixture of 5% methanol in methylene chloride. The appropriate fractions as determined by TLC are combined. The solvent is removed by evaporation under reduced pressure giving the desired 4-(p-chlorophenyl)-2-methyl-4-dimethylaminocyclohexanone. The compound is recrystallized from diethyl ether to give an analytical sample having a melting point at 110° to 111° C. This is recognized to be the cis isomer by NMR spectroscopy.

Analysis: Calc'd. for $C_{15}H_{20}ClNO$: C, 67.78; H, 7.59; N, 5.27. Found: C, 67.75; H, 7.59; N, 5.56.

The corresponding trans isomer is obtained by combining the later series of fractions in the same manner. It is recrystallized from a mixture of diethyl ether and technical hexane to give 0.52 gm. of the isomer having a melting point at 103° to 105° C.

Analysis: Calc'd. for $C_{15}H_{20}ClNO$: C, 67.78; H, 7.59; N, 5.27. Found: C, 68.03; H, 7.61; N, 5.11.

Following the same procedure, but substituting, e.g., ethyl iodide, n-propyl iodide, n-butyl iodide, and n-pentyl iodide, for methyl iodide, there are prepared the corresponding:

4-(p-chlorophenyl)-2-ethyl-4-dimethylaminocyclohexanone, 4-(p-chlorophenyl)-4-dimethylamino-2-n-propylcyclohexanone, 2-n-butyl-4-(p-chlorophenyl)-4-dimethylaminocyclohexanone, 4-(p-chlorophenyl)-4-dimethylamino-2-n-pentylcyclohexanone, respectively.

EXAMPLE 58

Preparation of 2-methyl-4-dimethylamino-4-(p-tolyl)cyclohexanone

A solution consisting of 1.02 gm. (0.010 mole) diisopropylamine in 20 ml. tetrahydrofuran was chilled in an ice:methanol bath before 6 ml. of 1.68 N butyllithium in pentane is added. To this mixture is then added a solution consisting of 2.31 gm. (0.010 mole) of 4-dimethylamino-4-(p-tolyl)cyclohexanone (prepared in Example 14) and 40 ml. tetrahydrofuran. Five minutes later, 2.82 gm. methyl iodide is added, and the mixture is stirred for 45 min. in the cold. It is allowed to warm to 25° C. and stirring is continued for 5 hours, when the reaction mixture is diluted with a mixture of water and benzene. The organic layer is separated and washed first with water and then with brine. The organic solvents are removed by evaporation under reduced pressure, and the residual waxy solid thus obtained is transferred to a column of the grade silica gel 1" by 48". The chromatogram is developed with a solvent medium consisting of 7.5% methanol in chloroform and 20-ml. fractions are collected. The fractions which contain product (as determined by TLC) are combined. The solvent is removed by evaporation under reduced pressure, and the residue thus obtained is recrystallized from diethyl ether. There is thus obtained 1.01 gm. (39% yield) of the object compound 2-methyl-4-dimethylamino-4-(p-tolyl)cyclohexanone having a melting point at 102° to 104.5° C. NMR suggests assignment of cis relationship of 2-methyl to 4—N(CH$_3$)$_2$.

Analysis: Calc'd. for C$_{16}$H$_{23}$NO: C, 78.32; H, 9.45; N, 5.71. Found: C, 78.03; H, 9.51; N, 5.65.

EXAMPLE 59

Following the procedure of Example 58, but separately substituting 4-(p-chlorophenyl)-4-diethylaminocyclohexanone, 4-(p-chlorophenyl)-4-dipropylaminocyclohexanone, 4-(p-chlorophenyl)-4-di-n-butylaminocyclohexanone, and 4-(p-chlorophenyl)-4-(N-methyl-N-cyclopropylamino)cyclohexanone, for the 4-dimethylamino-4-(p-tolyl)cyclohexanone, there are prepared the corresponding object compounds:

4-(p-chlorophenyl)-4-diethylamino-2-methylcyclohexanone, 4-(p-chlorophenyl)-4-dipropylamino-2-methylcyclohexanone, 4-(p-chlorophenyl)-4-di-n-butylamino-2-methylcyclohexanone, and 4-(p-chlorophenyl)-4-(N-methyl-N-cyclopropylamino)-2-methylcyclohexanone, respectively.

EXAMPLE 60

Preparation of
4-(m-hydroxyphenyl)-4-n-propylmethylaminocyclohexanone ethylene ketal hydrochloride Following the procedure of Example 40, Parts F and G, but substituting the appropriate quantity of propionyl chloride for butyryl chloride, and the appropriate intermediate subsequently, the title compound is obtained as a crystalline solid (m.p. 204°–207° C.).

Analysis: Calc'd. for C$_{18}$H$_{28}$O$_3$NCl: C, 63.23; H, 8.25; N, 4.10. Found: C, 63.13; H, 8.42; N, 3.95.

EXAMPLE 61

Preparation of
4-(m-hydroxyphenyl)-4-(methyl-n-pentylamino)cyclohexanone ethylene ketal hydrochloride Following the procedure of Example 40, Parts F and G, but substituting the appropriate quantity of valeryl chloride (pentanoyl chloride) for butyryl chloride, and the appropriate intermediate subsequently, the title compound is obtained as a gum.

Analysis: Calc'd. for C$_{20}$H$_{32}$O$_3$NCl.½H$_2$O: C, 63.68; H, 8.78; N, 3.70. Found: C, 63.61; H, 8.92; N, 3.50.

EXAMPLE 62

Preparation of
4-(m-hydroxyphenyl)-4-(N-methyl-N-$\beta$-phenylethylamino)cyclohexanone ethylene ketal hydrochloride Following the procedure of Example 40, Parts F and G, but substituting the appropriate quantity of phenylacetyl chloride for n-butyryl chloride, and the appropriate intermediate subsequently, the title compound is obtained as an amorphous solid. The NMR and mass spectra are consistent with the assigned structure.

Analysis: Calc'd. for C$_{23}$H$_{30}$O$_3$NCl: C, 71.20; H, 7.80; N, 3.61. Found: C, 66.64; H, 7.47; N, 3.46.

EXAMPLE 63

Preparation of
4-(m-hydroxyphenyl)-4-(i-butylmethylamino)cyclohexanone ethylene ketal hydrochloride Following the procedure of Example 40, Parts F and G, but substituting the appropriate quantity of 2-methylpropanoyl chloride for n-butyryl chloride, and the appropriate intermediate subsequently, the title compound is obtained as a crystalline solid (m.p. 203°–204° C.).

Analysis: Calc'd. for C$_{19}$H$_{30}$O$_3$HCl: C, 64.12; H, 8.57; N, 3.94. Found: C, 64.14; H, 8.66; N, 4.30.

EXAMPLE 64

Preparation of
4-(m-hydroxyphenyl)-4-(N-methyl-N-cyclopropylmethylamino)cyclohexanone ethylene ketal hydrochloride Following the procedure of Example 40, Parts F and G, but substituting the appropriate quantity of cyclopropanecarbonyl chloride for n-butyryl chloride, and the appropriate intermediate subsequently, the title compound is obtained as a crystalline solid (m.p. 214°–215° C.).

Analysis: Calc'd. for C$_{19}$H$_{28}$O$_3$NCl: C, 64.48; H, 7.97; N, 3.96. Found: C, 64.21; H, 8.08; N, 3.86.

EXAMPLE 65

Part A:
4-(m-benzyloxyphenyl)-4-(N-methyl-N-ethylamino)cyclohexanone ethylene ketal hydroiodide Following the procedure of Example 40, Part F, but substituting the appropriate quantity of acetyl chloride for n-butyryl chloride, there is obtained a material which is dissolved in methylene chloride and this solution is washed with 20% aqueous hydrogen iodide. The solid which remains when the solution is taken to dryness is recrystallized from methylene chloride:ethyl acetate to give crystalline 4-(m-benzyloxyphenyl)-4-(N-methyl-N-ethylamino)cyclohexanone ethylene ketal hydroiodide, m.p. 195°–196.5° C.

Analysis: Calc'd. for C$_{24}$H$_{32}$INO: C, 56.60; H, 6.33; N, 2.75. Found: C, 56.53; H, 6.48; N, 2.93.

Part B

Hydrogenolysis of the compound prepared in Part A, over inert catalyst, gives the corresponding 4-(m-hydroxyphenyl)-4-(N-methyl-N-ethylamino)cyclohexanone ethylene ketal.

EXAMPLE 66

Part A:
4-(m-benzyloxyphenyl)-4-(N-methyl-N-$\beta$-phenoxyethylamino)cyclohexanone, ethylene ketal hydrochloride Following the procedure of Example 40, Part F but substituting phenoxyacetyl chloride for n-butyryl chloride there is obtained the title compound. Recrystallization from methylene chloride-ethyl acetate gives the product, m.p. 173°–174° C.

Analysis: Calc'd. for C$_{30}$H$_{34}$ClNO$_4$: C, 70.92; H, 6.75; N, 2.76. Found: C, 70.81; H, 7.08; N, 2.62.

Part B

Hydrogenolysis of the compound prepared in Part A, over inert catalyst, gives the corresponding 4-(m-hydroxyphenyl)-4-(N-methyl-N-$\beta$-phenoxyethylamino)cyclohexanone, ethylene ketal.

EXAMPLE 67

4-(m-acetoxyphenyl)-4-dimethylaminocyclohexan-1-one

To a solution of 0.96 g. (4.1 mmole) of 4-(m-hydroxyphenyl)-4-dimethylaminocyclohexan-1-one (prepared in Example 44) in 20 ml. THF there is added 0.46 g. (0.63 ml.) triethylamine and 0.46 g. (0.42 ml.) acetic anhydride. Following 6 hours standing at room temperature the mixture is concentrated in vacuum and the residue diluted with ice:water. The precipitated gum is extracted with methylene chloride. The extract is washed with saturated sodium bicarbonate and brine and taken to dryness. The residue is chromatographed over a 1″×48″ column of TLC grade silica gel. These fractions shown by TLC to contain product are collected and taken to dryness. The solid which remained is recrystallized from petroleum ether to give 0.30 g. of 4-(m-acetoxyphenyl)-4-dimethylaminocyclohexan-1-one, m.p. 51°-53° C.

Analysis: Calc'd. for $C_{16}H_{21}NO_3$: C, 69.79; H, 7.69; N, 5.09. Found: C, 69.47; H, 7.89; N, 5.21.

EXAMPLE 68

Following the procedure of Example 67, but substituting 4-(m-hydroxyphenyl)-4-(methyl-n-butylamino)-cyclohexanone (prepared in Example 40, Part H) for 4-(m-hydroxyphenyl)-4-(dimethylamino)cyclohexanone there is obtained the desired 4-(m-acetoxyphenyl)-4-(methyl-n-butylamino)cyclohexanone as the hydrochloride.

Analysis: Calc'd. for $C_{19}H_{27}NO_3 \cdot HCl \cdot \tfrac{3}{8}H_2O$: C, 62.36; H, 8.17; N, 3.82. Found: C, 62.07; H, 7.81; N, 3.80.

EXAMPLE 69 Preparation of 4-phenyl-4-(1-pyrrolidinyl)cyclohexanone, ethylene ketal, hydrochloride A reaction mixture consisting of the free base from 2.69 gm. (0.01 mole) of 4-amino-4-phenylcyclohexanone, ethylene ketal hydrochloride (prepared in Example 32, above) 2.16 gm. of 1,4-dibromobutane, 2.76 gm. potassium carbonate, and 15.0 ml. ethanol is heated at the reflux temperature, with stirring, for eighteen (18) hours. The volatile components are then substantially removed by evaporation under reduced pressure, and the concentrate thus obtained diluted with water. A precipitate forms which is collected on a filter and dissolved in diethyl ether. The ether solution is treated with an equivalent of 3 N hydrogen chloride in diethyl ether. A precipitate that forms is collected on a filter and recrystallized from a mixture of methylene chloride and ethyl acetate. There is thus obtained 1.57 gm. (49% yield) of 4-phenyl-4-(1-pyrrolidinyl)cyclohexanone, ethylene ketal hydrochloride having a melting range from 238° to 239.5° C.

Analysis: Calc'd. for $C_{18}H_{26}ClNO_2$: C, 66.75; H, 8.09; N, 4.33. Found: C, 66.38; H, 8.25; N, 4.30.

EXAMPLE 70

Preparation of 4-phenyl-4-(1-pyrrolidinyl)cyclohexanone

A reaction solution consisting of 1.57 gm. (0.0049 mole) 4-phenyl-4-(1-pyrrolidinyl)cyclohexanone, ethylene ketal hydrochloride (prepared in Example 69, above), 7.0 ml. of 2.5 N hydrochloric acid, and 14.0 ml. methanol is set aside at 25° C. for sixty-six (66) hours. After cooling and removing most of the liquid and volatiles by evaporation under reduced pressure, the residue is made strongly basic with 50% aqueous sodium hydroxide. A precipitate that forms is collected on a filter and then recrystallized from petroleum ether. There is thus obtained 0.77 gm. (65% yield) of 4-phenyl-4-(1-pyrrolidinyl)cyclohexanone having a melting point at 75° to 76.5° C.

Analysis: Calc'd. for $C_{16}H_{21}NO$: C, 78.97; H, 8.70; N, 5.76. Found: C, 79.03; H, 8.73; N, 5.75.

EXAMPLE 71

Preparation of 4-phenyl-4-(1-piperidinyl)cyclohexanone, ethylene ketal hydrochloride A reaction mixture consisting of the free base from 2.88 gm. (0.011 mole) of 4-amino-4-phenylcyclohexanone ethylene ketal hydrochloride (prepared in Example 32, above), 3.47 gm. 1,5-diiodopentane, 2.95 gm. potassium carbonate, and 25 ml. ethanol is heated at the reflux temperature, with stirring, for eighteen (18) hours. After cooling and removing most of the liquid and volatiles by evaporation under reduced pressure, the residue thus obtained is dispersed in a mixture of 100 ml. of diethyl ether and 10 ml. of water. The ether layer is allowed to separate and is recovered. It is washed with water and with brine, before removing the ether by evaporation under reduced pressure. The residue thus obtained is dissolved in diethyl ether and an amount of 3 N hydrogen chloride in diethyl ether is added so as to form the hydrochloride acid addition salt which precipitates. The salt is collected on a filter and then recrystallized from a mixture of methylene chloride and ethyl acetate. There is thus obtained 2.26 gm. (61% yield) of 4-phenyl-4-(1-piperidinyl)cyclohexanone, ethylene ketal hydrochloride having a melting range from 228° to 231° C. An analytical sample has a melting point at 234° to 235.5° C.

Analysis: Calc'd. for $C_{19}H_{28}ClNO_2$: C, 67.54; H, 8.35; N, 4.14. Found: C, 67.24; H, 8.12; N, 3.97.

EXAMPLE 72

Preparation of 4-phenyl-4-(1-piperidinyl)cyclohexanone

A reaction solution consisting of 2.26 gm. (0.0067 mole) of 4-phenyl-4-(1-piperidinyl)cyclohexanone, ethylene ketal hydrochloride (prepared in Example 71, above), 10 ml. of 2.5 N hydrochloric acid and 20 ml. methanol is set aside in a stoppered reaction vessel at 25° C. for four (4) days. After removing most of the solvent by evaporation under reduced pressure, the residue is made strongly basic with 50% aqueous sodium hydroxide. A precipitate forms which is collected on a filter and recrystallized two times from a mixture of acetone and technical hexane. There is thus obtained 0.94 gm. (55% yield) of 4-phenyl-4-(1-piperidinyl)cyclohexanone having a melting range from 114° to 117° C.

Analysis: Calc'd. for $C_{17}H_{23}NO$: C, 79.33; H, 9.01; N, 5.44. Found: C, 79.16; H, 9.15; N, 5.31.

EXAMPLE 73

Part A

Following the procedure of Example 32 but substituting the appropriate quantity of 4-isocyanato-4-(m-methoxyphenyl)cyclohexanone ethylene ketal (prepared in Example 11, Part F, above) for 4-phenyl-4-isocyanatocyclohexanone ethylene ketal there is obtained 4-amino-4-(m-methoxyphenyl)cyclohexanone, ethylene ketal hydrochloride (alternate name: 4-amino-4-(m-anisyl)cyclohexanone, ethylene ketal hydrochloride).

Part B

Following the procedure of Example 69 but substituting the appropriate quantity of 4-amino-4-(m-methoxyphenyl)cyclohexanone ethylene ketal hydrochloride (prepared in Part A, above) for the 4-amino-4-phenylcyclohexanone, ethylene ketal hydrochloride there is obtained 4-(1-pyrrolidinyl)-4-(m-methoxyphenyl)cyclohexanone ethylene ketal hydrochloride.

Part C

Following the procedure of Example 70 but substituting an appropriate quantity of 4-(m-anisyl)-4-(1-pyrrolidinyl)cyclohexanone ethylene ketal hydrochloride (prepared in Part B, above) for 4-phenyl-4-(1-pyrrolidinyl)cyclohexanone ethylene ketal hydrochloride there is obtained 4-(m-anisyl)-4-(1-pyrrolidinyl)cyclohexanone.

Part D

Following the procedure of Example 40, Part A, but substituting an appropriate quantity of 4-(m-anisyl)-4-(1-pyrrolidinyl)cyclohexanone (prepared in Part C, above) for the 4-cyano-4-(m-anisyl)cyclohexanone there is obtained 4-(m-hydroxyphenyl)-4-(1-pyrrolidinyl)cyclohexanone.

Part E

Following the procedure of Example 40, Part B, but substituting an appropriate quantity of 4-(m-hydroxyphenyl)-4-(1-pyrrolidinyl)cyclohexanone (prepared in Part D, above) for 4-cyano-4-(m-hydroxyphenyl)cyclohexanone there is obtained 4-(m-hydroxyphenyl)-4-(1-pyrrolidinyl)cyclohexanone, ethylene ketal.

Part F

Following the procedure of Example 67, Part A, but substituting an appropriate quantity of 4-(m-hydroxyphenyl)4-(1-pyrrolidinyl)cyclohexanone (prepared in Part D, above) for 4-(m-hydroxyphenyl)-4-(dimethylamino)cyclohexanone there is obtained 4-(m-acetoxyphenyl)-4-(1-pyrrolidinyl)cyclohexanone.

EXAMPLE 74

Part A

Following the procedure of Example 32 but separately substituting the appropriate quantity of each of the 4-isocyanato intermediates prepared in Examples 1-27 (Parts F) and Example 31, Part A, for 4-isocyanato-4-phenylcyclohexanone ethylene ketal there is obtained, respectively, each corresponding 4-aryl-4-aminocyclohexanone, ethylene ketal hydrochloride.

Part B

Following the procedure of Example 69 but separately substituting each amino compound prepared in Part A above for 4-phenyl-4-aminocyclohexanone ethylene ketal hydrochlochloride and 2-methyl-1,4-dibromobutane for 1,4-dibromobutane there is prepared, respectively, each corresponding 4-aryl-4-(3-methyl-1-pyrrolidinyl)cyclohexanone ethylene ketal hydrochloride.

Part C

Each product compound prepared in Part B, above, can be hydrolyzed to the corresponding ketone, following the procedure of Example 70 but substituting an appropriate quantity of each ethylene ketal hydrochloride (Part B, above) for 4-(phenyl)-4-(1-pyrrolidinyl)cyclohexanone ethylene ketal hydrochloride.

EXAMPLE 75

Part A

Following the procedure of Example 71 but separately substituting appropriate quantities of each amino compound prepared in Example 74, Part A, for 4-phenyl-4-aminocyclohexanone ethylene ketal hydrochloride, and 3-ethyl-1,5-diiodopentane for the 1,5-diiodopentane there are prepared, respectively, the corresponding 4-aryl-4-(4-ethyl-1-piperidinyl)cyclohexanone ethylene ketal hydrochlorides.

Part B

Following the procedure of Example 72 but separately substituting an appropriate quantity of each ketal prepared in Part A, above, for 4-phenyl-4-(1-piperidinyl)cyclohexanone, ethylene ketal hydrochloride there are obtained, respectively, the corresponding 4-aryl-4-(4-ethyl-1-piperidinyl)cyclohexanones.

EXAMPLE 76

Following the procedure of Example 42, Part B, but separately substituting the appropriate quantity of each intermediate prepared in Example 50, Part B, for the 4-cyano-4-(methyl-n-butylamino)cyclohexanone ethylene ketal there are prepared the corresponding compounds:

4-(m-hydroxyphenyl)-4-dimethylaminocyclohexanone trimethylene ketal (m.p. 147°-150° C.)
Analysis: Calc'd. for $C_{17}H_{25}NO_3$: C, 70.07; H, 8.65; N, 4.81. Found: C, 69.67; H, 8.45; N, 5.07.

4-(m-hydroxyphenyl)-4-dimethylaminocyclohexanone (2,2-dimethyltrimethylene) ketal
Analysis: Calc'd. for $C_{19}H_{29}NO_3$: C, 71.44; H, 9.15; N, 4.39. Found: C, 70.76; H, 9.22; N, 4.57.

4-(m-hydroxyphenyl)-4-dimethylaminocyclohexanone, (2-phenyltrimethylene) ketal
Analysis: Calc'd. for $C_{23}H_{29}NO_3$: C, 75.17; H, 7.95; N, 3.81. Found: C, 74.79; H, 8.04; N, 4.09.

4-(m-hydroxyphenyl)-4-dimethylaminocyclohexanone, (2-allyltrimethylene) ketal
Analysis: Calc'd. for $C_{20}H_{29}NO_3$: C, 72.47; H, 8.82; N, 4.23. Found: C, 72.15; H, 9.01; N, 4.42.

EXAMPLE 77

Part A

Following the procedure of Example 42, Part A, but substituting the appropriate quantity of allylmethylamine for methyl-n-butylamine, stirring at room temperature for 2 days and extracting the reaction mixture with diethyl ether there is obtained, on recrystallization from petroleum ether, crystalline product, 4-cyano-4-(N-methyl-N-allylamino)cyclohexanone ethylene ketal, m.p. 47°-50° C. (Mass spec. m/e+(M+)=236).

Analysis: Calc'd. for $C_{13}H_{20}N_2O_2$: C, 66.07; H, 8.53; N, 11.86. Found: C, 66.85; H, 8.65; N, 11.69.

Part B

Following the procedure of Example 42, Part B, but substituting 4-cyano-4-(N-methyl-N-allylamino)cyclohexanone ethylene ketal (prepared in Part A) for 4-cyano-4-(methyl-n-butylamino)cyclohexanone ethylene ketal, and purifying by high-pressure liquid chromatography followed by recrystallization there is obtained the object compound 4-(m-hydroxyphenyl)-4-(N-allyl-N-methylamino)cyclohexanone ethylene ketal.

Analysis: Calc'd. for $C_{18}H_{25}NO_3 \cdot \frac{3}{8}H_2O$: C, 68.54; H, 8.40; N, 4.44. Found: C, 68.62; H, 8.45; N, 4.32.

EXAMPLE 78

Part A

Following the procedure of Example 1, Parts A–H, but initially substituting 1-naphthylacetonitrile for p-chlorophenylacetonitrile and subsequently substituting each intermediate appropriately there is obtained 4-(1-naphthyl)-4-dimethylaminocyclohexanone ethylene ketal, m.p. 132°–135° C.

Analysis: Calc'd. for $C_{20}H_{25}NO_2$: C, 77.13; H, 8.09; N, 4.50. Found: C, 76.93; H, 8.40; N, 4.48.

Part B

Following the procedure of Example 2 but substituting the product from Part A for 4-(p-chlorophenyl)-4-dimethylaminocyclohexanone ethylene ketal hydrochloride there is obtained 4-(1-naphthyl)-4-dimethylaminocyclohexanone.

Analysis: Calc'd. for $C_{18}H_{21}NO.\frac{1}{4}H_2O$: C, 79.52; H, 7.97; N, 5.15. Found: C, 79.76; H, 8.04; N, 5.22.

EXAMPLE 79

Following the procedure of Example 44, but separately substituting the appropriate quantities of the final compounds prepared in Examples 60 through 64 for 4-(m-hydroxyphenyl)-4-dimethylaminocyclohexanone, ethylene ketal there are prepared 4-(m-hydroxyphenyl)-4-(n-propylmethylamino)cyclohexanone (m.p. 116°–118° C.)

Analysis: Calc'd. for $C_{16}H_{23}NO_2$: C, 73.53; H, 8.87; N, 5.36. Found: C, 73.29; H, 8.96; N, 5.67.

4-(m-hydroxyphenyl)-4-(n-pentylmethylamino)cyclohexanone, 4-(m-hydroxyphenyl)-4-(N-β-phenylethyl-N-methylamino)cyclohexanone, 4-(m-hydroxyphenyl)-4-(i-butylmethylamino)cyclohexanone, and 4-(m-hydroxyphenyl)-4-(N-cyclopropylmethyl-N-methylamino)cyclohexanone,

EXAMPLE 80

Following the procedure of Example 67, but substituting 4-(m-hydroxyphenyl)-4-(N-β-phenylethyl-N-methylamino)cyclohexanone, 4-(m-hydroxyphenyl)-4-(n-propylmethylamino)cyclohexanone, 4-(m-hydroxyphenyl)-4-(n-pentylmethylamino)cyclohexanone, 4-(m-hydroxyphenyl)-4-(isobutylmethylamino)cyclohexanone, and 4-(m-hydroxyphenyl)-4-(cyclopropylmethylmethylamino)-cyclohexanone prepared in Example 79 (above) for 4-(m-hydroxyphenyl)-4-dimethylaminocyclohexanone there are obtained, respectively, 4-(m-acetoxyphenyl)-4-(N-β-phenylethyl-N-methylamino)cyclohexanone, 4-(m-acetoxyphenyl)-4-(N-propylmethylamino)cyclohexanone, 4-(m-acetoxyphenyl)-4-(n-pentylmethylamino)cyclohexanone, 4-(m-acetoxyphenyl)-4-(isobutylmethylamino)cyclohexanone, and 4-(m-acetoxyphenyl)-4-(cyclopropylmethylamino)cyclohexanone.

EXAMPLE 81

Following the procedure of Example 67 but substituting propionic anhydride and butyric anhydride for acetic anhydride there are prepared 4-(m-propionoxyphenyl)-4-dimethylaminocyclohexanone, 4-(m-n-butyroxyphenyl)-4-dimethylaminocyclohexanone.

EXAMPLE 82

Following the procedure of Example 68 but substituting propionic anhydride and n-butyric anhydride for acetic anhydride, there are obtained 4-(m-propionoxyphenyl)-4-(methyl-n-butylamino)cyclohexanone, and 4-(m-n-butyroxyphenyl)-4-(methyl-n-butylamino)cyclohexanone, respectively.

EXAMPLE 83

Preparation of 4-phenyl-4-diethylaminocyclohexanone hydrochloride

Part A

Following the procedure for Example 47, Part B, but substituting bromobenzene for the tetrahydropyranyl ether of m-bromophenol, there is obtained 4-phenyl-4-diethylaminocyclohexanone ethylene ketal.

Part B

Following the procedure of Example 44, but substituting an appropriate quantity of the compound prepared in Part A (above) for 4-(m-hydroxyphenyl)-4-dimethylaminocyclohexanone ethylene ketal, there is obtained the 4-phenyl-4-diethylaminocyclohexanone as the hydrochloride salt, m.p. 175°–177.5° C.

Analysis: Calc'd. for $C_{16}H_{24}NOCl.\frac{1}{4}H_2O$: C, 66.07; H, 8.66; N, 4.81. Found: C, 65.78; H, 8.88; N, 4.98.

EXAMPLE 84

Preparation of 4-dimethylamino-4-(3-hydroxy-4-methylphenyl)cyclohexanone ethylene ketal

Part A

Following the procedure of Example 42, Part B, but substituting the appropriate quantities of 4-cyano-4-dimethylaminocyclohexanone ethylene ketal, prepared in Example 41, Part B, and of the tetrahydropyranyl ether of 3-hydroxy-4-methylbromobenzene for the corresponding ether of m-bromophenol, there is obtained 4-(3-hydroxy-4-methylphenyl)-4-dimethylaminocyclohexanone ethylene ketal which is recrystallized from chloroform/ethyl acetate; m.p. 196°–200° C.

Analysis: Calc'd. for $C_{17}H_{25}NO_3.\frac{1}{4}H_2O$: C, 67.96; H, 8.72; N, 4.66. Found: C, 68.28; H, 8.73; N, 4.90.

The compounds of the Formula I have analgetic activity and can be used for the relief of pain without loss of consciousness. The compounds can be used to treat the pain of headache, muscle spasm, arthritis and other musculoskeletal conditions, e.g., bursitis, relieve mild to moderate postoperative and postpartum pain; dysmenorrhea and pain of traumatic origin. Additionally, the compounds of Formula I can be administered for the treatment of severe pain, e.g., pain associated with adenocarcinoma, amputation of a limb, and third degree burns over a major portion of the body in animals and humans.

Additionally selected compounds of Formula I have activity as narcotic antagonists. They can be used to counteract or prevent excessive central nervous system depression and respiratory depression resulting from the administration of morphine or other morphine like drugs, e.g., hydromorphone, oxymorphone, methadone and meperidine. The compounds are also capable of inducing an abstinence syndrome in narcotic addicted subjects, i.e., induce withdrawal effects for diagnostic purposes.

The dosage of the compound of the Formula I for analgetic purposes is from about 0.01 to about 7 mg./kg. body weight of the patient. The compounds of the Formula I are conveniently prepared in 5, 10, 25, 50, 75, 100 and 200 mg. dosage units for administration for 1 to 4 times a day. Preferred unit dosages are from 0.05 to 4 mg./kg. body weight of the patient.

The compounds are administered orally, parenterally and rectally for systemic action.

The compositions of the present invention are presented for administration to humans and animals in unit dosage forms, such as tablets, capsules, pills, powders, granules, sterile parenteral solutions or suspensions, and oral solutions or suspensions, and oil-water emulsions containing suitable quantities of a compound of Formula I or its pharmacologically acceptable salts.

Pharmaceutical dosage unit forms are prepared in accordance with the subsequent general specific descriptions to provide from about 0.5 mg. to about 500 mg. of the essential active ingredient per dosage unit form (preferred 2.5-300 mg.).

Oral pharmaceutical dosage forms are either solid or liquid. The solid dosage forms are tablets, capsules, granules, and bulk powders. Types of oral tablets are, for example, compressed (including chewable and lozenge), tablet triturates, enteric-coated, sugar-coated, film-coated, and multiple compressed. Capsules are either hard or soft elastic gelatin. Granules and powders are either effervescent or non-effervescent.

Pharmaceutically acceptable substances utilized in compressed tablets are binders, lubricants, diluents, disintegrating agents, coloring agents, flavoring agents, flow inducing agents, and wetting agents. Tablet triturates (either molded or compressed) utilize diluents and binders. Enteric-coated tablets, due to their enteric-coating, resist the action of stomach acid and dissolve or disintegrate in the alkaline intestine. Sugar-coated tablets are compressed tablets to which usually four different layers of pharmaceutically acceptable substances have been applied. Film-coated tablets are compressed tablets which have been coated with a water soluble cellulose polymer. Multiple compressed tablets are compressed tablets made by more than one compression cycle utilizing the pharmaceutically acceptable substances previously mentioned. Coloring agents are utilized in the above dosage forms. Flavoring and sweetening agents are utilized in compressed tablets, tablet triturates, sugar coated, multiple compressed and chewable tablets. Flavoring and sweetening agents are especially useful in the formation of chewable tablets and lozenges.

Examples of binders include glucose solution (25-50%), acacia mucilage (10-20%), gelatin solution (10-20%), sucrose and starch paste. Lubricants include, for example, talc, starch, magnesium or calcium stearate, lycopodium and stearic acid. Diluents include, for example, lactose, sucrose, starch, kaolin, salt, mannitol and dicalcium phosphate. Disintegrating agents include, for example, corn starch, potato starch, bentonite, methylcellulose, agar and carboxymethylcellulose. Coloring agents include, for example, any of the approved certified water soluble FD and C dyes, mixtures thereof, and water insoluble FD and C dyes suspended on alumia hydrate. Sweetening agents include, for example, sucrose, lactose, mannitol, and artificial sweetening agents such as sodium cyclamate and saccharin, and any number of spray dried flavors. Flavoring agents include natural flavors extracted from plants such as fruits and synthetic blends of compounds which produce a pleasant sensation. Flow inducing agents include, for example, silicon dioxide and talc. Wetting agents include, for example, propylene glycol monostearate, sorbitan monooleate, diethylene glycol monolaurate and polyoxyethylene laural ether. Enteric-coatings include, for example, fatty acids, fats, waxes, shellac, ammoniated shellac and cellulose acetate phthalates. Pharmaceutically acceptable substances for the first layer, an undercoating, of sugar-coated tablets, include, for example, dextrin and gelatin. The second layer, an opaque zone, includes, for example, starch, talc, calcium carbonate, magnesium oxide and magnesium carbonate. The third layer, a translucent zone, includes, for example, sucrose. The fourth layer, a glaze, includes, for example, beeswax, carnauba wax, or a mixture of these waxes. Film coatings include, for example, hydroxyethylcellulose, sodium carboxymethylcellulose, polyethylene glycol 4000 and cellulose acetate phthalate.

Hard gelatin capsules, sizes 5 through 1000, are made largely from gelatin and may be either clear or colored. These capsules may be filled with either a powder or coated pellets (sustained release).

The diluents utilized in powder filled capsules are the same as those illustrated above for tablets. Pharmaceutically acceptable substances utilized for coating pellets include, for example, stearic acid, palmitic acid, glyceryl myristate, cetyl alcohol, fats, waxes, polymeric substances sensitive to small changes in pH of the gastrointestinal tract, polyvinyl alcohol, ethyl cellulose and mixtures of beeswax, carnauba wax or bayberry wax with glyceryl monostearate.

Soft elastic gelatin capsules contain sufficient glycerin so that they are permanently flexible. Pharmaceutically acceptable liquid diluents used in soft elastic gelatin capsules are those which do not dissolve or harm the capsule and which are non-toxic, including, for example, corn oil, cottonseel oil, polysorbate 80, DMA and triacetin.

Pharmaceutically acceptable substances utilized in non-effervescent granules, for solution and/or suspension, include diluents, wetting agents, flavoring agents and coloring agents. Examples of diluents, wetting agents, flavoring agents and coloring agents include those previously exemplified.

Pharmaceutically acceptable substances utilized in effervescent granules and powders include organic acids, a source of carbon dioxide, diluents, wetting agents, flavoring agents and coloring agents.

Examples of organic acids include, for example, citric acid and tartaric acid. Sources of carbon dioxide include, for example, sodium bicarbonate and sodium carbonate. Examples of sweetening agents include, for example, sucrose, calcium cyclamate and saccharin. Examples of diluents, wetting agents and coloring agents include those previously exemplified.

Bulk powders have the compound of the Formula I uniformly dispersed throughout a pharmaceutically acceptable powdered carrier diluent. Examples of the diluent include those previously exemplified.

The individual oral solid pharmaceutical dosage forms, tablets and capsules, are packaged individually, unit-dose, or in quantity, multiple-dose containers, for example, bottles of 50, 100, 500, 1000, or 5000.

The amount of compound of the Formula I analog per dose unit is adjusted so that it provides the patient with an effective amount. The exact dose depends on the age, weight and condition of the patient or animal as is known in the art. For example, tablets and capsules are given in sufficient number and frequency to obtain the desired pharmacological effect.

The sustained release tablets and capsules provide an effective amount upon ingestion and continue to release a sufficient amount of the active material to keep the concentration at an effective level for increased periods of time, for example, 12 hours.

Non-effervescent granules and powders are packages in predetermined amounts, such that when reconstituted with a specified quantity of an appropriate liquid vehicle, usually distilled water, a solution and/or suspension results, providing a uniform concentration of the compound of the Formula I after shaking, if necessary. The concentration of the solution is such that a teaspoonful (5 ml.), a tablespoonful (one-half ounce or 15 ml.) or a fraction or a multiple thereof will provide an effective amount to produce the desired pharmacological effect. The exact dose depends on the age, weight and condition of the patient or animal, as is known in the art.

Effervescent granules and powders are packaged either in unit-dose, for example, tin foil packets, or in bulk, for example, in 4 oz. and 8 oz. amounts, such that a specific amount, either a unit-dose or, for example, a teaspoonful, tablespoonful or a fraction or a multiple thereof of bulk granules, when added to a specific amount of liquid vehicle, for example, water, yields a container of liquid dosage form to be ingested. The concentration of the active material in the granules is adjusted so that a specified amount when mixed with a specific amount of water yields an effective amount of the active material and produces the desired pharmacological effect. The exact amount of granules to be used depends on age, weight and condition of the patient as is known in the art.

Liquid oral dosage forms include, for example, aqueous solutions, emulsions, suspension, solutions and/or suspensions reconstituted from non-effervescent granules and effervescent preparations reconstituted from effervescent granules. Aqueous solutions include, for example, elixirs and syrups. Emulsions are either oil-in-water (o/w) or water-in-oil (w/o).

Elixirs are clear, sweetened, hydroalcoholic preparations. Pharmaceutically acceptable substances utilized in elixirs include, for example, solvents. Syrups are concentrated aqueous solutions of a sugar, for example, sucrose, and may contain a preservative. An emulsion is a two-phase system in which one liquid is dispersed in the form of small globules throughout another liquid. O/w emulsions are much preferred for oral administration over w/o emulsions. Pharmaceutically acceptable substances utilized in emulsions are non-aqueous liquids, emulsifying agents and preservatives. Syspensions utilize pharmaceutically acceptable suspending agents and preservatives. Pharmaceutically acceptable substances utilized in non-effervescent granules, to be reconstituted into a liquid oral dosage form, include, for example, diluents, sweeteners, and wetting agents. Pharmaceutically acceptable substances utilized in effervescent granules, to be reconstituted into a liquid oral dosage form, include, for example, organic acids and a source of carbon dioxide. Coloring and flavoring agents are utilized in all of the above dosage forms.

Solvents include, for example, glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include, for example, mineral oil and cottonseed oil. Examples of emulsifying agents include for example, gelatin, acacia, tragacanth, bentonite, and surfactants such as polyoxyethylene sorbitan monooleate. Suspending agents include, for example, sodium carboxymethylcellulose, pectin, tragacanth, Veegum and acacia. Diluents include, for example, lactose and sucrose. Sweetening agents include, for example, sucrose, syrups, glycerin, and artificial sweetening agents such as sodium cyclamate and saccharin. Wetting agents include, for example, propylene glycol monostearate, sorbitan monooleate, diethylene glycol monolaurate and polyoxyethylene lauryl ether. Organic acids include, for example, citric and tartaric acid. Sources of carbon dioxide include, for example, sodium bicarbonate and soidum carbonate. Coloring agents include, for example, any of the approved, certified water soluble FD and C dyes, and mixtures thereof. Flavoring agents includie, for example, natural flavors extracted from plants such as fruits, and synthetic blends of compounds which produce a pleasant taste sensation.

The concentration of the compound of the Formula I throughout the solutions must be uniform. Upon shaking, the concentration of the compound of the Formula I throughout the emulsions and suspensions must be uniform.

The concentration of the compound of the Formula I is adjusted so that a teaspoonful (5 ml.), a tablespoonful (one-half ounce or 15 ml.) or a fraction or multiple thereof, will provide an effective amount to produce the desired pharmacological effect. The exact dose depends on the age, weight and condition of the patient or animal as is known in the art.

The liquid oral dosage forms may be packaged, for example, in unit-dose sizes of 5 ml. (teaspoonful), 10 ml., 15 ml. (tablespoonful) and 30 ml. (one ounce), and multiple dose containers, including, for example, 2 oz., 3 oz., 4 oz., 6 oz., 8 oz., pint, quart, and gallon sizes.

Non-effervescent granules are packaged in predetermined amounts such that when reconstituted with a specified quantity of an appropriate liquid vehicle, usually distilled water, a solution and/or suspension results providing a uniform concentration of the compound of the Formula I after shaking, if necessary. The concentration of the solution is such that a teaspoonful (5 ml.), a tablespoonful (one-half ounce or 15 ml.) or a fraction or multiple thereof will provide an effective amount to produce the desired pharmacological effect. The exact does depends on the age, weight, and condition of the patient or animal as is known in the art.

Effervescent granules are packaged either in unit-dose, for example, tin foil packets or in bulk, for example, in 4 oz. and 8 oz. amounts such that a specific amount, either a unit-dose or for example, a teaspoonful, tablespoonful or a fraction or multiple thereof of bulk granules when added to a specific amount of liquid vehicle, for example, water yields a container of liquid dosage form to be ingested. The concentration of the compound of the Formula I in the granules is adjusted so that a specified amount when mixed with a specific amount of water yields an effective amount of the active material to produce the desired pharmacological effect. The exact amount of granules to be used depends on age, weight and condition of the patient as it known in the art.

Parenteral administration includes intravenous, subcutaneous, intramuscular, and the like.

Preparations for parenteral administration include sterile solutions ready for injection, sterile dry soluble products ready to be combined with a solvent just prior to use, including hypodermic tablets, sterile suspensions ready for injection, sterile dry insolbule products ready to be combined with a vehicle just prior to use and sterile emulsions. The solutions may be either aqueous or non-aqueous.

Pharmaceutically acceptable substances utilized in parenteral preparations include aqueous vehicles, non-aqueous vehicles, antimicrobial agents, isotonic agents, buffers, antioxidants, local anesthetics, suspending and dispersing agents, emulsifying agents, sequestering or chelating agents and other pharmaceutical necessities.

Examples of aqueous vehicles include Sodium Chloride Injection, Ringers Injection, Isotonic (5 percent) Dextrose Injection, Sterile Water for Injection, Dextrose and Sodium Chloride Injection and Lactated Ringers Injection. Non-aqueous parenteral vehicles include fixed oils of vegetable origin, for example, cottonseed oil, corn oil, sesame oil and peanut oil. Antimicrobial agents in bacteriostatic or fungistatic concentrations must be added to parenteral preparations packaged in multiple-dose containers (vials) which include phenol or cresols, mercurials, benzyl alcohol, chlorobutanol, methyl and propyl p-hydroxybenzoic acid esters, thimerosal, benzalkonium chloride and benzethonium chloride. Isotonic agents include, for example, sodium chloride and dextrose. Buffers include, for example, phosphate and citrate. Antioxidants include, for example, sodium bisulfiate. Local anesthetics include, for example, procaine hydrochloride. Suspending and dispersing agents include, for example, sodium carboxymethylcellulsoe, hydroxypropyl methylcellulose and polyvinylpyrrolidone. Emulsifying agents include, for example, Polysorbate 80 (Tween 80). A sequestering or chelating agent of metal ions include, for example, EDTA (ethylenediaminetetraacetatic acid). Pharmaceutical necessities include, for example, ethyl alcohol, polyethylene glycol and propylene glycol for water miscible vehicles and sodium hydroxide, hydrochloric acid, citric acid or lactic acid for pH adjustment.

The concentration of the pharmaceutically active ingredient is adjusted so that an injection, for example, 0.5 ml., 1.0 ml., 2.0 ml., and 5.0 ml. or an intraarterial or intravenous infusion, for example, 0.5 ml./min., 1.0 ml./min., 1.0 ml./min., and 2.0 ml./min. provides an effective amount to produce the desired pharmacological effect. The exact dose depends on the age, weight and condition of the patient or animal as is known in the art.

The unit-dose parenteral preparations are packaged, for example, in an ampul or a syringe with a needle. The multiple-dose package, for example, is a vial.

All preparations for parenteral administration must be sterile, as is known and practiced in the art.

Illustratively, intravenous or intraarterial infusion of a sterile aqueous solution containing an active material is an effective mode of administration. Another embodiment is a sterile aqueous or oily solution or suspension containing an active material injected as necessary to produce the desired pharmacological effect.

Pharmaceutical dosage forms for rectal administration are rectal suppositories, capsules, tablets for systemic effect.

Rectal suppositories are used herein mean solid bodies for insertion into the rectum which melt or soften at body temperature releasing one or more pharmacologically or therapeutically active ingredients.

Pharmaceutically acceptable substances utilized in rectal suppositories are bases or vehicles and agents to raise the melting point.

Examples of bases or vehicles include, for example, cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include, for example, spermaceti and wax. Rectal suppositories may be prepared either by the compressed method or by molding. The usual weight of a rectal suppository is about 2.0 gm.

Tablets and capsules for rectal administration are manufactured utilizing the same pharmaceutically acceptable substance and by the same methods as for formulations for oral administration.

Rectal suppositories, tablets or capsules are packaged either individually, in unit-dose, or in quantityt, multiple dose, for example, 2, 6, or 12.

The pharmaceutically therapeutically active compounds of the Formula I are administered orally, parenterally or rectally in unit-dosage forms or multiple-dosage forms. Unit-dose forms as used in the specification and claims refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampuls and syringes (parenteral), individually packaged tablet or capsule (oral-solid) or individually packaged teaspoonful or tablespoonful (oral-liquid). Unit-dose forms may be administered in fractions or multiples thereof. A multiple-dose form is a plurality of identical unit-dosage forms packaged in a single container to be administered in segregated unit-dose form. Examples of multiple-dose forms include vials (parenteral), bottles of tablets or capsules (oral-solid) or bottles of pints or gallons (oral-liquid). Hence, multiple dose form is a multiple of unit-doses which are not segregated in packaging. The specifications for the unit-dosage form and the multiple-dosage form are dictated by and directly dependent on (a) the unique characteristics of the therapeutically active compound and the particular therapeutic effect to be achieved and (b) the limitations inherent in the art of compounding such a therapeutically active compound for therapeutic or prophylactic.

In addition to the administration of a compound of Formula I as the principal active ingredient of compositions for the treatment of the conditions described herein, the said compound can be included with other types of compounds to obtain advantageous combinations of properties. Such combinations include a compound of Formula I with other analgesics such as aspirin, phenacetin acetaminophen, propoxyphene, pentazocine, codeine, meperidine, oxycodone, mefenamic acid, and ibuprofen; muscle relaxants such as methocarbamol, orphenadrine, carisoprodol, meprobamate, chlorphenesin carbamate, diazepam, chlordiazepoxide, and chlorzoxazone; analeptics such as caffeine, methylphenidate and pentylenetetrazol; corticosteroids such as methylprednisolone, prednisone, prednisolone and dexamethasone; antihistamines such as chlorpheniramine, cyproheptadine, promethazine and pyrilamine.

EXAMPLE 85

Capsules

One thousand two-piece hard gelatin capsules for oral use, each containing 0.5 mg. of 4-(methyl-n-butylamino)-4-(m-hydroxyphenyl)cyclohexan-1-one ethylene ketal hydrochloride are prepared from the following types and amounts of materials:

| | |
|---|---|
| 4-(methyl-n-butylamino)-4-(m-hydrophenol)cyclohexan-1-one ethylene ketal hydrochloride | 0.5 gm. |
| Lactose | 150 gm. |
| Corn Starch | 25 gm. |
| Talc | 20 gm. |
| Magnesium stearate | 2.0 gm. |

The materials are thoroughly mixed and then encapsulated in the usual manner.

The foregoing capsules are useful for the treatment of headache in adult humans by the oral administration of 1 capsule every 4 hours.

Using the procedure above, capsules are similarly prepared containing 4-(methyl-n-butylamino)-4-(m-hydroxyphenyl)cyclohexan-1-one ethylene ketal hydrochloride in 50, 75, 100, and 200 mg. amounts by substituting 50, 75, 100, and 200 gm. of 4-(methyl-n-butylamino)-4-(m-hydroxyphenyl)cyclohexan-1-one ethylene ketal hydrochloride for the 25 gm. used above.

EXAMPLE 86

Capsules

One thousand two-piece hard gelatin capsules for oral use, each containing 100 mg. of 4-(methyl-n-butylamino)-4-(m-hydroxyphenyl)cyclohexan-1-one ethylene ketal hydrochloride and 325 mg. of aspirin, are prepared from the following types and amounts of ingredients:

| | |
|---|---|
| 4-(methyl-n-butylamino)-4-(m-hydroxyphenyl)-cyclohexan-1-one ethylene ketal hydrochloride | 100 gm. |
| Aspirin | 325 gm. |
| Talc | 35 gm. |
| Magnesium stearate | 2.5 gm. |

The ingredients are thoroughly mixed and then encapsulated in the usual manner.

The foregoing capsules are useful for the treatment of headache in adult humans by the oral administration of 1 capsule every 6 hours.

EXAMPLE 87

Tablets

One thousand tablets for oral use, each containing 200 mg. of 4-(methyl-n-butylamino)-4-(m-hydroxyphenyl)-cyclohexan-1-one ethylene ketal hydrochloride are prepared from the following types and amounts of materials:

| | |
|---|---|
| 4-(methyl-n-butylamino)-4-(m-hydroxyphenyl)cyclohexan-1-one ethylene ketal hydrochloride | 200 gm. |
| Lactose | 125 gm. |
| Corn Starch | 65 gm. |
| Magnesium stearate | 2.5 gm. |
| Light liquid petrolatum | 3 gm. |

The ingredients are thoroughly mixed and slugged. The slugs are broken down by forcing through a number sixteen screen. The resulting granules are then compressed into tablets, each tablet containing 200 mg. of 4-(methyl-n-butylamino)-4-(m-hydroxyphenyl)cyclohexan-1-one ethylene ketal hydrochloride.

The foregoing tablets are useful for treatment of arthritic pain in adult humans by oral administration of 1 tablet every 4 hours.

EXAMPLE 88

Tablets

One thousand oral tablets, each containing 100 mg. of 4-(methyl-n-butylamino)-4-(m-hydroxyphenyl)cyclohexan-1-one ethylene ketal hydrochloride and a total of 400 mg. of chlorphenesin carbamate are prepared from the following types and amounts of materials:

| | |
|---|---|
| 4-(methyl-n-butylamino)-4-(m-hydroxyphenyl)cyclohexan-1-one ethylene ketal hydrochloride | 100 gm. |
| Chlorphenesin Carbamate | 400 gm. |
| Lactose | 50 gm. |
| Corn starch | 50 gm. |
| Calcium stearate | 2.5 gm. |
| Light liquid petrolatum | 5 gm. |

The ingredients are thoroughly mixed and slugged. The slugs are broken down by forcing through a number sixteen screen. The resulting granules are then compressed into tablets, each containing 100 mg. of 4-(methyl-n-butylamino)-4-(m-hydroxyphenyl)cyclohexan-1-one ethylene ketal hydrochloride and 400 mg. of chlorphenesin carbamate.

The foregoing tablets are useful for treatment of low back pain by the oral administration of 1 tablet every six hours.

EXAMPLE 89

Oral Syrup

One thousand ml. of an aqueous suspension for oral use, containing in each 5 ml. dose, 100 mg. of 4-(methyl-n-butylamino)-4-(m-hydroxyphenyl)cyclohexan-1-one ethylene ketal hydrochloride is prepared from the following types and amounts of ingredients:

| | |
|---|---|
| 4-(methyl-n-butylamino)-4-(m-hydroxyphenyl)cyclohexan-1-one ethylene ketal hydrochloride | 20 gm. |
| Citric acid | 2 gm. |
| Benzoic acid | 1 gm. |
| Sucrose | 700 gm. |

-continued

| | |
|---|---|
| Tragacanth | 5 gm. |
| Lemon oil | 2 ml. |
| Deionized water q.s. | 1000 ml. |

The citric acid, benzoic acid, sucrose, tragacanth, and lemon oil are dispersed in sufficient water to make 850 ml. of solution. The 4-(methyl-n-butylamino)-4-(m-hydroxyphenyl)cyclohexan-1-one ethylene ketal hydrochloride is stirred into the syrup until uniformly distributed. Sufficient water is added to make 1000 ml.

The composition so prepared is useful in the treatment of headache in adult humans at a dose of 1 teaspoonful 4 times a day.

EXAMPLE 90

Parenteral solution

A sterile aqueous solution for intramuscular use, containing in 1 ml. 25 mg. of 4-(methyl-n-butylamino)-4-(m-hydroxyphenyl)cyclohexan-1-one ethylene ketal hydrochloride is prepared from the following types and amounts of materials:

| | |
|---|---|
| 4-(methyl-n-butylamino)-4-(m-hydroxyphenyl)cyclohexan-1-one ethylene ketal hydrochloride | 25 gm. |
| Lidocaine hydrochloride | 4 gm. |
| Methylparaben | 2.5 gm. |
| Propylparaben | 0.17 gm. |
| Water for injection q.s. | 1000 ml. |

The ingredients are dissolved in the water and the solution sterilized by filtration. The sterile solution is filled into vials and the vials sealed.

EXAMPLE 91

Suppository, rectal

One thousand suppositories, each weighing 2.5 gm. and containing 100 mg. of 4-(methyl-n-butylamino)-4-(m-hydroxyphenyl)cyclohexan-1-one ethylene ketal hydrochloride are prepared from the following types and amounts of ingredients:

| | |
|---|---|
| 4-(methyl-n-butylamino)-4-(m-hydroxyphenyl)cyclohexan-1-one ethylene ketal hydrochloride | 100 gm. |
| Propylene glycol | 162.5 gm. |
| Polyethylene glycol 4000 q.s. | 2500 gm. |

The 4-(methyl-n-butylamino)-4-(m-hydroxyphenyl)cyclohexan-1-one ethylene ketal hydrochloride is added to the propylene glycol and the mixture milled until the powders are finely divided and uniformly dispersed. The polyethylene glycol 4000 is melted and the propylene glycol dispersion added slowly with stirring. The suspension is poured into unchilled molds at 40° C. The composition is allowed to cool and solidify and then removed from the mold and each suppository foil wrapped.

The suppositories are useful in the treatment of headache by the insertion rectally of 1 suppository every six hours.

EXAMPLE 92

Compositions are similarly prepared following the procedure of the preceding Examples 85 through 91 substituting an equimolar amount each of 4-(p-chlorophenyl)-4-dimethylaminocyclohexanone, ethylene ketal free base;
4-(p-chlorophenyl)-4-dimethylaminocyclohexanone, ethylene ketal hydrochloride;
4-(p-chlorophenyl)-4-dimethylaminocyclohexanone;
4-(p-fluorophenyl)-4-dimethylaminocyclohexanone, ethylene ketal free base;
4-(p-fluorophenyl)-4-dimethylaminocyclohexanone, ethylene ketal hydrochloride;
4-(p-fluorophenyl)-4-dimethylaminocyclohexanone;
4-(p-anisyl)-4-dimethylaminocyclohexanone, ethylene ketal free base;
4-(p-anisyl)-4-dimethylaminocyclohexanone, ethylene ketal hydrochloride;
4-(p-anisyl)-4-dimethylaminocyclohexanone free base;
4-(o-chlorophenyl)-4-dimethylaminocyclohexanone, ethylene ketal free base;
4-(o-chlorophenyl)-4-dimethylaminocyclohexanone, ethylene ketal hydroiodide;
4-(o-chlorophenyl)-4-dimethylaminocyclohexanone;
4-(m-anisyl)-4-dimethylaminocyclohexanone, ethylene ketal free base;
4-(m-anisyl)-4-dimethylaminocyclohexanone, ethylene ketal hydrochloride;
4-(m-anisyl)-4-dimethylaminocyclohexanone;
4-dimethylamino-4-(p-tolyl)cyclohexanone, ethylene ketal free base;
4-dimethylamino-4-(p-tolyl)cyclohexanone, ethylene ketal hydrochloride;
4-dimethylamino-4-(p-tolyl)cyclohexanone;
4-dimethylamino-4-phenylcyclohexanone;
4-(p-bromophenyl)-4-dimethylaminocyclohexanone, ethylene ketal free base;
4-(p-bromophenyl)-4-dimethylaminocyclohexanone, ethylene ketal hydrochloride;
4-(p-bromophenyl)-4-dimethylaminocyclohexanone;
4-(2,4-dichlorophenyl)-4-dimethylaminocyclohexanone, ethylene ketal free base;
4-(2,4-dichlorophenyl)-4-dimethylaminocyclohexanone, ethylene ketal hydrochloride;
4-dimethylamino-4-(2-thienyl)cyclohexanone, ethylene ketal;
4-(m-tolyl)-4-dimethylaminocyclohexanone free base;
4-(methyl-n-butylamino)-4-(m-hydroxyphenyl)cyclohexan-1-one, ethylene ketal free base;
4-(methyl-n-butylamino)-4-(m-hydroxyphenyl)cyclohexan-1-one, ethylene ketal hydrochloride;
4-(m-hydroxyphenyl)-4-(methyl-n-butylamino)cyclohexanone;
4-(m-hydroxyphenyl)-4-dimethylaminocyclohexanone, ethylene ketal;
4-(m-hydroxyphenyl)-4-dimethylaminocyclohexanone;
4-(p-hydroxyphenyl)-4-(n-butylmethylamino)cyclohexanone ethylene ketal free base;
4-(p-hydroxyphenyl)-4-(n-butylmethylamino)cyclohexanone ethylene ketal hydrochloride;
4-(p-hydroxyphenyl)-4-(n-butylmethylamino)cyclohexanone;
4-(p-trifluoromethylphenyl)-4-dimethylaminocyclohexanone, ethylene ketal free base;
4-(p-trifluoromethylphenyl)-4-dimethylaminocyclohexanone, ethylene ketal hydrochloride, 4-(p-chlorophenyl)-cis-2-methyl-4-dimethylaminocyclohexanone;
4-(p-chlorophenyl)-trans-2-methyl-4-dimethylaminocyclohexanone;
4-(m-hydroxyphenyl)-4-(n-propylmethylamino)cyclohexanone ethylene ketal free base;
4-(m-hydroxyphenyl)-4-(n-propylmethylamino)cyclohexanone, ethylene ketal hydrochloride;
4-(m-hydroxyphenyl)-4-(methyl-N-pentylamino)cyclohexanone ethylene ketal free base;
4-(m-hydroxyphenyl)-4-(methyl-n-pentylamino)cyclohexanone ethylene ketal hydrochloride;
4-(m-hydroxyphenyl)-4-(i-butylmethylamino)cyclohexanone ethylene ketal free base;
4-(m-hydroxyphenyl)-4-(i-butylmethylamino)cyclohexanone ethylene ketal hydrochloride;
4-(m-acetoxyphenyl)-4-dimethylaminocyclohexan-1-one;
4-(m-acetoxyphenyl)-4-(methyl-n-butylamino)cyclohexanone;
4-(m-hydroxyphenyl)-4-(1-pyrrolidinyl)cyclohexanone;
4-(m-hydroxyphenyl)-4-(1-pyrrolidinyl)cyclohexanone, ethylene ketal;
4-(m-acetoxyphenyl)-4-(1-pyrrolidinyl)cyclohexanone;
4-(m-hydroxyphenyl)-4-dimethylaminocyclohexanone trimethylene ketal;
4-(m-acetoxyphenyl)-4-(n-propylmethylamino)cyclohexanone;
4-(m-acetoxyphenyl)-4-(isobutylmethylamino)cyclohexanone;
4-(m-acetoxyphenyl)-4-(n-pentylmethylamino)cyclohexanone;
4-(m-hydroxyphenyl)-4-dimethylaminocyclohexanone trimethylene ketal;
4-(m-acetoxyphenyl)-4-(n-butylmethylamino)cyclohexanone hydrochloride; and
4-(m-hydroxyphenyl)-4-(n-propylmethylamino)cyclohexanone for the 4-(methyl-n-butylamino)-4-(m-hydroxyphenyl)cyclohexan-1-one ethylene ketal hydrochloride of the examples.

EXAMPLE 93

The compositions prepared in the preceding Examples 85, 87, 89, 90 and 91 can be used for testing the narcotic dependence by inducing withdrawal symptoms in drug addicts. Also, they are useful for counteracting respiratory and central nervous system depression induced by morphine or related analgesics.

Although compounds of Formula VIII can induce analgesia, their additional activity of being at the same time narcotic antagonists considerably diminishes the risk of addiction to the particular drug. One can say that the narcotic antagonist activity of the compounds of this invention acts as an internal safety device directed toward moderating any inherent properties of physical dependence of the medication caused by its narcotic-type analgetic action. As a result, one can use the free bases or salts to obtain narcotic type analgesia with minimal risk of physical dependence.

I claim:

1. A compound of the formula:

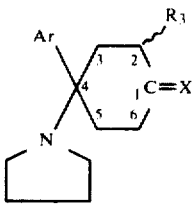

wherein X is

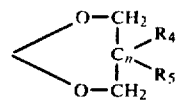

wherein n is zero or one and $R_4$ is hydrogen or methyl; $R_5$ is hydrogen, phenyl, —$CH_2$-alkenyl wherein alkenyl is of 2 to 4 carbon atoms, inclusive, or methyl; aryl is thiophene, or

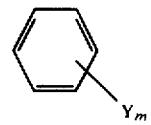

wherein m is zero, one or two, and Y is halogen, $CF_3$, alkyl of 1 to 4 carbon atoms, inclusive, alkoxy of 1 to 4 carbon atoms, inclusive, hydroxy, cycloalkyloxy of 3 to 6 carbon atoms, inclusive, alkanoyloxy of 2 to 4 carbon atoms, inclusive, alkylthio of 1 to 4 carbon atoms, inclusive, or

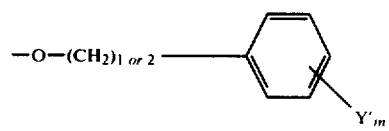

where Y' is halogen, $CF_3$, alkyl of 1 to 4 carbon atoms, inclusive, or alkoxy of 1 to 4 carbon atoms, inclusive; $R_3$ is hydrogen, alkyl of 1 to 5 carbon atoms, inclusive, and the acid addition salts thereof.

2. A pharmaceutical composition in unit dosage form comprising as an active ingredient an effective amount of a compound of the formula:

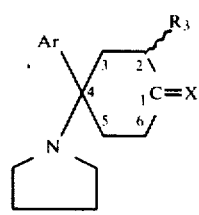

wherein X is

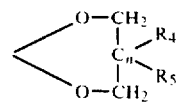

wherein n is zero or one and $R_4$ is hydrogen or methyl; $R_5$ is hydrogen, phenyl, —$CH_2$-alkenyl wherein alkenyl is of 2 to 4 carbon atoms, inclusive, or methyl; aryl is thiophene, or

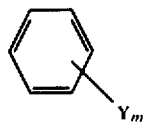

wherein m is zero, one or two, and Y is halogen, $CF_3$, alkyl of 1 to 4 carbon atoms, inclusive, alkoxy of 1 to 4 carbon atoms, inclusive, hydroxy, cycloalkyloxy of 3 to 6 carbon atoms, inclusive, alkanoyloxy of 2 to 4 carbon atoms, inclusive, alkylthio of 1 to 4 carbon atoms, inclusive, or

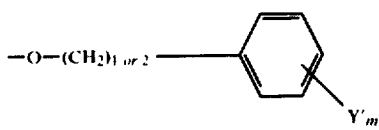

where Y' is halogen, $CF_3$, alkyl of 1 to 4 carbon atoms, inclusive, or alkoxy of 1 to 4 carbon atoms, inclusive; $R_3$ is hydrogen, alkyl of 1 to 5 carbon atoms, inclusive, and the acid addition salts thereof, in association with a pharmaceutical carrier.

3. A process for inducing analgesia in humans and animals comprising the administration of an analgetic amount of a compound of the formula:

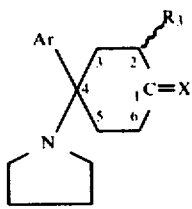

wherein X is

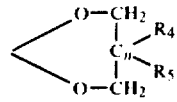

wherein n is zero or one and $R_4$ is hydrogen or methyl; $R_5$ is hydrogen, phenyl, —$CH_2$-alkenyl wherein alkenyl is of 2 to 4 carbon atoms, inclusive, or methyl; aryl is thiophene, or

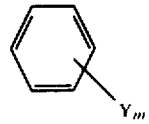

wherein m is zero, one or two, and Y is halogen, $CF_3$, alkyl of 1 to 4 carbon atoms, inclusive, alkoxy of 1 to 4 carbon atoms, inclusive, hydroxy, cycloalkyloxy of 3 to 6 carbon atoms, inclusive, alkanoyloxy of 2 to 4 carbon atoms, inclusive, alkylthio of 1 to 4 carbon atoms, inclusive, or

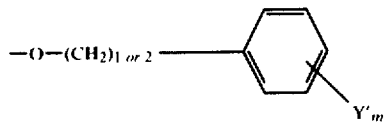

where Y' is halogen, $CF_3$, alkyl of 1 to 4 carbon atoms, inclusive, or alkoxy of 1 to 4 carbon atoms, inclusive; $R_3$ is hydrogen, alkyl of 1 to 5 carbon atoms, inclusive, and the acid addition salts thereof, to a human or animal subject.

4. A compound according to claim 1 which is 4-(m-hydroxyphenyl)-4-(1-pyrrolidinyl)cyclohexanone, ethylene ketal.

5. A composition according to claim 2 wherein the active ingredient is present in unit dosage form of from 0.5 mg. to 500 mg.

6. A process according to claim 3 wherein the amount of compound administered is from about 0.01 mg. to about 7 mg. per kilogram of human or animal weight.

* * * * *